(12) United States Patent
Aliagas-Martin et al.

(10) Patent No.: US 8,815,877 B2
(45) Date of Patent: Aug. 26, 2014

(54) SERINE/THREONINE KINASE INHIBITORS

(71) Applicant: Genentech, Inc., South San Francisco, CA (US)

(72) Inventors: Ignacio Aliagas-Martin, San Francisco, CA (US); James Crawford, South San Francisco, CA (US); Wendy Lee, San Ramon, CA (US); Simon Mathieu, San Francisco, CA (US); Joachim Rudolph, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 6 days.

(21) Appl. No.: 13/723,770

(22) Filed: Dec. 21, 2012

(65) Prior Publication Data
US 2013/0178486 A1 Jul. 11, 2013

Related U.S. Application Data

(60) Provisional application No. 61/579,227, filed on Dec. 22, 2011.

(51) Int. Cl.
*C07D 403/12* (2006.01)
*A61K 31/505* (2006.01)

(52) U.S. Cl.
USPC ......... 514/265.1; 514/275; 544/262; 544/324

(58) Field of Classification Search
USPC .................. 544/262, 324; 514/265.1, 275
See application file for complete search history.

(56) References Cited

U.S. PATENT DOCUMENTS

| | | | |
|---|---|---|---|
| 6,610,677 B2 | 8/2003 | Davies et al. |
| 6,613,776 B2 | 9/2003 | Knegtel et al. |
| 6,638,926 B2 | 10/2003 | Davies et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,696,452 B2 | 2/2004 | Davies et al. |

(Continued)

FOREIGN PATENT DOCUMENTS

| | | |
|---|---|---|
| WO | 02/22601 A1 | 3/2002 |
| WO | 02/22602 A2 | 3/2002 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak Rao
(74) *Attorney, Agent, or Firm* — Brian L. Buckwalter

(57) ABSTRACT

Compounds having the formula I wherein A, $R^{1a}$, $R^{1b}$, $R^2$, $R^3$, $R^4$, $R^5$, $R^6$, $R^7$, $R^8$, $R^a$, $R^b$, $X^1$, $X^2$, $X^3$ and n are as defined herein are inhibitors of PAK1. Also disclosed are compositions and methods for treating cancer and hyperproliferative disorders.

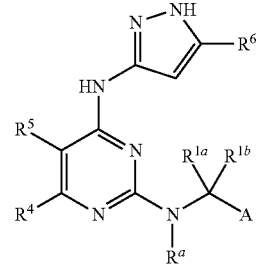

(I)

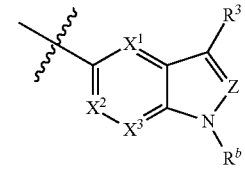

A-1

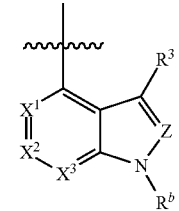

A-2

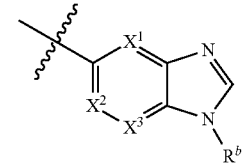

A-3

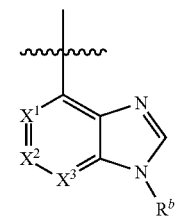

A-4

17 Claims, No Drawings

(56) References Cited

U.S. PATENT DOCUMENTS

| | | |
|---|---|---|
| 6,727,251 B2 | 4/2004 | Bebbington et al. |
| 6,989,385 B2 | 1/2006 | Bebbington et al. |
| 7,008,948 B2 | 3/2006 | Bebbington et al. |
| 7,087,603 B2 | 8/2006 | Bebbington et al. |
| 7,098,330 B2 | 8/2006 | Bebbington et al. |
| 7,115,739 B2 | 10/2006 | Bebbington et al. |
| 7,390,815 B2 | 6/2008 | Davies et al. |
| 7,427,681 B2 | 9/2008 | Bebbington et al. |
| 7,473,691 B2 | 1/2009 | Davies et al. |
| 7,531,536 B2 | 5/2009 | Bebbington et al. |
| 7,625,913 B2 | 12/2009 | Bebbington et al. |
| 7,691,853 B2 | 4/2010 | Bebbington et al. |
| 7,754,714 B2 | 7/2010 | Li et al. |
| 7,858,633 B2 | 12/2010 | Li et al. |
| 7,868,013 B2 | 1/2011 | Li et al. |
| 7,884,111 B2 | 2/2011 | Argade et al. |
| 2003/0004161 A1 | 1/2003 | Bebbington et al. |
| 2003/0004164 A1 | 1/2003 | Bebbington et al. |
| 2003/0022885 A1 | 1/2003 | Bebbington et al. |
| 2003/0036543 A1 | 2/2003 | Bebbington et al. |
| 2003/0055068 A1 | 3/2003 | Bebbington et al. |
| 2003/0064981 A1 | 4/2003 | Knegtel et al. |
| 2003/0064982 A1 | 4/2003 | Davies et al. |
| 2003/0073687 A1 | 4/2003 | Bebbington et al. |
| 2003/0078166 A1 | 4/2003 | Davies et al. |
| 2003/0078275 A1 | 4/2003 | Bebbington et al. |
| 2003/0083327 A1 | 5/2003 | Davies et al. |
| 2003/0105090 A1 | 6/2003 | Bebbington et al. |
| 2004/0097501 A1 | 5/2004 | Bebbington et al. |
| 2004/0116454 A1 | 6/2004 | Davies et al. |
| 2004/0132781 A1 | 7/2004 | Bebbington et al. |
| 2004/0157893 A1 | 8/2004 | Bebbington et al. |
| 2004/0167141 A1 | 8/2004 | Bebbington et al. |
| 2004/0214814 A1 | 10/2004 | Bebbington et al. |
| 2005/0038023 A1 | 2/2005 | Bebbington et al. |
| 2005/0113398 A1 | 5/2005 | Argade et al. |
| 2006/0162249 A1 | 7/2006 | Zimmermann et al. |
| 2006/0258658 A1 | 11/2006 | Bebbington et al. |
| 2007/0270444 A1 | 11/2007 | Bebbington et al. |
| 2008/0009484 A1 | 1/2008 | Argade et al. |
| 2008/0287444 A1 | 11/2008 | Bebbington et al. |
| 2009/0312543 A1 | 12/2009 | Bebbington et al. |
| 2010/0256170 A1 | 10/2010 | Bebbington et al. |

FOREIGN PATENT DOCUMENTS

| | | |
|---|---|---|
| WO | 02/22602 A3 | 3/2002 |
| WO | 02/22603 A1 | 3/2002 |
| WO | 02/22604 A1 | 3/2002 |
| WO | 02/22605 A1 | 3/2002 |
| WO | 02/22606 A1 | 3/2002 |
| WO | 02/22607 A1 | 3/2002 |
| WO | 02/22608 A1 | 3/2002 |
| WO | 02/50065 A2 | 6/2002 |
| WO | 02/50065 A3 | 6/2002 |
| WO | 02/057259 A2 | 7/2002 |
| WO | 02/057259 A3 | 7/2002 |
| WO | 02/059111 A2 | 8/2002 |
| WO | 02/059111 A3 | 8/2002 |
| WO | 02/059112 A2 | 8/2002 |
| WO | 02/059112 A3 | 8/2002 |
| WO | 02/062789 A1 | 8/2002 |
| WO | 02/066461 A1 | 8/2002 |
| WO | 02/068415 A1 | 9/2002 |
| WO | 2005/013996 A2 | 2/2005 |
| WO | 2005/013996 A3 | 2/2005 |
| WO | 2005/049033 A1 | 6/2005 |
| WO | 2006/074057 A2 | 7/2006 |
| WO | 2006/074057 A3 | 7/2006 |
| WO | 2006/115452 A1 | 11/2006 |
| WO | 2006/123113 A2 | 11/2006 |
| WO | 2006/123113 A3 | 11/2006 |
| WO | 2006/124462 A2 | 11/2006 |
| WO | 2006/124462 A3 | 11/2006 |
| WO | 2007/056221 A2 | 5/2007 |
| WO | 2007/056221 A3 | 5/2007 |
| WO | 2007/059299 A1 | 5/2007 |
| WO | 2007/4049041 A1 | 5/2007 |
| WO | 2008/005538 A2 | 1/2008 |
| WO | 2008/005538 A3 | 1/2008 |
| WO | 2008/137619 A2 | 11/2008 |
| WO | 2008/137619 A3 | 11/2008 |
| WO | 2008/147626 A2 | 12/2008 |
| WO | 2008/147626 A3 | 12/2008 |
| WO | 2011/060295 A1 | 5/2011 |
| WO | 2011/060295 A8 | 5/2011 |
| WO | 2011/144742 A1 | 11/2011 |

OTHER PUBLICATIONS

Johnson et al., Relationships between drug activity in NCI preclinical in vitro and in vivo models and early clinical trials, British Journal of Cancer, 84(10):1424-1431, 2001.*

Gura et al., Systems for identifying new drugs are often faulty, Science, 278:1041-1042, 1997.*

Simone, Oncology: Introduction, Cecil Textbook of Medicine, 20th Editino, vol. 1, pp. 1004-1010, 1996.*

N.E. Sharpless et al., Nature Reviews Drug Discovery, 741-754, 742 (2006).*

A. Kamb, Nature Reviews Drug Discovery 2, 161-165 (2005).*

F. Smith, Molecular Cancer Therapeutics, 6, 428-440, 428 (2007).*

International Search Report and Written Opinion for International Patent Application No. PCT/EP/2012/076531, (2013).

* cited by examiner

SERINE/THREONINE KINASE INHIBITORS

CROSS REFERENCE TO PRIOR APPLICATIONS

This application claims the benefit of priority to U.S. Ser. No. 61/579,227 filed Dec. 22, 2011, which is incorporated herein by reference in its entirety.

FIELD OF THE INVENTION

The present invention relates to compounds which inhibit serine/threonine kinases and which are useful for treating hyperproliferative and neoplastic diseases by inhibiting signal transduction pathways which commonly are overactive or over-expressed in cancerous tissue. The present compounds are inhibitors of group 1 p21-activated protein kinases (PAK1, PAK2 and PAK3). The present invention further relates to methods for treating cancer or hyperproliferative diseases with compounds within the scope of the present invention.

BACKGROUND OF THE INVENTION

Protein kinases are a family of enzymes that catalyze phosphorylation of the hydroxyl groups of specific tyrosine, serine, or threonine residues in proteins. Typically, such phosphorylation can dramatically change the function of the protein and thus protein kinases can be pivotal in the regulation of a wide variety of cellular process, including metabolism, cell proliferation, cell differentiation, and cell survival. The mechanism of these cellular processes provides a basis for targeting protein kinases to treat disease conditions resulting from or involving disorder of these cellular processes. Examples of such diseases include, but are not limited to, cancer and diabetes.

Protein kinases can be broken into two types, protein tyrosine kinases (PTKs) and serine-threonine kinases (STKs). Both PTKs and STKs can be receptor protein kinases or non-receptor protein kinases. PAK is a family of non-receptor STKs. The p21-activated protein kinase (PAK) family of serine/threonine protein kinases plays important roles in cytoskeletal organization, cellular morphogenesis, cellular processes and cell survival (Daniels et al., *Trends Biochem. Sci.* 1999 24: 350-355; Sells et al., *Trends Cell. Biol.* 1997 7:162-167). The PAK family consists of six members subdivided into two groups: PAK 1-3 (group I) and PAK 4-6 (group II) which are distinguished based upon sequence homologies and the presence of an autoinhibitory region in group I PAKs. p21-Activated kinases (PAKs) serve as important mediators of Rac and Cdc42 GTPase function as well as pathways required for Ras-driven tumorigenesis. (Manser et al., *Nature* 1994 367:40-46; B. Dummler et al., *Cancer Metathesis Rev.* 2009 28:51-63; R. Kumar et al., *Nature Rev. Cancer* 2006 6:459-473).

Changes in the levels and activities of group 1 PAKs in particular, are frequently associated with human malignancies including, but not limited to bladder carcinoma, breast carcinoma, colorectal carcinoma, gastric carcinoma, glioblastoma, hepatocellular carcinoma, ovarian carcinoma and renal cell carcinoma, primary breast adenocarcinoma, squamous non-small cell lung cancer or a squamous head and necks cancer. (J. V. Kichina et al., *Expert. Opin. Ther. Targets* 2010 14(7):703) PAK1 genomic amplification at 11q13 was prevalent in luminal breast cancer, and PAK1 protein expression was associated with lymph node metastasis. High expression of PAK2 in mammary invasive ductal carcinomas has been associated with increased survival and resistance of breast tumor cells to chemotherapeutic agents (X. Li et al., *J. Biol. Chem.* 2011 286(25):2291) Squamous non-small cell lung carcinomas (NSCLCs), and head and neck squamous carcinomas have aberrant cytoplasmic expression of PAK1. (C. C. Ong et al., *Proc. Nat. Acad. Sci., USA* 2011 108(17): 7177) Group 1 PAKs contribute to squamous NSCLC cell motility, survival and proliferation (C. C. Ong et al., *Oncotarget* 2011 2(6):491) and PAK2 has been linked to mitosis completion in response to various cell stimuli (M. R. Banko et al., *Mol. Cell.* 2011, Nov. 30, 2011)

SUMMARY OF THE INVENTION

There is a continuing need for new and novel therapeutic agents that can be used for cancer and hyperproliferative conditions. The PAK family are important signaling proteins frequently over-expressed and/or overactive in many cancerous tissues. Design and development of new pharmaceutical compounds that inhibit or modulate their activity is essential. In one aspect of the present invention there is provided a compound according to formula I wherein:

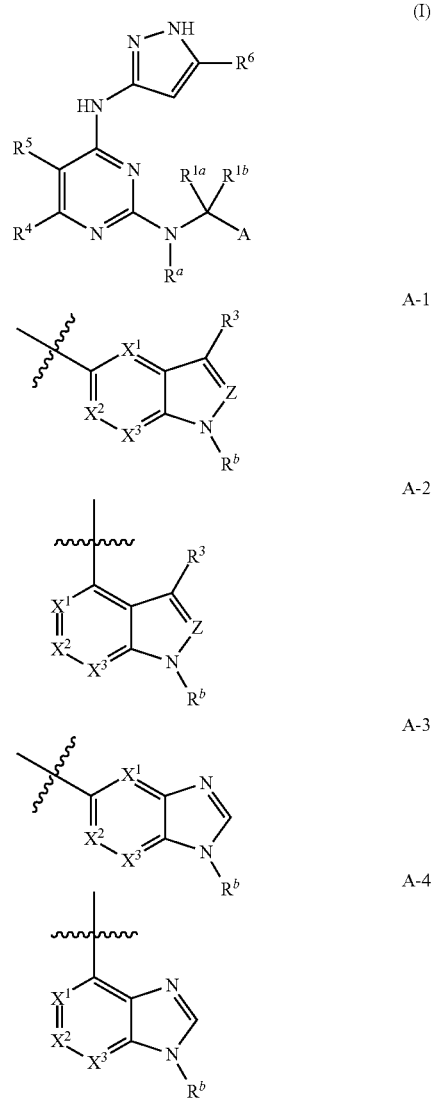

A is A-1, A-2 or A-3 wherein one of $X^1$, $X^2$ or $X^3$ is N and the remainder of $X^1$, $X^2$, and $X^3$ are $CR^2$ or when A is A-1, both of $X^1$ and $X^2$ are N and $X^3$ is $CR^2$.

Z is N or $CR^2$.

$R^{1a}$ and $R^{1b}$ are (i) independently hydrogen, $C_{1-6}$ alkyl or $C_{1-6}$ haloalkyl, or (ii) together with the carbon to which they are attached form a $C_{3-7}$ cycloalkane or an oxetane, tetrahydrofuran or tetrahydropyran.

$R^2$ is independently in each occurrence cyano, $C_{1-6}$ alkyl, $-OR^7$, $C_{1-6}$ haloalkyl, $C_{1-6}$ haloalkoxy, halogen or oxetane.

$R^3$ is hydrogen, halogen, $C_{1-6}$ alkyl, $C_{1-6}$ haloalkyl, $C_{1-6}$ acyl, $C_{1-3}$ haloalkanoyl, $C_{3-7}$ cycloalkyl or a $C_{3-6}$ heterocycle group with one oxygen atom.

$R^4$ is hydrogen, $C_{1-6}$ alkyl, $C_{1-6}$ haloalkyl, $-OR^7$, $C_{3-7}$ cycloalkyl or a $C_{3-6}$ heterocycle with one oxygen atom.

$R^5$ is hydrogen, halogen, $C_{1-6}$ alkyl, $C_{1-6}$ haloalkyl, CN or $C_{1-3}$-alkoxy.

$R^6$ is selected from the group consisting of (i) $C_{1-10}$ alkyl, (ii) $C_{1-10}$ haloalkyl, (iii) optionally substituted $C_{3-7}$ cycloalkyl (iv) $C_{3-7}$ cycloalkyl-$C_{1-6}$ alkyl, (v) $[C(R^8)_2]_{0-5}$, $OR^7$ (vi) $C_{3-7}$ heterocyclyl and (vii) $C_{3-7}$ heterocyclyl-$C_{1-6}$ alkyl.

$R^7$ is independently in each occurrence $C_{1-10}$ alkyl, $C_{1-6}$ haloalkyl, $C_{3-7}$ cycloalkyl, $C_{3-7}$ cycloalkyl-$C_{1-6}$ alkyl, phenyl-$C_{1-6}$ alkyl, phenyl.

$R^8$ is independently in each occurrence hydrogen or $C_{1-6}$ alkyl.

$R^b$ is hydrogen or $C_{1-6}$ alkyl.

$R^a$ is (a) hydrogen, (b) $C_{1-6}$ alkyl optionally substituted by one or two groups selected from the group consisting of hydroxyl, $C_{1-3}$ alkoxy or $NR^cR^d$ wherein $R^c$ and $R^d$ are (i) independently hydrogen or $C_{1-3}$ alkyl or (ii) together with the nitrogen to which they are attached form a pyrrolidine, piperidine or azetidine ring, (c) $C_{3-7}$ cycloalkyl or (d) a 4 to 7 member heterocycle containing O or $NR^e$ wherein $R^e$ is hydrogen of $C_{1-3}$ alkyl.

A cycloalkyl in each occurrence is independently optionally substituted with $C_{1-6}$ alkyl, halogen or optionally substituted phenyl.

A phenyl in each occurrence is independently optionally substituted with $C_{1-6}$ alkyl, halogen, $C_{1-6}$ alkoxy.

A heterocyclyl is independently substituted with halogen or $C_{1-6}$ alkyl.

The present invention further relates to a pharmaceutically acceptable salt of compounds disclosed herein.

The present invention further relates to stereoisomers, tautomers or pharmaceutically acceptable salts of compounds of formula I as described above.

Another aspect of the present invention relates to a method for treating a hyperproliferative disorder by administering a therapeutically effective quantity of a compound according to formula I to a patient in need thereof. The compound can be administered alone or co-administered with at least one other anti-hyperproliferative or chemotherapeutic compound.

Another aspect of the present invention relates to a method for inhibiting PAK activity in a cell comprising treating a cell with a compound according to formula I in an amount effective to attenuate or eliminate PAK activity.

Another aspect of the present invention relates to pharmaceutical compositions containing a compound of formula I with one or more pharmaceutically acceptable excipients, diluents and/or carriers.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

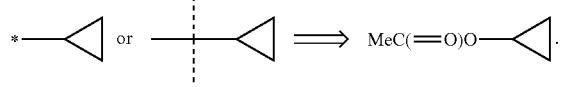

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomer usually produces a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH-⇌-C(—OH)=CH—), amide/imidic acid (—C(=O)—NH-⇌-C(—OH)=N—) and amidine (—C(=NR)—NH-⇌-C(—NHR)=N—) tautomers. The latter two are particularly common in heteroaryl and heterocyclic rings and the present invention encompasses all tautomeric forms of the compounds.

The compounds of formula I may contain an acidic or basic center and suitable salts are formed from acids or bases may form non-toxic salts which have similar antiviral activity. Examples of salts of inorganic acids include the hydrochloride, hydrobromide, hydroiodide, chloride, bromide, iodide, sulfate, bisulfate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

In one embodiment of the present invention there is provided a compound according to formula I wherein A is A-1, A-2 or A-3 wherein one of $X^1$, $X^2$ or $X^3$ is N and the remainder of $X^1$, $X^2$, and $X^3$ are $CR^2$ or when A is A-1, both of $X^1$ and $X^2$ are N and $X^3$ is $CR^2$; Z is N or $CR^2$; $R^{1a}$ and $R^{1b}$ are (i) independently hydrogen, $C_{1-6}$ alkyl or $C_{1-6}$ haloalkyl, or (ii) together with the carbon to which they are attached form a $C_{3-7}$ cycloalkane or an oxetane, tetrahydrofuran or tetrahydropyran; $R^2$ is independently in each occurrence cyano, $C_{1-6}$ alkyl, —$OR^7$, $C_{1-6}$ haloalkyl, $C_{1-6}$ haloalkoxy, halogen or oxetane; $R^3$ is hydrogen, halogen, $C_{1-6}$ alkyl, $C_{1-6}$ haloalkyl, $C_{1-6}$ acyl, $C_{1-3}$ haloalkanoyl, $C_{3-7}$ cycloalkyl or a $C_{3-6}$ heterocycle group with one oxygen atom; $R^4$ is hydrogen, $C_{1-6}$ alkyl, $C_{1-6}$ haloalkyl, —$OR^7$, $C_{3-7}$ cycloalkyl or a $C_{3-6}$ heterocycle with one oxygen atom; $R^5$ is hydrogen, halogen, $C_{1-6}$ alkyl, $C_{1-6}$ haloalkyl, CN or $C_{1-3}$-alkoxy; $R^6$ is selected from the group consisting of (i) $C_{1-10}$ alkyl, (ii) $C_{1-10}$ haloalkyl, (iii) optionally substituted $C_{3-7}$ cycloalkyl (iv) $C_{3-7}$ cycloalkyl-$C_{1-6}$ alkyl, (v) $[C(R^8)_2]_{0-6}$, $OR^7$ (vi) $C_{3-7}$ heterocyclyl and (vii) $C_{3-7}$ heterocyclyl-$C_{1-6}$ alkyl; $R^7$ is independently in each occurrence $C_{1-10}$ alkyl, $C_{1-6}$ haloalkyl, $C_{3-7}$ cycloalkyl, $C_{3-7}$ cycloalkyl-$C_{1-6}$ alkyl, phenyl-$C_{1-6}$ alkyl, phenyl; $R^8$ is independently in each occurrence hydrogen or $C_{1-6}$ alkyl; $R^b$ is hydrogen or $C_{1-6}$ alkyl; $R^a$ is (a) hydrogen, (b) $C_{1-6}$ alkyl optionally substituted by one or two groups selected from the group consisting of hydroxyl, $C_{1-3}$ alkoxy or $NR^cR^d$ wherein $R^c$ and $R^d$ are (i) independently hydrogen or $C_{1-3}$ alkyl or (ii) together with the nitrogen to which they are attached form a pyrrolidine, piperidine or azetidine ring, (c) $C_{3-7}$ cycloalkyl or (d) a 4 to 7 member heterocycle containing O or $NR^e$ wherein $R^e$ is hydrogen of $C_{1-3}$ alkyl; said cycloalkyl in each occurrence is independently optionally substituted with $C_{1-6}$ alkyl, halogen or optionally substituted phenyl; said phenyl in each occurrence is independently optionally substituted with $C_{1-6}$ alkyl, halogen, $C_{1-6}$ alkoxy; said heterocyclyl is independently substituted with halogen or $C_{1-6}$ alkyl; or, a pharmaceutically acceptable salt thereof.

In one embodiment of the present invention there is provided a compound according to formula I wherein A, $R^{1a}$, $R^{1b}$, $R^2$, $R^3$, $R^4$, $R^5$, $R^6$, $R^7$, $R^8$, $R^a$, $R^b$, $X^1$, $X^2$ and $X^3$ are as defined herein above. The phrase "as defined herein above" when referring to a variable incorporates by reference the broadest definition for each group as provided in the Summary of the Invention or the broadest claim. In all other embodiments provided below substituents which can be present in each embodiment and which are not explicitly defined retain the broadest definition permitted in the Summary of the Invention.

In an embodiment of the present invention there is provided a compound according to formula I wherein A is A-1, $X^1$ is N and $X^2$, $X^3$ and Z are independently $CR^2$. In a subembodiment $CR^2$ is CH (i.e., A is 1H-pyrrolo[3,2-b]pyridin-5-yl). In another subembodiment A is 1H-pyrrolo[3,2-b]pyridin-5-yl, $R^{1a}$ is hydrogen or $C_{1-6}$ alkyl, $R^{1b}$ is hydrogen, $R^6$ optionally substituted $C_{3-7}$ cycloalkyl and IV is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are independently hydrogen or $C_{1-3}$ alkyl.

In an embodiment of the present invention there is provided a compound according to formula I wherein A is A-1, $X^2$ is N and $X^1$, $X^3$ and Z are independently $CR^2$. In a subembodiment $CR^2$ is CH (i.e., A is 1H-pyrrolo[2,3-c]pyridin-5-yl). In another subembodiment A is 1H-pyrrolo[2,3-c]pyridin-5-yl, $R^{1a}$ is hydrogen or $C_{1-6}$ alkyl, $R^{1b}$ is hydrogen $R^6$ optionally substituted $C_{3-7}$ cycloalkyl and $R^a$ is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are independently hydrogen or $C_{1-3}$ alkyl.

In an embodiment of the present invention there is provided a compound according to formula I wherein A is A-1, $X^3$ is N and $X^1$, $X^2$ and Z are independently $CR^2$. In a subembodiment $CR^2$ is CH (i.e., A is 1H-pyrrolo[2,3-b]pyridin-5-yl). In another subembodiment A is 1H-pyrrolo[2,3-b]pyridin-5-yl] pyridin-5-yl, $R^b$ is hydrogen or $C_{1-6}$ alkyl, $R^{1b}$ is hydrogen, $R^6$ optionally substituted $C_{3-7}$ cycloalkyl and $R^a$ is hydrogen or $C_{1-6}$ alkyl optionally substituted by one or two groups selected from the group consisting of hydroxyl, $C_{1-3}$ alkoxy or $NR^eR^d$ wherein $R^e$ and $R^d$ are independently hydrogen or $C_{1-3}$ alkyl.

In an embodiment of the present invention there is provided a compound according to formula I wherein A is A-2, $X^1$ is N and $X^2$, $X^3$ and Z are independently $CR^2$. In a subembodiment $CR^2$ is CH (i.e., A is 1H-pyrrolo[3,2-c]pyridin-4-yl). In another subembodiment A is 1H-pyrrolo[3,2-c]pyridin-4-yl, $R^b$ is hydrogen or $C_{1-6}$ alkyl, $R^{1b}$ is hydrogen, $R^6$ optionally substituted $C_{3-7}$ cycloalkyl and $R^a$ is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are independently hydrogen or $C_{1-3}$ alkyl.

In an embodiment of the present invention there is provided a compound according to formula I wherein A is A-1, $X^1$ is N and $X^2$, $X^3$ and Z are independently $CR^2$. In a subembodiment $CR^2$ is CH (i.e., A is 1H-pyrrolo[2,3-c]pyridin-4yl). In another subembodiment A is 1H-pyrrolo[2,3-c]pyridin-4yl, $R^{1a}$ is hydrogen or $C_{1-6}$ alkyl, $R^{1b}$ is hydrogen, $R^6$ optionally substituted $C_{3-7}$ cycloalkyl and IV is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are independently hydrogen or $C_{1-3}$ alkyl.

In an embodiment of the present invention there is provided a compound according to formula I wherein A is A-1, $X^1$ is N and $X^2$, $X^3$ and Z are independently $CR^2$. In a subembodiment $CR^2$ is CH (i.e., A is 1H-pyrrolo[2,3-b]pyridin-4-yl). In another subembodiment A is 1H-pyrrolo[2,3-b]pyridin-4-yl, $R^{1a}$ is hydrogen or $C_{1-6}$ alkyl, $R^{1b}$ is hydrogen, $R^6$ optionally substituted $C_{3-7}$ cycloalkyl and $R^a$ is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are independently hydrogen or $C_{1-3}$ alkyl.

In an embodiment of the present invention there is provided a compound according to formula I wherein A is A-4, $X^2$ is N and $X^1$ and $X^3$ are independently $CR^2$. In a subembodiment $CR^2$ is CH (i.e., A is 3H-imidazo[4,5-c]pyridin-7-yl). In another subembodiment A is 3H-imidazo[4,5-c]pyridin-7-yl, $R^{1a}$ is hydrogen or $C_{1-6}$ alkyl, $R^{1b}$ is hydrogen, $R^6$ optionally substituted $C_{3-7}$ cycloalkyl and $R^a$ is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are independently hydrogen or $C_{1-3}$ alkyl.

In an embodiment of the present invention there is provided a compound according to formula I wherein A is A-3, $X^2$ is N and $X^1$ and $X^3$ are independently $CR^2$. In a subembodiment $CR^2$ is CH (i.e., A is 3H-imidazo[4,5-c]pyridin-6-yl). In one embodiment A is 3H-imidazo[4,5-c]pyridin-7-yl, $R^{1a}$ is hydrogen or $C_{1-6}$ alkyl, $R^{1b}$ is hydrogen, $R^6$ optionally substituted $C_{3-7}$ cycloalkyl and IV is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are independently hydrogen or $C_{1-3}$ alkyl.

In an embodiment of the present invention there is provided a compound according to formula I wherein A is A-2, $X^2$ and Z are N and $X^1$ and $X^3$ are $CR^2$. In a subembodiment $CR^2$ is CH (i.e., A is 1H-pyrazolo[3,4-c]pyridin-4-yl. In another subembodiment A is 1H-pyrazolo[3,4-c]pyridin-4-yl, $R^{1a}$ is hydrogen or $C_{1-6}$ alkyl, $R^{1b}$ is hydrogen, $R^6$ optionally substituted $C_{3-7}$ cycloalkyl and $R^a$ is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are independently hydrogen or $C_{1-3}$ alkyl.

In an embodiment of the present invention there is provided a compound according to formula I wherein A is A-1, $X^1$ and $X^2$ are N and $X^3$ and Z are independently $CR^2$. In a subembodiment $CR^2$ is CH (i.e., A is 5H-pyrrolo[3,2-d]pyrimidin-2-yl). In another subembodiment A is 5H-pyrrolo[3,2-d]pyrimidin-2-yl, $R^{1a}$ is re hydrogen or $C_{1-6}$ alkyl, $R^{1b}$ is hydrogen, $R^6$ optionally substituted $C_{3-7}$ cycloalkyl and $R^a$ is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are independently hydrogen or $C_{1-3}$ alkyl.

In an embodiment there is provided a compound according to formula I wherein $R^{1a}$ is hydrogen or $C_{1-6}$ alkyl and $R^{1b}$ is hydrogen. In another embodiment, A is selected from 1H-pyrrolo[3,2-b]pyridin-5-yl, 1H-pyrrolo[2,3-c]pyridin-5-yl, 1H-pyrrolo[2,3-b]pyridin 5-yl, 1H-pyrrolo[2,3-c]pyridin-4-yl, 1H-pyrrolo[2,3-b]pyridin-4-yl, 5H-pyrrolo[3,2-d]pyrimidin-2-yl or 3H-imidazo[4,5-c]pyridin-7-yl and $R^{1a}$ is hydrogen or $C_{1-6}$ alkyl and $R^{1b}$ is hydrogen.

In an embodiment there is provided a compound according to formula I wherein $R^{1a}$ is methyl, $R^{1b}$ is hydrogen and the carbon to which $R^{1a}$ and $R^{1b}$ attached is in the S configuration. In another embodiment, A is selected from 1H-pyrrolo[3,2-b]pyridin-5-yl, 1H-pyrrolo[2,3-c]pyridin-5-yl, 1H-pyrrolo[2,3-b]pyridin-5-yl, 1H-pyrrolo[2,3-c]pyridin-4-yl, 1H-pyrrolo[2,3-b]pyridin-4-yl, 5H-pyrrolo[3,2-d]pyrimidin-2-yl or 3H-imidazo[4,5-c]pyridin-7-yl and $R^{1a}$ is methyl, $R^{1b}$ is hydrogen and the carbon to which $R^{1a}$ and $R^{1b}$ attached is in the S configuration.

In an embodiment there is provided a compound according to formula I wherein $R^{1a}$ and $R^a$ are hydrogen or $C_{1-6}$ alkyl and $R^{1b}$ is hydrogen. In another embodiment, A is selected from 1H-pyrrolo[3,2-b]pyridin-5-yl, 1H-pyrrolo[2,3-c]pyridin-5-yl, 1H-pyrrolo[2,3-b]pyridin-5-yl, 1H-pyrrolo[2,3-c]pyridin-4-yl, 1H-pyrrolo[2,3-b]pyridin-4-yl, 5H-pyrrolo[3,2-d]pyrimidin-2-yl or 3H-imidazo[4,5-c]pyridin-7-yl and $R^{1a}$ is hydrogen or $C_{1-6}$ alkyl, $R^{1b}$ is hydrogen and r is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are (i) independently hydrogen or $C_{1-3}$ alkyl or (ii) together with the nitrogen to which they are attached form a pyrrolidine, piperidine or azetidine ring, (c) $C_{3-7}$ cycloalkyl or (d) a 4 to 7 member heterocycle containing O or $NR^e$ wherein $R^e$ is hydrogen of $C_{1-3}$ alkyl.

In an embodiment there is provided a compound according to formula I wherein $R^{1a}$ and $R^a$ are hydrogen or $C_{1-6}$ alkyl and $R^{1b}$ is hydrogen. In another embodiment, A is selected from 1H-pyrrolo[3,2-b]pyridin-5-yl, 1H-pyrrolo[2,3-c]pyridin-5-yl, 1H-pyrrolo[2,3-b]pyridin-5-yl, 1H-pyrrolo[2,3-c]pyridin-4-yl, 1H-pyrrolo[2,3-b]pyridin-4-yl, 5H-pyrrolo[3,2-d]pyrimidin-2-yl or 3H-imidazo[4,5-c]pyridin-7-yl and $R^{1a}$ is hydrogen or $C_{1-6}$ alkyl, $R^{1b}$ is hydrogen and $R^a$ is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are (i) independently hydrogen or $C_{1-3}$ alkyl In an embodiment there is provided a compound according to formula I wherein $R^{1a}$ and $R^a$ are hydrogen or $C_{1-6}$ alkyl and $R^{1b}$ is hydrogen. In another embodiment, A is selected from 1H-pyrrolo[3,2-b]pyridin-5-yl, 1H-pyrrolo[2,3-c]pyridin-5-yl, 1H-pyrrolo[2,3-b]pyridin-5-yl, 1H-pyrrolo[2,3-c]pyridin-4-yl, 1H-pyrrolo[2,3-b]pyridin-4-yl, 5H-pyrrolo[3,2-d]pyrimidin-2-yl or 3H-imidazo[4,5-c]pyridin-7-yl and $R^h$ is hydrogen or $C_{1-6}$ alkyl, $R^{1b}$ is hydrogen and $R^a$ is $C_{3-7}$ cycloalkyl.

In an embodiment there is provided a compound according to formula I wherein $R^{1a}$ and $R^a$ are hydrogen or $C_{1-6}$ alkyl and $R^{1b}$ is hydrogen. In another embodiment, A is selected from 1H-pyrrolo[3,2-b]pyridin-5-yl, 1H-pyrrolo[2,3-c]pyridin-5-yl, 1H-pyrrolo[2,3-b]pyridin-5-yl, 1H-pyrrolo[2,3-c]pyridin-4-yl, 1H-pyrrolo[2,3-b]pyridin-4-yl, 5H-pyrrolo[3,2-d]pyrimidin-2-yl or 3H-imidazo[4,5-c]pyridin-7-yl and $R^{1a}$ is hydrogen or $C_{1-6}$ alkyl, $R^{1b}$ is hydrogen and $R^a$ is a 4 to 7 member heterocycle containing O or $NR^e$ wherein $R^e$ is hydrogen of $C_{1-3}$ alkyl.

In an embodiment there is provided a compound according to formula I wherein A is substituted by at least one halogen, $C_{1-6}$ alkyl or $C_{1-6}$ alkoxy. In another embodiment, A is selected from 1H-pyrrolo[3,2-b]pyridin-5-yl, 1H-pyrrolo[2,3-c]pyridin-5-yl, 1H-pyrrolo[2,3-b]pyridin-5-yl, 1H-pyrrolo[2,3-c]pyridin-4-yl, 1H-pyrrolo[2,3-b]pyridin-4-yl, 5H-pyrrolo[3,2-d]pyrimidin-2-yl or 3H-imidazo[4,5-c]pyridin-7-yl and A is substituted by halogen, $C_{1-6}$ alkyl or $C_{1-6}$ alkoxy.

In an embodiment there is provided a compound according to formula I wherein $R^6$ is optionally substituted cycloalkyl. In another embodiment, A is selected from 1H-pyrrolo[3,2- b]pyridin-5-yl, 1H-pyrrolo[2,3-c]pyridin-5-yl, 1H-pyrrolo[2,3-b]pyridin-5-yl, 1H-pyrrolo[2,3-c]pyridin-4-yl, 1H-pyrrolo[2,3-b]pyridin-4-yl, 5H-pyrrolo[3,2-d]pyrimidin-2-yl or 3H-imidazo[4,5-c]pyridin-7-yl and $R^6$ is optionally substituted cycloalkyl.

In an embodiment there is provided a compound according to formula I wherein $R^6$ is cyclopropyl substituted by at least one fluorine atom. In another embodiment, A is selected from 1H-pyrrolo[3,2-b]pyridin-5-yl, 1H-pyrrolo[2,3-c]pyridin-5-yl, 1H-pyrrolo[2,3-b]pyridin-5-yl, 1H-pyrrolo[2,3-c]pyridin-4-yl, 1H-pyrrolo[2,3-b]pyridin-4-yl, 5H-pyrrolo[3,2-d]pyrimidin-2-yl or 3H-imidazo[4,5-c]pyridin-7-yl and $R^6$ is cyclopropyl substituted by at least one fluorine atom.

In an embodiment there is provided a compound according to formula I wherein $R^a$ and $R^{1a}$ are hydrogen or $C_{1-6}$ alkyl and $R^{1b}$ is hydrogen and $R^6$ is cyclopropyl substituted by at least one fluorine atom. In another embodiment, A is selected from 1H-pyrrolo[3,2-b]pyridin-5-yl, 1H-pyrrolo[2,3-c]pyridin-5-yl, 1H-pyrrolo[2,3-b]pyridin-5-yl, 1H-pyrrolo[2,3-c]pyridin-4-yl, 1H-pyrrolo[2,3-b]pyridin-4-yl, 5H-pyrrolo[3,2-d]pyrimidin-2-yl or 3H-imidazo[4,5-c]pyridin-7-yl and $R^{1a}$ is hydrogen or $C_{1-6}$ alkyl and $R^{1b}$ is hydrogen, $R^a$ is (a) hydrogen, (b) $C_{1-6}$ alkyl optionally substituted by one or two groups selected from the group consisting of hydroxyl, $C_{1-3}$ alkoxy or $NR^cR^d$ wherein $R^c$ and $R^d$ are (i) independently hydrogen or $C_{1-3}$ alkyl or (ii) together with the nitrogen to which they are attached form a pyrrolidine, piperidine or azetidine ring, (c) $C_{3-7}$ cycloalkyl or (d) a 4 to 7 member heterocycle containing O or $NR^e$ wherein $R^e$ is hydrogen of $C_{1-3}$ alkyl and $R^6$ is cyclopropyl substituted by at least one fluorine atom.

In an embodiment of the present invention there is provided a compound according to formula I wherein A is A-3, $X^2$ is N and $X^1$ and $X^3$ are independently $CR^2$, $R^a$ and $R^{1a}$ are hydrogen or $C_{1-6}$ alkyl and $R^{1b}$ is hydrogen, $R^a$ is hydrogen or $C_{1-6}$ alkyl and $R^6$ is cyclopropyl substituted by at least one fluorine atom. In a subembodiment $CR^2$ is CH (A is 3H-imidazo[4,5-c]pyridin-6-yl). In another subembodiment $R^{1a}$ is hydrogen or $C_{1-6}$ alkyl and $R^{1b}$ is hydrogen, $R^a$ is hydrogen or $C_{1-6}$ alkyl and $R^6$ is cyclopropyl substituted by at least one fluorine atom.

In an embodiment of the present invention there is provided a compound according to formula I wherein A is A-2, $X^2$ and Z are N, $X^1$ and $X^3$ are $CR^2$. In a subembodiment $CR^2$ is CH (i.e., A is 1H-pyrazolo[3,4-c]pyridin-4-yl). In another subembodiment A is 1H-pyrazolo[3,4-c]pyridin-4-yl, $R^{1a}$ is hydrogen or $C_{1-6}$ alkyl, $R^{1b}$ is hydrogen $R^a$ is (a) hydrogen, (b) $C_{1-6}$ alkyl optionally substituted by one or two groups selected from the group consisting of hydroxyl, $C_{1-3}$ alkoxy or $NR^cR^d$ wherein $R^c$ and $R^d$ are (i) independently hydrogen or $C_{1-3}$ alkyl or (ii) together with the nitrogen to which they are attached form a pyrrolidine, piperidine or azetidine ring, (c) $C_{3-7}$ cycloalkyl or (d) a 4 to 7 member heterocycle containing O or $NR^e$ wherein $R^e$ is hydrogen of $C_{1-3}$ alkyl and $R^6$ is cyclopropyl substituted by at least one fluorine atom.

In another embodiment of the present invention there is provided a compound selected from compounds I-1 to I-36 of TABLE I or a pharmaceutically acceptable salt thereof. In yet another embodiment of the present invention there is provided a compound selected from compounds I-1 to I-46 of TABLE I or a pharmaceutically acceptable salt thereof.

In another embodiment of the present invention there is provided a method for inhibiting PAK1 activity in a cell comprising treating the cell with a compound according to formula I wherein A, $R^{1a}$, $R^{1b}$, $R^2$, $R^3$, $R^4$, $R^5$, $R^6$, $R^7$, $R^8$, $R^a$, $R^b$, $X^1$, $X^2$ and $X^3$ are as defined herein above.

In another embodiment of the present invention there is provided a method for inhibiting PAK activity in a cell comprising treating the cell with a compound according to formula I wherein A, $R^{1a}$, $R^{1b}$, $R^2$, $R^3$, $R^4$, $R^5$, $R^6$, $R^7$, $R^8$, $R^a$, $R^b$, $X^1$, $X^2$ and $X^3$ are as defined herein above.

In another embodiment of the present invention there is provided a method for inhibiting PAK activity in a patient in need thereof comprising administering a compound according to formula I wherein A, $R^1$, $R^{1b}$, $R^2$, $R^3$, $R^4$, $R^5$, $R^6$, $R^7$, $R^8$, $R^a$, $R^b$, $X^1$, $X^2$ and $X^3$ are as defined herein above.

In another embodiment of the present invention there is provided a method of treating or ameliorating the severity of cancer or a hyperproliferative disorder in a patient in need thereof comprising administering a compound according to formula I wherein A, $R^{1a}$, $R^{1b}$, $R^2$, $R^3$, $R^4$, $R^5$, $R^6$, $R^7$, $R^8$, $R^a$, $R^b$, $X^1$, $X^2$ and $X^3$ are as defined herein above.

In another embodiment of the present invention there is provided a method of treating or ameliorating the severity of cancer or a hyperproliferative disorder in a patient in need thereof herein said cancer or hyperproliferative disorder is selected from the group consisting of adenoma, bladder cancer, brain cancer, breast cancer, colon cancer, epidermal carcinoma, follicular carcinoma, cancer of the genitourinary tract, glioblastoma, Hodgkin's disease, head and neck cancers, heptoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma comprising administering a compound according to formula I wherein A, $R^{1a}$, $R^{1b}$, $R^2$, $R^3$, $R^4$, $R^5$, $R^6$, $R^7$, $R^8$, $R^a$, $R^b$, $X^1$, $X^2$ and $X^3$ are as defined herein above.

In another embodiment of the present invention there is provided a method of treating or ameliorating the severity of cancer or a hyperproliferative disorder in a patient in need thereof wherein said cancer or hyperproliferative disorder is selected from the group consisting of lung cancer, breast cancer, ovarian cancer, bladder cancer and head and neck cancer comprising administering a compound according to formula I wherein A, $R^1$, $R^{1a}$, $R^{1b}$, $R^2$, $R^3$, $R^4$, $R^5$, $R^6$, $R^7$, $R^8$, $R^a$, $R^b$, $X^1$, $X^2$ and $X^3$ are as defined herein above.

In another embodiment of the present invention there is provided a method of treating or ameliorating the severity of cancer or a hyperproliferative disorder in a patient in need thereof wherein said cancer or hyperproliferative disorder is selected from the group consisting primary breast adenocarcinoma, squamous non-small cell lung cancer or a squamous head and neck cancer comprising administering a compound according to formula I wherein A, $R^{1a}$, $R^{1b}$, $R^2$, $R^3$, $R^4$, $R^5$, $R^6$, $R^7$, $R^8$, $R^a$, $R^b$, $X^1$, $X^2$ and $X^3$ are as defined herein above.

In another embodiment of the present invention there is provided a method of treating or ameliorating the severity of cancer or a hyperproliferative disorder in a patient in need thereof comprising co-administering a compound according to formula I wherein A, $R^{1a}$, $R^{1b}$, $R^2$, $R^3$, $R^4$, $R^5$, $R^6$, $R^7$, $R^8$, $R^a$, $R^b$, $X^1$, $X^2$ and $X^3$ are as defined herein above with at least one other chemotherapeutic agent used to treat or ameliorate cancer or a hyperproliferative disorder.

In another embodiment of the present invention there is provided a method of treating or ameliorating the severity of cancer or a hyperproliferative disorder in a patient in need thereof comprising co-administering a compound according to formula I wherein A, $R^{1a}$, $R^{1b}$, $R^2$, $R^3$, $R^4$, $R^5$, $R^6$, $R^7$, $R^8$, $R^a$, $R^b$, $X^1$, $X^2$ and $X^3$ are as defined herein above and a chemotherapeutic agent is selected from the group consisting of inhibitor of apoptosis proteins (IAP), an EGFR inhibitor or antagonist, an inhibitor of Ras/Raf/Mek/Erk signaling cascade, an inhibitor of Akt kinase and a Src kinase inhibitor.

In another embodiment of the present invention there is provided a compound according to formula I wherein A, $R^{1a}$, $R^{1b}$, $R^2$, $R^3$, $R^4$, $R^5$, $R^6$, $R^7$, $R^8$, $R^a$, $R^b$, $X^1$, $X^2$ and $X^3$ are as defined hereinabove and at least one pharmaceutically acceptable carrier, excipient or diluent.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include *Goodman and Gilman's The Pharmacological Basis of Therapeutics,* 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as Fieser and Fieser's *Reagents for Organic Synthesis*; Wiley & Sons: New York, Volumes 1-21; R. C. Larock, Comprehensive Organic Transformations, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted by at least one substituent selected from the other specifically-named group. Thus, for example, "phenylalkyl" refers to an alkyl group having one to two phenyl substituents, and thus includes benzyl(phenylmethyl) and phenylethyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to a moiety that is either an aryl or a heteroaryl group.

The term "alkyl" as used herein without further limitation, alone or in combination with other groups, denotes an unbranched or branched chain, saturated, monovalent hydrocarbon residue containing 1 to 10 carbon atoms, for example, methyl, ethyl, propyl, isopropyl, n-butyl, iso-butyl, sec-butyl, or tert-butyl. The term "lower alkyl" denotes a straight or branched chain hydrocarbon residue containing 1 to 6 carbon atoms. "$C_{1-6}$ alkyl" as used herein refers to an alkyl composed of 1 to 6 carbons.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having one (e.g., a spirocycle) two or more carbon atoms in common. For example, "$C_{3-7}$ cycloalkyl" as used herein refers to a cycloalkyl composed of 3 to 7 carbons in the carbocyclic ring. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "cycloalkylalkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cyclolalkyl and R" is $C_{1-3}$ alkylene as defined herein.

The term "alkoxy" as used herein means an —O-alkyl group, wherein alkyl is as defined above such as methoxy, ethoxy, n-propyloxy, iso-propyloxy, n-butyloxy, iso-butyloxy, tert-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "acyl", "alkanoyl" or "alkylcarbonyl" denotes a group of the formula —C(O)—R in which R is hydrogen or alkyl as defined above. The term $C_{1-6}$ acyl [or "alkanoyl"] refers to a group —C(=O)R contain 1 to 6 carbon atoms. The $C_1$ acyl or "alkanoyl" is the formyl group wherein R=H and a $C_6$ acyl group refers to hexanoyl when the alkyl chain is unbranched. The term "arylcarbonyl" or "aroyl" as used herein means a group of formula C(=O)R wherein R is an aryl group; the term "benzoyl" as used herein an "arylcarbonyl" or "aroyl" group wherein R is phenyl.

The terms "alkoxycarbonyl" and "aryloxycarbonyl" as used herein denotes a group of formula C(=O)OR wherein R is alkyl or aryl respectively and alkyl and aryl are as defined herein.

The term "haloalkoxy" as used herein refers to a group —OR where R is haloalkyl as defined herein. Examples of haloalkoxyl include monofluoro-, difluoro- or trifluoro-methoxy, -ethoxy or propoxy, for example 3,3,3-trifluoropropoxy, 2-fluoroethoxy, 2,2,2-trifluoroethoxy, fluoromethoxy, or trifluoromethoxy. The term "haloalkylthio" as used herein refers to a group —SR where R is haloalkyl as defined herein.

The term "haloalkanoyl" refers to an alkanoyl group wherein at least one of the hydrogen atoms of the alkyl group has been replaced by same or different halogen atoms, The term "halo", "halogen", and "halide" are used interchangeably herein and denote fluoro, chloro, bromo, or iodo.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. "$C_{0-4}$ alkylene" refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "heterocyclyl" or "heterocycle" as used herein denotes a monovalent saturated cyclic radical, consisting of one or more rings, preferably one to two rings, of three to eight atoms per ring, incorporating one or more ring heteroatoms (chosen from N, O or $S(=O)_{0-2}$) with the remaining ring atoms being carbon, with the understanding that the attachment point of the heteroaryl radical will be on a carbon atom. The heterocyclyl moiety can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamido, arylsulfonylamido, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The terms "treat" and "treatment" refer to therapeutic treatment wherein the object is to slow down (lessen) an undesired physiological change or disorder, such as the spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors;

(viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The following names are used in the specification: (i) 1H-pyrrolo[3,2-b]pyridin-5-yl, (ii) 1H-pyrrolo[2,3-c]pyridin-5-yl, (iii) 1H-pyrrolo[2,3-b]pyridin-5-yl, (iv) 1H-pyrrolo[3,2-c]pyridin-4-yl, (v) 1H-pyrrolo[2,3-c]pyridin-4-yl, (vi) 1H-pyrrolo[2,3-b]pyridin-4-yl, (vii) 5H-pyrrolo[3,2-d]pyrimidin-2-yl), (viii) 3H-imidazo[4,5-c]pyridin-7-yl, (ix) 3H-imidazo[4,5-c]pyridin-6-yl or (x) 1H-pyrazolo[3,4-c]pyridin-4-yl.

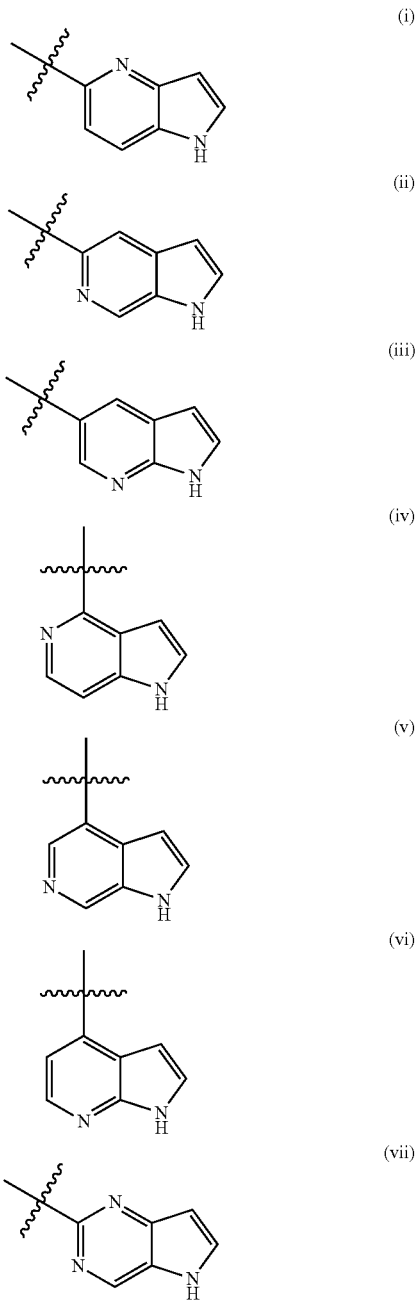

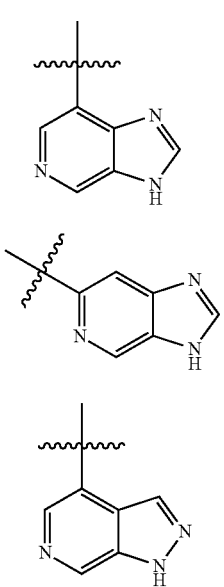

Commonly used abbreviations include: acetyl (Ac), aqueous (aq.), atmospheres (Atm), tert-butoxycarbonyl (Boc), di-tert-butyl pyrocarbonate or boc anhydride (BOC$_2$O), benzyl (Bn), benzotriazol-1-yloxy-tris-(dimethylamino)phosphonium hexafluorophosphate (BOP), butyl (Bu), benzoyl (Bz), Chemical Abstracts Registration Number (CASRN), benzyloxycarbonyl (CBZ or Z), carbonyl diimidazole (CDI), dibenzylideneacetone (DBA), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCl), ethyl (Et), ethyl acetate (EtOAc), ethanol (EtOH), 2-ethoxy-2H-quinoline-1-carboxylic acid ethyl ester (EEDQ), diethyl ether (Et$_2$O), 0-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IA), methanol (MeOH), melting point (mp), MeSO$_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), petroleum ether (pet ether, i.e. hydrocarbons)) phenyl (Ph), propyl (Pr), iso-propyl (i-Pr), pounds per square inch (psi), bromo-tris-pyrrolidinophosphonium hexafluorophosphate (PyBrOP), pyridine (pyr), room temperature (rt or RT), satd. (saturated), tert-butyldimethylsilyl or t-BuMe$_2$Si (TBDMS), triethylamine (TEA or Et$_3$N), triflate or CF$_3$SO$_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or Me$_3$Si (TMS), 2-(trimethylsilyl)ethoxymethyl (SEM), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert- or -t) and neo- have their customary meaning when used with an alkyl moiety. (J. Rigaudy and D. P. Klesney, Nomenclature in Organic Chemistry, IUPAC 1979 Pergamon Press, Oxford).

Compounds and Preparation

Examples of representative compounds within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. The following numbering system is used herein.

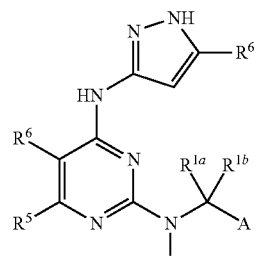

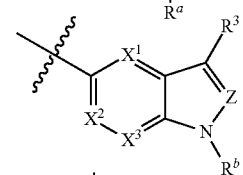

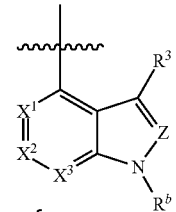

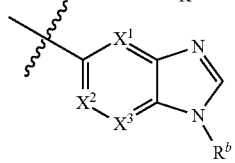

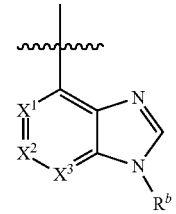

TABLE I

| Ex. No. | Structure | MS | Name |
|---|---|---|---|
| I-1 | 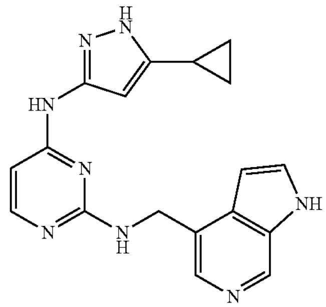 [SMILES: c1cc(Nc2cc(C3CC3)[nH]n2)nc(NCc2cncc3[nH]ccc23)n1] | 347.2 | $N^4$-(5-Cyclopropyl-1H-pyrazol-3-yl)-$N^2$-(1H-pyrrolo[2,3-c]pyridin-4-ylmethyl)-pyrimidine-2,4-diamine |
| I-2 | 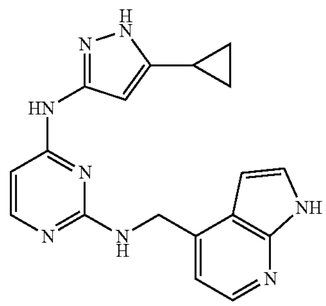 [SMILES: c1cc(Nc2cc(C3CC3)[nH]n2)nc(NCc2ccnc3[nH]ccc23)n1] | 347.2 | $N^4$-(5-Cyclopropyl-1H-pyrazol-3-yl)-$N^2$-(1H-pyrrolo[2,3-b]pyridin-4-ylmethyl)-pyrimidine-2,4-diamine |
| I-3 | HCO$_2$H | 347.2 | $N^4$-(5-Cyclopropyl-1H-pyrazol-3-yl)-$N^2$-(1H-pyrrolo[3,2-c]pyridin-4-ylmethyl)-pyrimidine-2,4-diamine |
| I-4 | 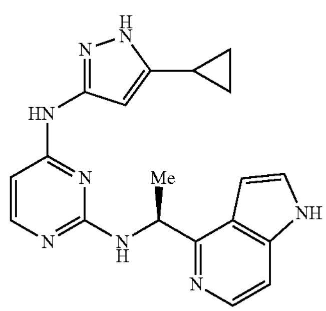 [SMILES: C[C@H](Nc1nccc(Nc2cc(C3CC3)[nH]n2)n1)c1nccc2[nH]ccc12] | 361.2 | $N^4$-(5-Cyclopropyl-1H-pyrazol-3-yl)-$N^2$-[1-(1H-pyrrolo[3,2-c]pyridin-4-yl)-ethyl]-pyrimidine-2,4-diamine |
| I-5 | 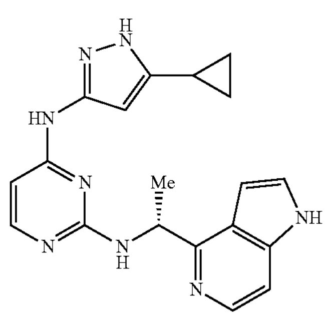 [SMILES: C[C@@H](Nc1nccc(Nc2cc(C3CC3)[nH]n2)n1)c1nccc2[nH]ccc12] | 361.2 | $N^4$-(5-Cyclopropyl-1H-pyrazol-3-yl)-$N^2$-[1-(1H-pyrrolo[3,2-c]pyridin-4-yl)-ethyl]-pyrimidine-2,4-diamine |

TABLE I-continued

| Ex. No. | Structure | MS | Name |
|---|---|---|---|
| I-6 | 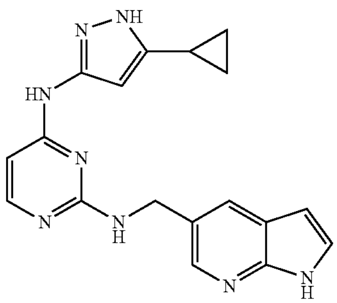 [SMILES: c1cc(Nc2cc(C3CC3)[nH]n2)nc(NCc2cnc3[nH]ccc3c2)n1] | 347.2 | $N^4$-(5-Cyclopropyl-1H-pyrazol-3-yl)-$N^2$-[1-(5H-pyrrolo[3,2-d]pyrimidin-2-yl)-ethyl]-pyrimidine-2,4-diamine |
| I-7 | 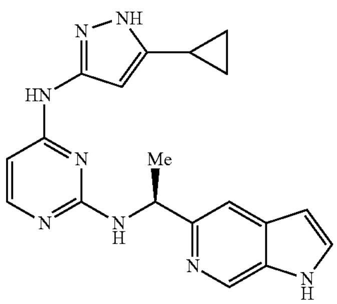 [SMILES: C[C@H](Nc1nccc(Nc2cc(C3CC3)[nH]n2)n1)c1cc2cc[nH]c2cn1] | 361.2 | $N^4$-(5-Cyclopropyl-1H-pyrazol-3-yl)-$N^2$-[1-(1H-pyrrolo[2,3-c]pyridin-5-yl)-ethyl]-pyrimidine-2,4-diamine |
| I-8 | 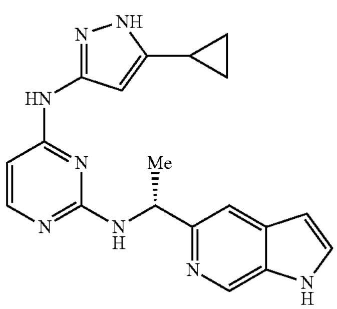 [SMILES: C[C@@H](Nc1nccc(Nc2cc(C3CC3)[nH]n2)n1)c1cc2cc[nH]c2cn1] | 361.2 | $N^4$-(5-Cyclopropyl-1H-pyrazol-3-yl)-$N^2$-[1-(1H-pyrrolo[2,3-c]pyridin-5-yl)-ethyl]-pyrimidine-2,4-diamine |
| I-9 | 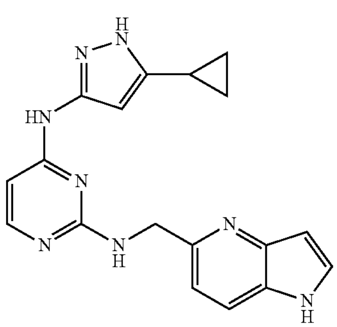 [SMILES: c1cc(Nc2cc(C3CC3)[nH]n2)nc(NCc2ccc3[nH]ccc3n2)n1] | 347 | $N^4$-(5-Cyclopropyl-1H-pyrazol-3-yl)-$N^2$-(1H-pyrrolo[3,2-b]pyridin-5-ylmethyl)-pyrimidine-2,4-diamine |
| I-10 | 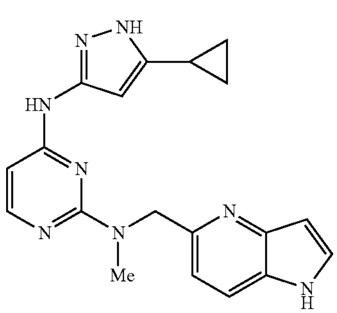 [SMILES: CN(Cc1ccc2[nH]ccc2n1)c1nccc(Nc2cc(C3CC3)[nH]n2)n1] | 361.3 | $N^4$-(5-Cyclopropyl-1H-pyrazol-3-yl)-$N^2$-methyl-$N^2$-(1H-pyrrolo[3,2-b]pyridin-5-ylmethyl)-pyrimidine-2,4-diamine |

TABLE I-continued

| Ex. No. | Structure | MS | Name |
|---|---|---|---|
| I-11 | 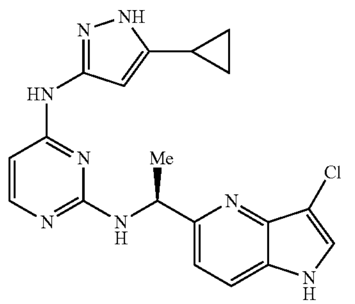 [SMILES: C[C@H](Nc1nccc(Nc2cc(C3CC3)[nH]n2)n1)c1ccc2[nH]cc(Cl)c2n1] | 395.1 | $N^4$-[1-(3-Chloro-1H-pyrrolo[3,2-b]pyridin-5-yl)-ethyl]-$N^4$-(5-cyclopropyl-1H-pyrazol-3-yl)-pyrimidine-2,4-diamine |
| I-12 | 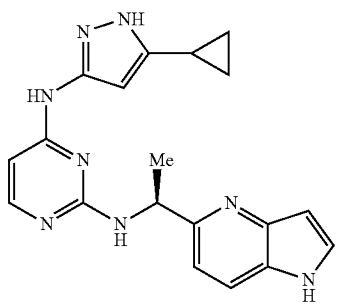 [SMILES: C[C@H](Nc1nccc(Nc2cc(C3CC3)[nH]n2)n1)c1ccc2[nH]ccc2n1] | 361.3 | $N^4$-(5-Cyclopropyl-1H-pyrazol-3-yl)-$N^2$-[(S)-1-(1H-pyrrolo[3,2-b]pyridin-5-yl)-ethyl]-pyrimidine-2,4-diamine |
| I-13 | 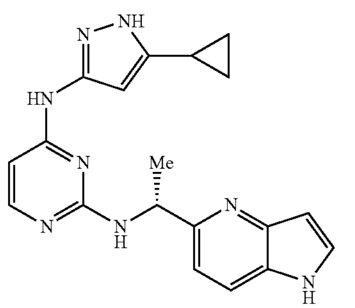 [SMILES: C[C@@H](Nc1nccc(Nc2cc(C3CC3)[nH]n2)n1)c1ccc2[nH]ccc2n1] | 361.3 | $N^4$-(5-Cyclopropyl-1H-pyrazol-3-yl)-$N^2$-[(R)-1-(1H-pyrrolo[3,2-b]pyridin-5-yl)-ethyl]-pyrimidine-2,4-diamine |
| I-14 | 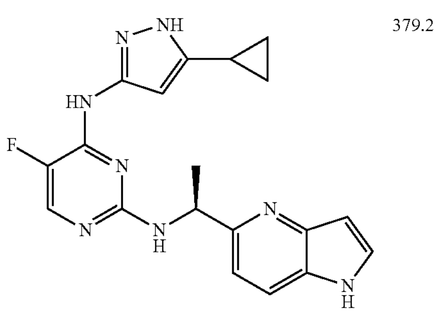 | 379.2 | $N^4$-(5-Cyclopropyl-1H-pyrazol-3-yl)-5-fluoro-$N^2$-[(S)-1-(1H-pyrrolo[3,2-b]pyridin-5-yl)-ethyl]-pyrimidine-2,4-diamine |
| I-15 | 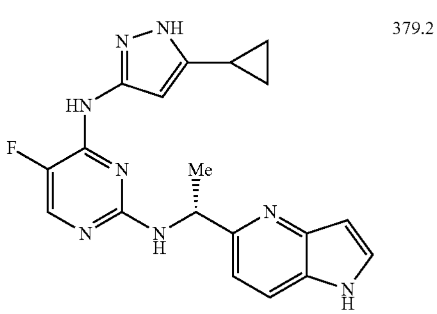 | 379.2 | $N^4$-(5-Cyclopropyl-1H-pyrazol-3-yl)-5-fluoro-$N^2$-[(R)-1-(1H-pyrrolo[3,2-b]pyridin-5-yl)-ethyl]-pyrimidine-2,4-diamine |

TABLE I-continued

| Ex. No. | Structure | MS | Name |
|---|---|---|---|
| I-16 | 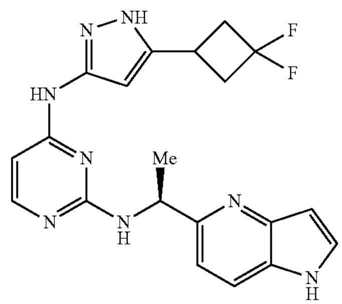 [SMILES: C[C@H](Nc1nccc(Nc2cc(C3CC(F)(F)C3)[nH]n2)n1)c1ccc2[nH]ccc2n1] | 411.1 | $N^4$-[5-(3,3-Difluoro-cyclobutyl)-1H-pyrazol-3-yl]-$N^2$-[(S)-1-(1H-pyrrolo[3,2-b]pyridin-5-yl)-ethyl]-pyrimidine-2,4-diamine |
| I-17 | 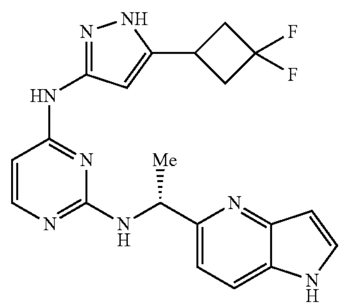 [SMILES: C[C@@H](Nc1nccc(Nc2cc(C3CC(F)(F)C3)[nH]n2)n1)c1ccc2[nH]ccc2n1] | 411.1 | $N^4$-[5-(3,3-Difluoro-cyclobutyl)-1H-pyrazol-3-yl]-$N^2$-[(R)-1-(1H-pyrrolo[3,2-b]pyridin-5-yl)-ethyl]-pyrimidine-2,4-diamine |
| I-18 | 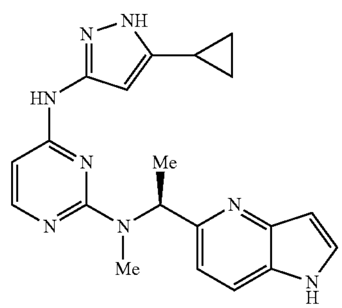 [SMILES: C[C@@H](c1ccc2[nH]ccc2n1)N(C)c1nccc(Nc2cc(C3CC3)[nH]n2)n1] | 375.2 | $N^4$-(5-Cyclopropyl-1H-pyrazol-3-yl)-$N^2$-methyl-$N^2$-[(S)-1-(1H-pyrrolo[3,2-b]pyridin-5-yl)-ethyl]-pyrimidine-2,4-diamine |
| I-19 | 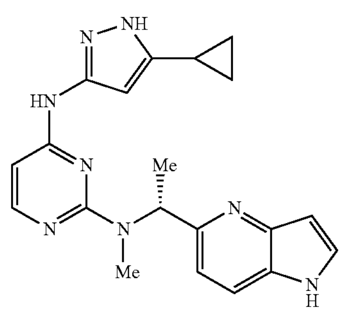 [SMILES: C[C@H](c1ccc2[nH]ccc2n1)N(C)c1nccc(Nc2cc(C3CC3)[nH]n2)n1] | 375.2 | $N^4$-(5-Cyclopropyl-1H-pyrazol-3-yl)-$N^2$-methyl-$N^2$-[(R)-1-(1H-pyrrolo[3,2-b]pyridin-5-yl)-ethyl]-pyrimidine-2,4-diamine |
| I-20 | 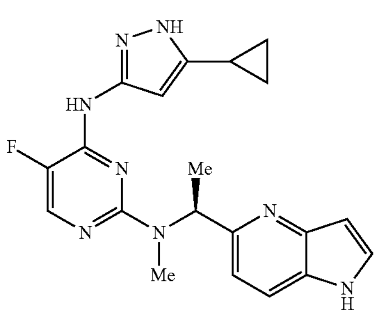 [SMILES: C[C@@H](c1ccc2[nH]ccc2n1)N(C)c1ncc(F)c(Nc2cc(C3CC3)[nH]n2)n1] | 393.1 | $N^4$-(5-Cyclopropyl-1H-pyrazol-3-yl)-5-fluoro-$N^2$-methyl-$N^2$-[(S)-1-(1H-pyrrolo[3,2-b]pyridin-5-yl)-ethyl]-pyrimidine-2,4-diamine |

TABLE I-continued

| Ex. No. | Structure | MS | Name |
|---|---|---|---|
| I-21 | 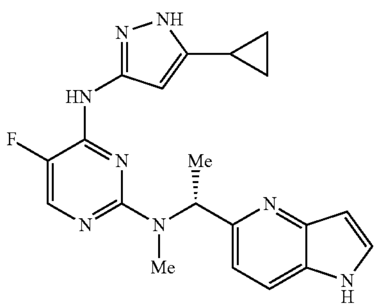 [SMILES: C[C@H](c1ccc2[nH]ccc2n1)N(C)c1ncc(F)c(Nc2cc(C3CC3)[nH]n2)n1] | 393.1 | N4-(5-Cyclopropyl-1H-pyrazol-3-yl)-5-fluoro-N2-methyl-N2-[(R)-1-(1H-pyrrolo[3,2-b]pyridin-5-yl)-ethyl]-pyrimidine-2,4-diamine |
| I-22 | 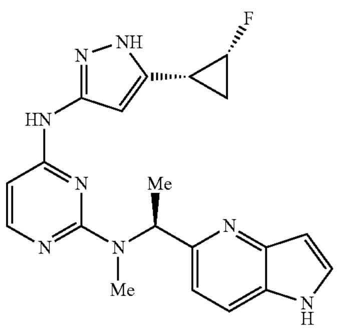 [SMILES: C[C@@H](c1ccc2[nH]ccc2n1)N(C)c1nccc(Nc2cc([C@H]3C[C@H]3F)[nH]n2)n1] | 393.1 | N4-[-5-(1R,2R)-2-Fluoro-cyclopropyl)-1H-pyrazol-3-yl]-N2-methyl-N2-[(S)-1-(1H-pyrrolo[3,2-b]pyridin-5-yl)-ethyl]-pyrimidine-2,4-diamine |
| I-23 | 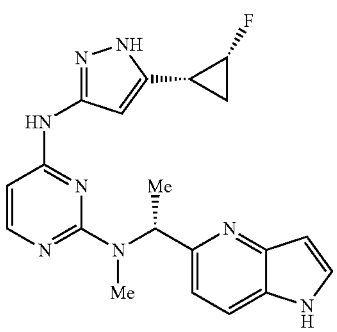 [SMILES: C[C@H](c1ccc2[nH]ccc2n1)N(C)c1nccc(Nc2cc([C@H]3C[C@H]3F)[nH]n2)n1] | 393.1 | N4-[5-((1R,2R)-2-Fluoro-cyclopropyl)-1H-pyrazol-3-yl]-N2-methyl-N2-[(R)-1-(1H-pyrrolo[3,2-b]pyridin-5-yl)-ethyl]-pyrimidine-2,4-diamine |
| I-24 | 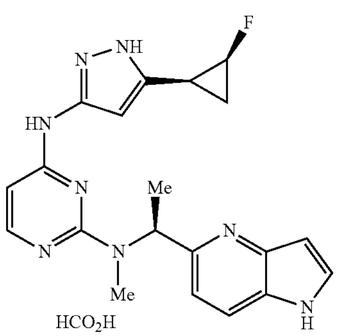 [SMILES: C[C@@H](c1ccc2[nH]ccc2n1)N(C)c1nccc(Nc2cc([C@@H]3C[C@@H]3F)[nH]n2)n1 ; "HCO2H"] | 393.2 | N4-[5-((1S,2S)-2-Fluoro-cyclopropyl)-1H-pyrazol-3-yl]-N2&-methyl-N2-[(S)-1-(1H-pyrrolo[3,2-b]pyridin-5-yl)-ethyl]-pyrimidine-2,4-diamine |

TABLE I-continued

| Ex. No. | Structure | MS | Name |
|---|---|---|---|
| I-25 | 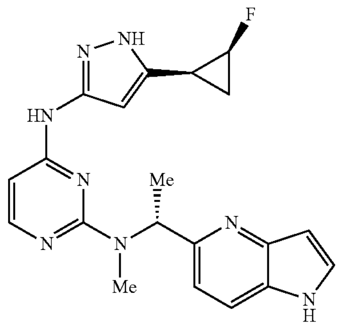 [SMILES: C[C@H](c1ccc2[nH]ccc2n1)N(C)c1nccc(Nc2cc([C@@H]3C[C@@H]3F)[nH]n2)n1] | 393.2 | $N^4$-[5-((1S,2S)-2-Fluoro-cyclopropyl)-1H-pyrazol-3-yl]-$N^2$-methyl-$N^2$-[(R)-1-(1H-ethyl]-pyrimidine-2,4-diamine |
| I-26 | 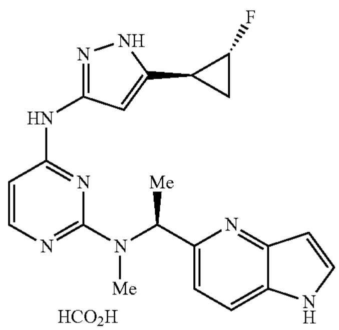 [SMILES: C[C@@H](c1ccc2[nH]ccc2n1)N(C)c1nccc(Nc2cc([C@@H]3C[C@H]3F)[nH]n2)n1 ; "HCO2H"] | 393.1 | $N^4$-[5-((1S,2R)-2-Fluoro-cyclopropyl)-1H-pyrazol-3-yl]-$N^2$-methyl-$N^2$-[(S)-1-(1H-pyrrolo[3,2-b]pyridin-5-yl)-ethyl]-pyrimidine-2,4-diamine |
| I-27 | 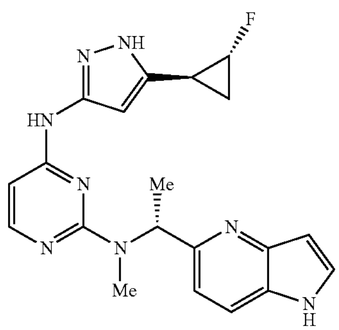 [SMILES: C[C@H](c1ccc2[nH]ccc2n1)N(C)c1nccc(Nc2cc([C@@H]3C[C@H]3F)[nH]n2)n1] | 393.1 | $N^4$-[5-((1S,2R)-2-Fluoro-cyclopropyl)-1H-pyrazol-3-yl]-$N^2$-methyl-$N^2$-[(R)-1-(1H-pyrrolo[3,2-b]pyridin-5-yl)-ethyl]-pyrimidine-2,4-diamine |
| I-28 | 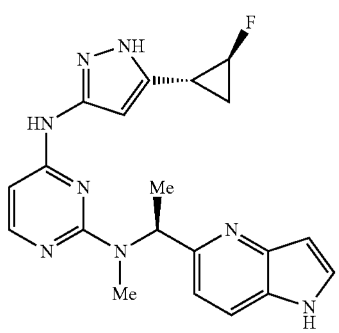 [SMILES: C[C@@H](c1ccc2[nH]ccc2n1)N(C)c1nccc(Nc2cc([C@H]3C[C@@H]3F)[nH]n2)n1] | 393.1 | $N^4$-[5-((1R,2S)-2-Fluoro-cyclopropyl)-1H-pyrazol-3-yl]-$N^2$-methyl-$N^2$-[(S)-1-(1H-pyrrolo[3,2-b]pyridin-5-yl)-ethyl]-pyrimidine-2,4-diamine |

TABLE I-continued

| Ex. No. | Structure | MS | Name |
|---|---|---|---|
| I-29 | 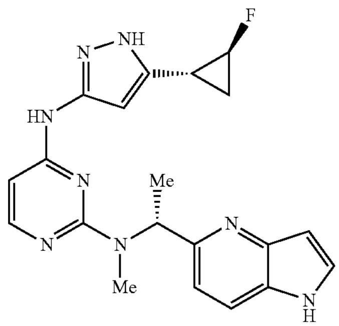 [SMILES: C[C@H](c1ccc2[nH]ccc2n1)N(C)c1nccc(Nc2cc([C@H]3C[C@@H]3F)[nH]n2)n1] | 393.1 | N⁴-[5-((1R,2S)-2-Fluoro-cyclopropyl)-1H-pyrazol-3-yl]-N²-methyl-N²-[(R)-1-(1H-pyrrolo[3,2-b]pyridin-5-yl)-ethyl]-pyrimidine-2,4-diamine |
| I-30 | 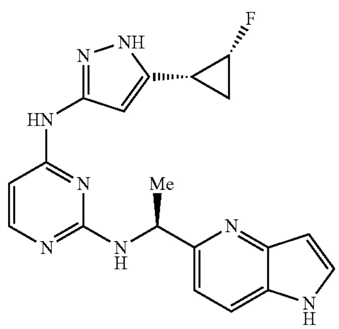 [SMILES: C[C@H](Nc1nccc(Nc2cc([C@H]3C[C@H]3F)[nH]n2)n1)c1ccc2[nH]ccc2n1] | 379.2 | N⁴-[5-((1R,2R)-2-Fluoro-cyclopropyl)-1H-pyrazol-3-yl]-N²-[(S)-1-(1H-pyrrolo[3,2-b]pyridin-5-yl)-ethyl]-pyrimidine-2,4-diamine |
| I-31 | 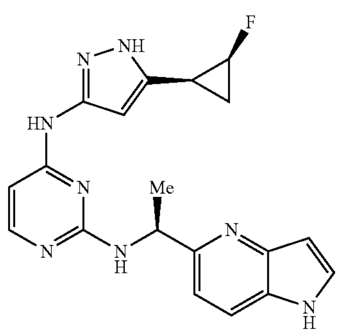 [SMILES: C[C@H](Nc1nccc(Nc2cc([C@@H]3C[C@@H]3F)[nH]n2)n1)c1ccc2[nH]ccc2n1] | 379.1 | N⁴-[5-((1S,2S)-2-Fluoro-cyclopropyl)-1H-pyrazol-3-yl]-N²-[(S)-1-(1H-pyrrolo[3,2-b]pyridin-5-yl)-ethyl]-pyrimidine-2,4-diamine |
| I-32 | 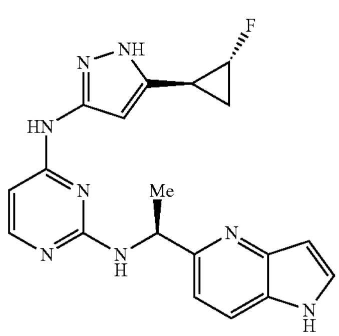 [SMILES: C[C@H](Nc1nccc(Nc2cc([C@@H]3C[C@H]3F)[nH]n2)n1)c1ccc2[nH]ccc2n1] | 379.1 | N⁴-[5-((1S,2R)-2-Fluoro-cyclopropyl)-1H-pyrazol-3-yl]-N²-[(S)-1-(1H-pyrrolo[3,2-b]pyridin-5-yl)-ethyl]-pyrimidine-2,4-diamine |

TABLE I-continued

| Ex. No. | Structure | MS | Name |
|---|---|---|---|
| I-33 | 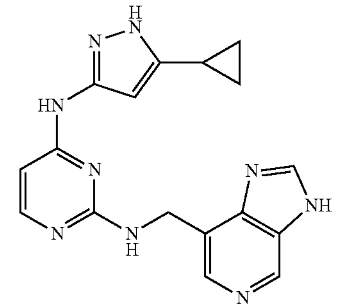 [SMILES: c1cc(Nc2cc(C3CC3)[nH]n2)nc(NCc2cncc3[nH]cnc23)n1] | 348.1 | $N^4$&-(5-Cyclopropyl-1H-pyrazol-3-yl)-$N^2$-(3H-imidazo[4,5-c]pyridin-7-ylmethyl)-pyrimidine-2,4-diamine |
| I-34 | 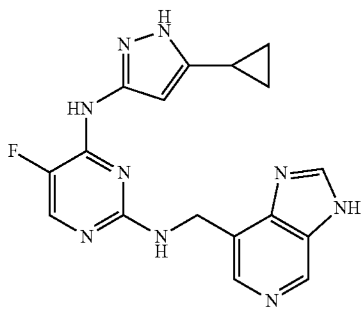 [SMILES: Fc1cnc(NCc2cncc3[nH]cnc23)nc1Nc1cc(C2CC2)[nH]n1] | 366.1 | $N^4$-(5-Cyclopropyl-1H-pyrazol-3-yl)-5-fluoro-$N^2$-(3H-imidazo[4,5-c]pyridin-7-ylmethyl)-pyrimidine-2,4-diamine |
| I-35 | 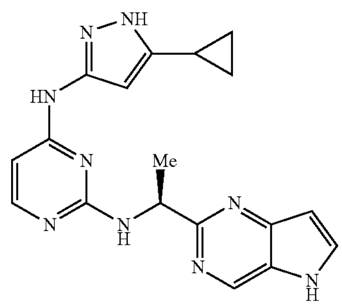 [SMILES: C[C@H](Nc1nccc(Nc2cc(C3CC3)[nH]n2)n1)c1ncc2[nH]ccc2n1] | 362.0 | (S)-$N^2$-(1-(5H-pyrrolo[3,2-d]pyrimidin-2-yl)ethyl)-$N^4$-(5-cyclopropyl-1H-pyrazol-3-yl)pyrimidine-2,4-diamine |
| I-36 | 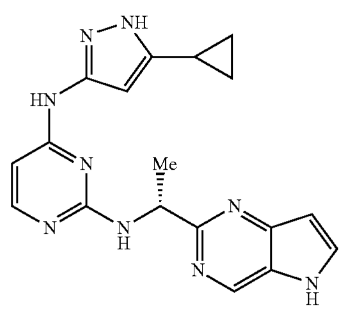 [SMILES: C[C@@H](Nc1nccc(Nc2cc(C3CC3)[nH]n2)n1)c1ncc2[nH]ccc2n1] | 362.0 | (R)-$N^2$-(1-(5H-pyrrolo[3,2-c]pyrimidin-2-yl)ethyl)-$N^4$-(5-cyclopropyl-1H-pyrazol-3-yl)pyrimidine-2,4-diamine |
| I-37 | 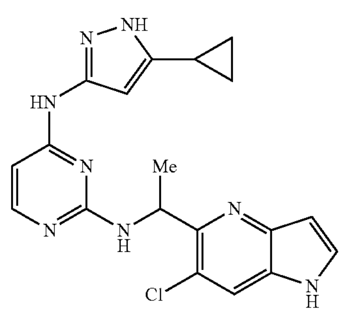 [SMILES: CC(Nc1nccc(Nc2cc(C3CC3)[nH]n2)n1)c1nc2cc[nH]c2cc1Cl] | 395.1 | $N^2$-[1-(6-chloro-1H-pyrrolo[3,2-b]pyridin-5-yl)ethyl]-$N^4$-(5-cyclopropyl-1H-pyrazol-3-yl)pyrimidine-2,4-diamine |

TABLE I-continued

| Ex. No. | Structure | MS | Name |
|---|---|---|---|
| I-38 | 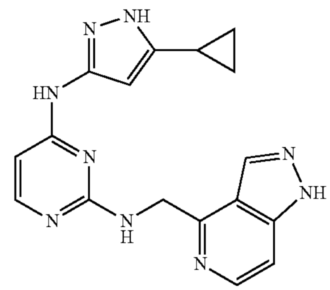 [SMILES: c1cc(Nc2cc(C3CC3)[nH]n2)nc(NCc2nccc3[nH]ncc23)n1] | 348.1 | $N^4$-(5-cyclopropyl-1H-pyrazol-3-yl)-$N^2$-(1H-pyrazolo[4,3-c]pyridin-4-ylmethyl)pyrimidine-2,4-diamine |
| I-39 | 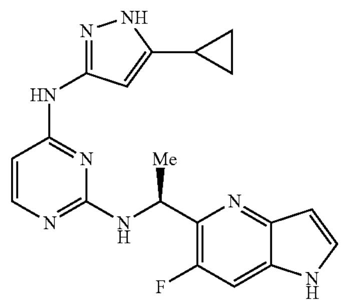 [SMILES: C[C@H](Nc1nccc(Nc2cc(C3CC3)[nH]n2)n1)c1nc2cc[nH]c2cc1F] | 379.1 | $N^4$-(5-cyclopropyl-1H-pyrazol-3-yl)-$N^2$-[(1S)-1-(6-fluoro-1H-pyrrolo[3,2-b]pyridin-5-yl)ethyl]pyrimidine-2,4-diamine |
| I-40 | 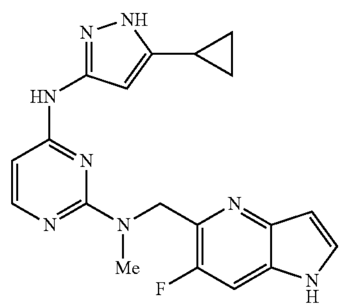 [SMILES: CN(Cc1nc2cc[nH]c2cc1F)c1nccc(Nc2cc(C3CC3)[nH]n2)n1] | 379.3 | $N^4$-(5-cyclopropyl-1H-pyrazol-3-yl)-$N^2$-[(6-fluoro-1H-pyrrolo[3,2-b]pyridin-5-yl)methyl]-$N^2$-methyl-pyrimidine-2,4-diamine |
| I-41 | 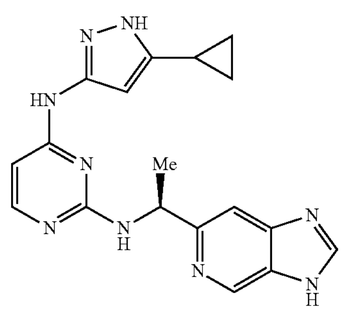 [SMILES: C[C@H](Nc1nccc(Nc2cc(C3CC3)[nH]n2)n1)c1cc2nc[nH]c2cn1] | 362.3 | (S)-$N^2$-(1-(3H-imidazo[4,5-c]pyridin-6-yl)ethyl)-$N^4$-(5-cyclopropyl-1H-pyrazol-3-ly)pyrimidine-2,4-diamine |
| I-42 | 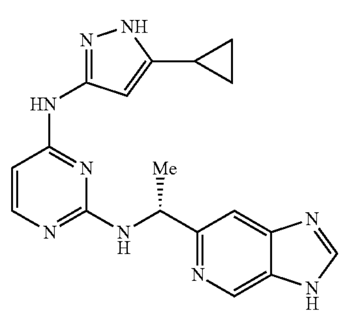 [SMILES: C[C@@H](Nc1nccc(Nc2cc(C3CC3)[nH]n2)n1)c1cc2nc[nH]c2cn1] | 362.3 | (R)-$N^2$-(1-(3H-imidazo[4,5-c]pyridin-6-yl)ethyl)-$N^4$-(5-cyclopropyl-1H-pyrazol-3-yl)pyrimidine-2,4-diamine |

TABLE I-continued

| Ex. No. | Structure | MS | Name |
|---|---|---|---|
| I-43 | 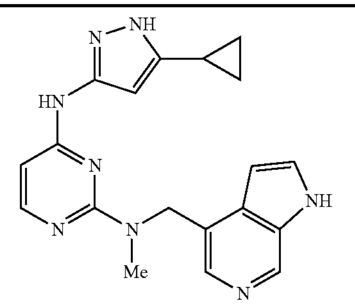 | 361.2 | $N^4$-(5-cyclopropyl-1H-pyrazol-3-yl)-$N^2$-methyl-$N^2$-(1H-pyrrolo[2,3-c]pyridin-4-ylmethyl)pyrimidine-2,4-diamine |
| I-44 | 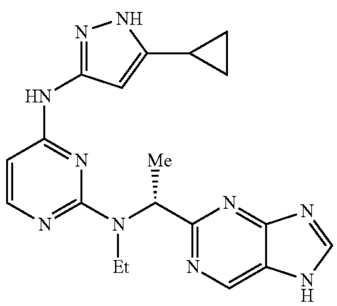 [SMILES: CCN(c1nccc(Nc2cc(C3CC3)[nH]n2)n1)[C@H](C)c1ncc2[nH]cnc2n1] | 390.1 | (R)-$N^2$-(1-(5H-pyrrolo[3,2-d]pyrimidin-2-yl)ethyl)-$N^4$-(5-cyclopropyl-1H-pyrazol-3-yl)-$N^2$-ethylpyrimidine-2,4-diamine |
| I-45 | 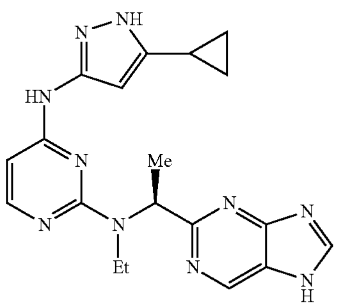 [SMILES: CCN(c1nccc(Nc2cc(C3CC3)[nH]n2)n1)[C@@H](C)c1ncc2[nH]cnc2n1] | 390.1 | (S)-$N^2$-(1-(5H-pyrrolo[3,2-d]pyrimidin-2-yl)ethyl)-$N^4$-(5-cyclopropyl-1H-pyrazol-3-yl)-$N^2$-ethylpyrimidine-2,4-diamine |
| I-46 | | 413.1 | $N^2$-[(1S)-1-(3-chloro-1H-pyrrolo[3,2-b]pyridin-5-yl)ethyl]-$N^4$-[5-[(1R,2S)-2-fluorocyclopropyl]-1H-pyrazol-3-yl]pyrimidine-2,4-diamine |

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, or, about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

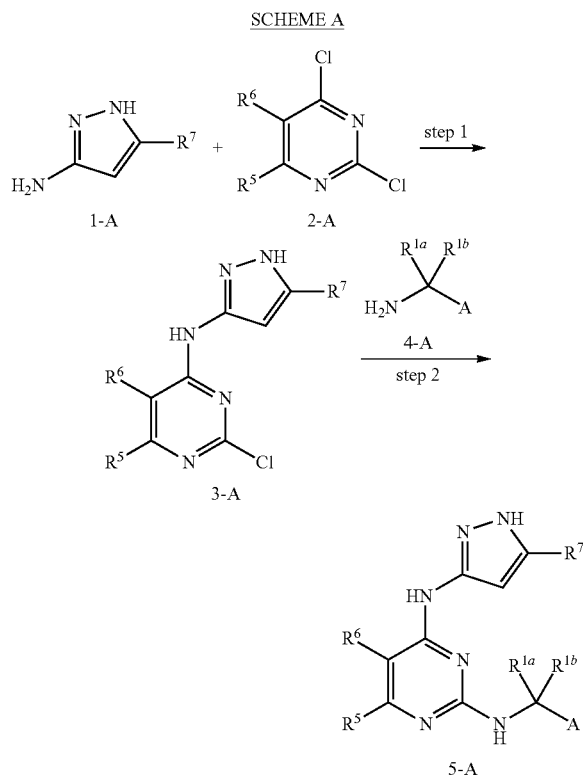

SCHEME A

Compounds of the present invention can be assembled by a two step process comprising (a) condensation of a suitably substituted pyrazole 1-A and a suitably substituted 2,4-dichloropyrimidine 2-A which results in the displacement of the more reactive 4-chloro substituent affording the pyrimidine 3-A which is subsequently condensed with an appropriate amine 4-A to afford the diamino pyrimidines 5-A of the present invention.

Step 1 is carried out by contacting 1-A and 2-A in an organic solvent in the presence of a base at temperatures sufficient to initiate the reaction. Typical bases include tertiary amines such as DIPEA, TEA, DABCO and typical solvents include EtOH or DMSO. Temperatures between 50 and 100° C. and frequently between 50 and 70° C. are adequate to maintain an acceptable reaction rate. The introduction of the amine at C-4 deactivates the ring to a subsequent displacement, thus monosubstitution is easily achieved. Introduction of 4-A is therefore carried out under analogous conditions except higher-boiling solvents such as n-BuOH or isopropanol are used and the reaction is run at a higher temperature using an thermal or a microwave heat source. Steric hindrance about the amino group in A-4 can further inhibit the reaction which may require temperatures up to 140° C. to achieve acceptable reaction rates. One skilled in the art will appreciate that it may be necessary or advantageous to incorporate protecting groups into A-4 to mask potentially competing nucleophilic sites and in such cases there will be subsequent steps to remove the protecting group.

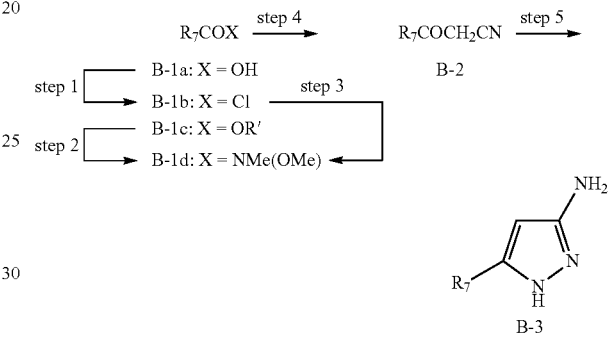

SCHEME B

5-Substituted amino-pyrazoles B-3 were prepared by contacting hydrazine and a 3-cyclopropyl-3-oxopropanenitrile derivative B-2 in EtOH at reflux temperature. The cyanoketone compounds can be prepared by deprotonation of acetonitrile and condensation of the resulting conjugate base with an acyl equivalent which can be an acyl chloride B-1b, an ester B-1c or a methoxymethylamine B-1d. Deprotonation of the nitrile can be conveniently accomplished with a variety of strong bases including, for example, n-BuLi/THF/−65° C., LiHMDS/THF/−65° C., NaH/dioxane/RT, potassium amyloxide/THF/RT. Esters and methoxymethylamides are prepared using any of the well-established protocols.

Aza-indoles used to prepare compounds of the present invention include 4-chloro-1H-pyrrolo[3,2-c]pyridine (CASRN 60290-21-3), 4-chloro-1H-pyrrolo[2,3-c]pyridine (CASRN 1188313-15-6), 4-chloro-1H-pyrrolo[2,3-b]pyridine (CASRN 55052-28-3), 4-chloro-7H-pyrrolo[2,3-d]pyrimidine (CASRN 3680-69-1), 5-bromo-1H-pyrrolo[2,3-b]pyridine (CASRN 183208-35-7), 5-chloro-1H-pyrrolo[2,3-b]pyridine (CASRN 866546-07-8), 5-bromo-1H-pyrrolo[3,2-b]pyridine (CASRN 1000341-51-4) and 2-chloro-5H-pyrrolo[3,2-d]pyrimidine (CASRN 1119280-66-8). Introduction of aminomethyl substitution (step 1) can be accomplished by palladium-catalyzed displacement of the halogen by cyanide (P. Anbarasan et al., "Recent developments and perspectives in palladium-catalyzed cyanation of aryl halides: synthesis of benzonitriles", *Chem. Soc. Rev.*, 2011 40:5049-5067, P. E. Maligres et al., "A highly catalytic robust palladium catalyzed cyanation of aryl bromides", *Tetrahedron Lett.* 1999 40:8193-8195). Reduction of the nitrile (step 2) can be carried out under routine conditions.

SCHEME C

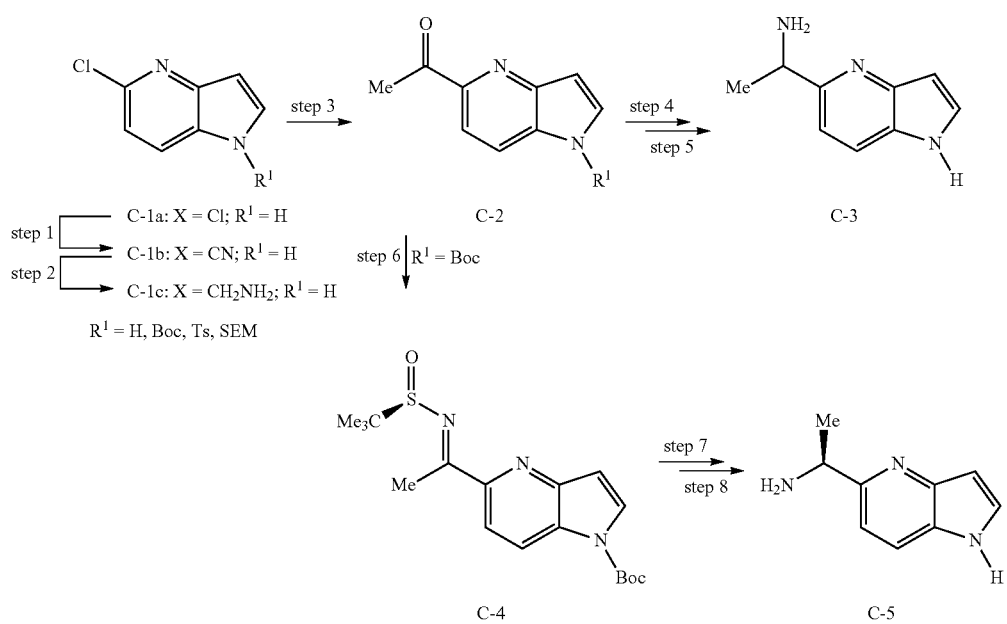

Alternatively, displacement of the halide with tributyl(1-ethoxyvinyl)stannane using a Stille coupling (step 3) affords the corresponding acyl derivative C-2. The Stille cross-coupling reaction is a palladium-catalyzed coupling of an aryl or vinyl stannanes with aryl or vinyl halides or -sulfonyloxy compoumds (J. K. Stille *Angew. Chem. Int. Ed.* 1986 25:508-524; A. F. Littke andd G. C. Fu *Angew. Chem. Int. Ed.* 1999, 38; 2411-2413). Commercially available Pd reagents including Pd(PPh$_3$)$_4$, Pd(OAc)$_2$ and Pd$_2$(dba)$_3$ can be used. Phosphine ligands are useful rate accelerants if they are not a component of the palladium catalyst. Relatively poorly electron-donating ligands tend to provide the greatest rate acceleration (V. Farina and B. Krishnan, *J. Am. Chem. Soc.* 1991 113:9585-9595). Additives including CuI have been incorporated to provide rate accelerations (V. Farina et al., *J. Org. Chem.* 1994 59:5905-5911). The reaction is typically run in aprotic solvents at elevated temperature.

Reductive amination (steps 4 & 5) of C-2 or Zn-catalyzed reduction of the corresponding oxime and subsequent optional deprotection if necessary affords the racemic amine C-3. Reductive amination is preferably carried out carried out by combining an amine and carbonyl compound in the presence of a complex metal hydride such as sodium borohydride, lithium borohydride, sodium cyanoborohydride, zinc borohydride, sodium triacetoxyborohydride or borane/pyridine conveniently at a pH of 1-7 or with hydrogen in the presence of a hydrogenation catalyst, e.g., in the presence of palladium on charcoal, at a hydrogen pressure of 1 to 5 bar, preferably at temperatures between 20° C. and the boiling temperature of the solvent used. Alternatively, chiral amine (C-5) can be produced (steps 6-8) addition of an aryl Grignard or aryllithium reagent to chiral N-tert-butylsulfinyl imines (C-4) followed by subsequent removal of the protecting groups. (D. A. Cogan et al., *Tetrahedron* 1999 55:8883-8904).

One skilled in the art will appreciate that at times it is expedient to mask the indole NH proton with a protecting group. Typical protecting groups which have been employed include the Boc group and related carbamates and toluenesulfonamides.

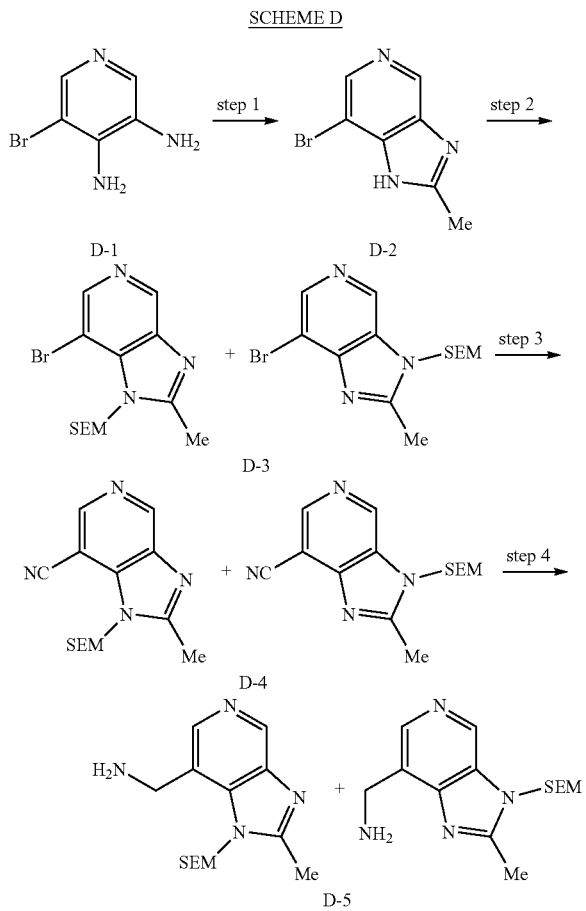

Aminomethyl benzimidazoles were prepared by cyclization of 5-bromo-3,4-diaminopyridine with triethyl orthoacetate to afford D-2. Amino protection was accomplished with 2-(trimethylsilyl)ethoxymethyl chloride which afforded an isomeric mixture SEM-protected amines which were subjected to palladium-catalyzed cyanation (step 3) and catalytic hydrogenation (step 4)

Biological Activity

Determination of the activity of PAK activity of a compound of formula I was accomplished using the PAK1 inhibition assay in Example 48. Efficacy of exemplary compounds in PAK1 assays are reported (Example 48). The range of PAK binding activities of Examples I-1 to I-36 was less than 1 nM (nanomolar) to about 10 μM (micromolar). A cell-based mechanistic assay (Example 49) was used to determine the effect of PAK inhibitors on down-stream signaling. Representative values for these assays can be found in TABLE 2 in example 48.

Dosage & Administration

The present invention provides pharmaceutical compositions or medicaments containing the compounds of the invention and at least one therapeutically inert carrier, diluent or excipient, as well as methods of using the compounds of the invention to prepare such compositions and medicaments. In one example, compounds of formula I with the desired degree of purity may be formulated by mixing with physiologically acceptable carriers, i.e., carriers that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on t the particular disorder being treated, the severity of the disorder, the particular patient being treated, the clinical condition of the individual patient, the cause of the disorder, the site of delivery of the agent, the method of administration, the scheduling of administration, and other factors known to medical practitioners The term "treating" or "treatment" of a disease state includes (1) inhibiting the disease state, i.e., arresting the development of the disease state or its clinical symptoms, or (2) relieving the disease state, i.e., causing temporary or permanent regression of the disease state or its clinical symptoms.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of formula I, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

A dose to treat human patients may range from about 0.1 mg to about 1000 mg of a compound of formula I. A typical dose may be about 1 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

For oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

In one embodiment, the pharmaceutical composition also includes at least one additional anti-proliferative agent.

An embodiment, therefore, includes a pharmaceutical composition comprising a compound of formula I, or a stereoisomer or pharmaceutically acceptable salt thereof. In a further embodiment includes a pharmaceutical composition comprising a compound of formula I, or a stereoisomer or pharmaceutically acceptable salt thereof, together with a pharmaceutically acceptable carrier or excipient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of formula I may be employed alone or in combination with other therapeutic agents for the treatment of a disease or disorder described herein, such as a hyperproliferative disorder (e.g., cancer). In certain embodiments, a compound of formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of formula I such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Suitable dosages for any of the above co-administered agents are those presently used and may be lowered due to the combined action (synergy) of the newly identified agent and other chemotherapeutic agents or treatments.

Combination therapies according to the present invention thus comprise the administration of at least one compound of formula I, or a stereoisomer, geometric isomer, tautomer, metabolite, or pharmaceutically acceptable salt and the use of at least one other cancer treatment method. The amounts of the compound(s) of formula I and the other pharmaceutically active chemotherapeutic agent(s) and the relative timings of administration will be selected in order to achieve the desired combined therapeutic effect.

Articles of Manufacture

In another embodiment of the invention, an article of manufacture, or "kit", containing materials useful for the treatment of the diseases and disorders described above is provided. In one embodiment, the kit comprises a container comprising a compound of formula I, or a stereoisomer, tautomer, or pharmaceutically acceptable salt thereof. The kit may further comprise a label or a package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula I or a formulation thereof which is effective for treating the condition and may have a sterile access port (for example, the container may be an intravenous solution bag or a vial having a stopper pierceable by a hypodermic injection needle). At least one active agent in the composition is a compound of formula I. Alternatively, or additionally, the article of manufacture may further comprise a second container comprising a pharmaceutically diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of formula I, such as tablets or capsules. Such a kit can include a number of unit dosages. An example of such a kit is a "blister pack". Blister packs are well known in the packaging industry and are widely used for packaging pharmaceutical unit dosage forms.

According to one embodiment, a kit may comprise (a) a first container with a compound of formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Referential Example 1

2-Chloro-N-(3-cyclopropyl-1H-pyrazol-5-yl)pyrimidin-4-amine (20)

A dried 5-L, three-necked round bottom flask fitted with an overhead stirrer and reflux condenser was charged with a solution of 2,4-dichloropyrimidine (250 g, 1.68 mol) in anhydrous DMSO (2300 mL). 3-Cyclopropyl-1H-pyrazol-5-amine (227.4 g, 1.85 mol) and DIPEA (438 mL, 2.52 mol) were added sequentially at RT. The resulting solution was stirred at 60° C. for 16 h, cooled to RT, and poured into ice water. The precipitated yellow solid was collected by vacuum filtration, washed with water, 1.5 N HCl (3×1 L), and finally with water (4×500 mL). The precipitate was dried by air suction overnight to give 320 g (81%) of 20 as yellow solid: $^1$H NMR (400 MHz, DMSO-d$^6$): δ 12.19 (s, 1H), 10.29 (s, 1H), 8.15 (s, 1H), 7.0 (br s, 1H), 6.0 (br s, 1H), 1.85-1.92 (m, 1H), 0.91-0.95 (m, 2H), 0.7 (m, 2H); MS (ESI+) m/z: 236 [M+1]$^+$.

Referential Example 2

2-Chloro-N-(5-cyclopropyl-1H-pyrazol-3-yl)-5-fluoropyrimidin-4-amine

2-Chloro-N-(5-cyclopropyl-1H-pyrazol-3-yl)-5-fluoropyrimidin-4-amine was prepared using a procedure analogous to the preparation of Referential Example 1, except 2,4-dichloro-5-fluoro-pyrimidine was used in place of 2,4-dichloropyrimidine: $^1$H NMR (400 MHz, DMSO-d$^6$, 125° C.): δ 12.28 (s, 1H), 10.38 (s, 1H), 8.24 (s, 1H), 6.27 (s, 1H), 1.94-1.89 (m, 1H), 0.95-0.93 (m, 2H), 0.71-0.69 (m, 2H); MS (ESI+) m/z: 254.1 [M+1]$^+$.

Referential Example 3

2-Chloro-N-(5-(3,3-difluorocyclobutyl)-1H-pyrazol-3-yl)pyrimidin-4-amine step 1: To a solution of 3-oxocyclobutanecarboxylic acid (20.0 g, 175.3 mmol) in DCM (500 mL) was added satd. aq. NaHCO$_3$ (293 mL), tetrabutyl ammonium bromide (75.3 g, 227.9 mmol) and 4-methoxybenzyl chloride (33.0 g, 210.4 mmol) and the mixture was stirred at RT overnight. After the reaction was completed, the mixture was diluted with water and extracted with DCM (2×250 mL). The organic layer was washed with water, dried (Na$_2$SO$_4$), filtered and concentrated in vacuo. The crude product was purified by SiO$_2$ chromatography eluting with petroleum ether/EtOAc (8:1) to afford 15.2 g (37%) of 4-methoxybenzyl 3-oxocyclobutanecarboxylate as an off-white solid.

step 2: To a solution of 4-methoxybenzyl 3-oxocyclobutanecarboxylate (15.2 g, 64.9 mmol) in DCM (300 mL) was added DAST (20.9 g, 130 mmol) and the mixture was stirred at RT overnight. After the reaction was complete, 5% aqueous NaHCO$_3$ was added, and the mixture was twice extracted with DCM (300 mL). The combined extracts were washed with water (200 mL), dried (Na$_2$SO$_4$), filtered and concentrated in vacuo. The crude product was purified by SiO$_2$ chromatography eluting with petroleum ether/EtOAc (10:1) to afford 14.0 g (84%) of 4-methoxybenzyl 3,3-difluorocyclobutanecarboxylate.

step 3: To a solution of NaH (2.85 g, 71.1 mmol) in dioxane (200 mL) was added MeCN (2.92 g, 71.1 mmol). The mixture was stirred for 20 min, then the solution of 4-methoxybenzyl 3,3-difluorocyclobutanecarboxylate (14.0 g, 54.7 mmol) in dioxane (100 mL) was added dropwise. After the mixture was heated at reflux for 4 h, the reaction mixture was poured into water (400 mL) then extracted with EtOAc (200 mL). The pH of the aqueous layer adjusted to 7 with 3N HCl and extracted with EtOAc. The organic layer was washed with brine (200 mL), dried (Na$_2$SO$_4$), filtered and concentrated to afford 13.5 g crude 3-(3,3-difluorocyclobutyl)-3-oxopropanenitrile which was used in the next step without purification.

step 4: To a solution of 3-(3,3-difluorocyclobutyl)-3-oxopropanenitrile (12.5 g, 78.6 mmol) in EtOH (250 mL) was added hydrazine hydrate (5.9 g, 117.9 mmol) and the resulting mixture was stirred at 75° C. overnight. After concentrating the reaction mixture in vacuo, the residue was redissolved in EtOAc (500 mL) and washed with satd. aq. NaHCO$_3$. The aqueous layer was extracted with EtOAc and the combined extracts washed with brine (100 mL), dried (Na$_2$SO$_4$), filtered and concentrated in vacuo. The crude product was purified by SiO$_2$ chromatography eluting with DCM/MeOH (10:1) to afford 3.46 g (39%) of 5-(3,3-difluoro-cyclobutyl)-1H-pyrazol-3-ylamine as a light yellow solid: $^1$H NMR (400 MHz, DMSO-d$_o$): δ 11.20 (br s, 1H), 5.23 (s, 1H), 4.65 (br s, 2H), 3.16-3.13 (m, 1H), 2.88-2.84 (m, 2H), 2.64-2.57 (m, 2H); MS (ESI+) m/z: 174 [M+1]$^+$.

step 5: 2-Chloro-N-(5-(3,3-difluorocyclobutyl)-1H-pyrazol-3-yl)pyrimidin-4-amine was prepared using procedure analogous to the preparation of Referential Example 1, except 5-(3,3-difluorocyclobutyl)-1H-pyrazol-3-amine was used in place of 3-cyclopropyl-1H-pyrazol-5-amine: $^1$H NMR (400 MHz, DMSO-d$^6$) δ 12.43 (s, 1H), 10.40 (s, 1H), 8.19 (s, 1H), 7.20 (br s, 1H), 6.20 (br s, 1H), 3.43-3.35 (m, 1H), 3.20-2.85 (m, 2H), 2.75-2.72 (m, 2H); MS (ESI+) m/z: 286 [M+1]$^+$.

Referential Examples 4 and 5

2-chloro-N-(5-((1R,2R)-2-fluorocyclopropyl)-1H-pyrazol-3-yl)pyrimidin-4-amine (22) and 2-chloro-N-(5-((1S,2S)-2-fluorocyclopropyl)-1H-pyrazol-3-yl)pyrimidin-4-amine (24)

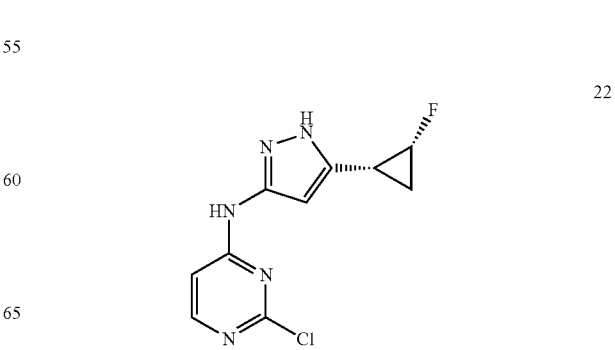

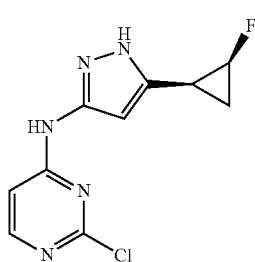

24 step 1: To a solution of MeCN (7.28 mL, 139 mmol) in anhydrous THF (130 mL) at −78° C. under N₂ was added n-butyllithium (2.4 mol/L) in hexanes (58 mL, 139 mmol) dropwise. The mixture was stirred at −78° C. for 30 min then cis-ethyl-2-fluorocyclo-propanecarboxylate (1.5 g; 87.0 mmol) was added dropwise with stirring while maintaining the temperature at −78° C. The resulting solution was stirred at 25° C. for 2 h, quenched by the addition of 50% satd. aq. NH₄Cl solution and extracted with EtOAc (3×50 mL). The combined organic layers were dried (Na₂SO₄), filtered and concentrated under vacuum to afford 7.7 g of crude cis-3-(2-fluorocyclopropyl)-3-oxopropanenitrile as a red oil. Crude cis-3-(2-fluoro-cyclopropyl)-3-oxopropanenitrile was dissolved in EtOH (130 mL) and hydrazine (8.45 mL, 261 mmol) was added. The reaction mixture was heated at reflux for 16 h then concentrated in vacuo. The resultant orange solid was triturated with DCM (ca. 50 mL). The precipitate was filtered, rinsed with DCM, and dried in vacuo to obtain 7.48 g (60.9%) of cis-5-(2-fluorocyclopropyl)-1H-pyrazol-3-amine as a tan solid. ¹H NMR (400 MHz, DMSO-d⁶) δ 11.18 (br s, 1H), 5.16 (s, 1H), 4.81 (ddd, J=66.3, 9.5, 5.2 Hz, 1H), 4.46 (br s, 2H), 1.99-1.81 (m, 1H), 1.23-1.02 (m, 2H).

step 2: Racemic cis-2-chloro-N-[5-(2-fluorocyclopropyl)-1H-pyrazol-3-yl]pyrimidin-4-amine was prepared using procedure analogous to the preparation of referential example 1, except cis-5-(2-fluorocyclo-propyl)-1H-pyrazol-3-amine was used in place of 3-cyclopropyl-1H-pyrazol-5-amine and the crude product was resolved by chiral SFC chromatography to obtain the following:

Peak 1: 2-chloro-N-(5-((1R,2R)-2-fluorocyclopropyl)-1H-pyrazol-3-yl)pyrimidin-4-amine (1.31 g, 33.4%); MS (ESI+) m/z: 254 [M+1]⁺.

Peak 2: 2-chloro-N-(5-((1S,2S)-2-fluorocyclopropyl)-1H-pyrazol-3-yl)pyrimidin-4-amine (1.43 g, 36.5%); MS (ESI+) m/z: 254 [M+1]⁺.

The absolute stereochemistry was determined by single crystal x-ray diffraction.

Referential Examples 6 and 7

2-chloro-N-(5-((1R,2S)-2-fluorocyclopropyl)-1H-pyrazol-3-yl)pyrimidin-4-amine (26) and 2-chloro-N-(5-((1S,2R)-2-fluorocyclopropyl)-1H-pyrazol-3-yl)pyrimidin-4-amine (28)

26

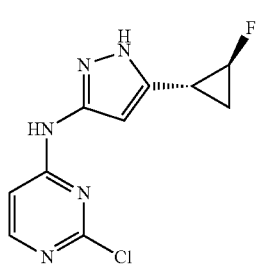

28

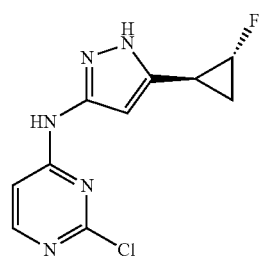

Racemic trans-2-chloro-N-[5-(2-fluorocyclopropyl)-1H-pyrazol-3-yl]pyrimidin-4-amine was prepared using procedure analogous to Referential Example 4, except trans-ethyl-2-fluorocyclo-propanecarboxylate was used in place of cis-ethyl-2-fluoro-cyclopropanecarboxylate. Chiral SFC resolution afforded the following:

Peak 1: 2-chloro-N-(5-((1R,2S)-2-fluorocyclopropyl)-1H-pyrazol-3-yl)pyrimidin-4-amine; MS (ESI+) m/z: 254 [M+1]⁺.

Peak 2: 2-chloro-N-(5-((1S,2R)-2-fluorocyclopropyl)-1H-pyrazol-3-yl)pyrimidin-4-amine; MS (ESI+) m/z: 254 [M+1]⁺.

The absolute stereochemistry was determined by single crystal x-ray diffraction.

Referential Example 8

(1H-pyrrolo[2,3-c]pyridin-4-yl)methanamine

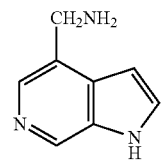

step 1: A mixture of 4-bromo-1H-pyrrolo[2,3-c]pyridine (320 mg, 1.62 mmol), Pd(dppf)Cl₂ (131 mg, 0.179 mmol), zinc cyanide (190 mg, 1.62 mmol), and zinc powder (21 mg, 0.324 mmol) in DMF (20 mL) was stirred at 120° C. for 2 h. The reaction mixtue was cooled to RT and H₂O (100 mL) was added. The reaction mixture extracted with EtOAc (3×50 mL). The organic layers were concentrated tinder reduced pressure and the crude residue was purified by SiO₂ chromatography eluting with petroleum ether/EtOAc (1:1) to afford 232 mg (99.8%) of 1H-pyrrolo[2,3-c]pyridine-4-carbonitrile as yellow solid: MS (ESI) m/z: 144.2 [M+1]⁺.

step 2: A mixture of 1H-pyrrolo[2,3-c]pyridine-4-carbonitrile (232 mg, 1.62 mmol) and Raney Ni (200 mg) in a solution of ammonia/MeOH (7N, 40 mL) was stirred at RT for 4 h. The reaction mixture was filtered and the wet cake was washed with MeOH (3×10 mL). The filtrate was concentrated under reduced pressure to afford 236 mg (99.0%) of (1H-pyrrolo[2,3-c]pyridin-4-yl)methanamine as yellow solid: MS (ESI) m/z: 148.3 [M+1]⁺.

Referential Example 9

(1H-pyrrolo[2,3-b]pyridin-4-yl)methanamine

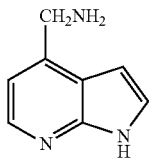

Following the procedure as described in step 2 of Referential Example 8, (1H-pyrrolo[2,3-b]-pyridin-4-yl)methanamine was prepared using 1H-pyrrolo[2,3-b]pyridine-4-carbonitrile in place of 1H-pyrrolo[2,3-c]pyridine-4-carbonitrile as starting material: MS (ESI) m/z: 148.1 [M+1]$^+$.

Referential Example 10

1H-Pyrrolo[3,2-c]pyridin-4-yl)methanamine

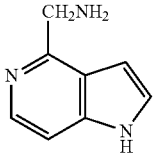

step 1: A mixture of 4-chloro-1H-pyrrolo[3,2-c]pyridine (500 mg, 3.28 mmol), zinc cyanide (422 mg, 3.61 mmol), Pd$_2$(dba)$_3$ (600 mg, 0.656 mmol), dppf (729 mg, 1.312 mmol), and Zn powder (21 mg, 0.328 mmol) in NMP (30 mL) under nitrogen was stirred at 120° C. for 18 h. The reaction mixture was cooled, poured into water (150 mL), extracted with DCM (3×50 mL), dried (MgSO$_4$), filtered and concentrated under reduced pressure. The crude residue was purified by SiO$_2$ chromatography eluting with petroleum ether:EtOAc (1:1) as eluting solvents to afford 1H-pyrrolo[3,2-c]pyridine-4-carbonitrile as a white solid (150 mg, 32%). MS (ESI) m/z: 144.3 [M+1]$^+$.

step 2: Following the procedure as described in step 2 of Referential Example 8, (1H-pyrrolo[3,2-c]pyridin-4-yl)methanamine was prepared using 1H-pyrrolo[3,2-c]pyridine-4-carbonitrile in place of 1H-pyrrolo[2,3-c]pyridine-4-carbonitrile as starting material; MS (ESI) m/z: 148.2 [M+1]$^+$.

Referential Example 11

(±)-1-(1-tosyl-1H-pyrrolo[3,2-c]pyridin-4-yl)ethanamine

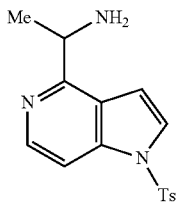

step 1: A mixture of 4-chloro-1H-pyrrolo[3,2-c]pyridine (1.0 g, 6.58 mmol), Pd(PPh$_3$)$_4$ (763 mg, 0.66 mmol), and tributyl(1-ethoxyvinyl)stannane (2.61 g, 7.23 mmol) in NMP (20 mL) was stirred under N$_2$ at 140° C. for 18 h. The reaction mixture was poured into aqueous HCl solution (2 N, 150 mL), stirred at RT for 2 h, and washed with DCM (50 mL×3). The aqueous layer was adjusted to pH 8 with NaHCO$_3$ (solid), extracted with EtOAc (50 mL×3), and concentrated under reduced pressure to afford 680 mg (64.6%) of 1-(1H-pyrrolo[3,2-c]pyridin-4-yl)ethanone as yellow solid: MS (ESI) nilz: 161.1 [M+1]$^+$.

step 2: To a mixture of 1-(1H-pyrrolo[3,2-c]pyridin-4-yl)ethanone (680 mg, 4.25 mmol) in anhydrous THF (40 mL) at 0° C. was added NaH (60% in mineral oil, 204 mg, 5.1 mmol). After the mixture was stirred at 0° C. for 30 min, 4-methylbenzene-1-sulfonyl chloride (850 mg, 4.46 mmol) was added. The reaction mixture was stirred at 0° C. for 1 h. The reaction mixture was poured into water (150 mL), extracted with EtOAc (3×50 mL) and concentrated under reduced pressure to afford 1.32 g (98.9%) of 1-(1-tosyl-1H-pyrrolo[3,2-c]pyridin-4-yl)ethanone as yellow solid: MS (ESI) m/z: 315.2 [M+1]$^+$.

step 3: To a mixture of 1-(1-tosyl-1H-pyrrolo[3,2-c]pyridin-4-yl)ethanone (1.32 g, 4.2 mmol) in MeOH (50 mL) at RT was added hydroxylamine hydrochloride (877 mg, 12.61 mmol) followed by NaOAc (3.45 g, 42.0 mmol). The reaction mixture was stirred at 80° C. for 1 h then concentrated tinder reduced pressure. Water (100 mL) was added to the reaction mixture, and the mixture extracted with EtOAc (50 mL×3). The combined organic layers were concentrated under reduced pressure to afford 1.35 g (97.6%) of 1-(1-tosyl-1H-pyrrolo[3,2-c]pyridin-4-yl)ethanone oxime as yellow solid: MS (ESI) m/z: 320.1 [M+1]$^+$.

step 4: A mixture of 1-(1-tosyl-1H-pyrrolo[3,2-c]pyridin-4-yl)ethanone oxime (1.29 g, 3.92 mmol), zinc (2.55 g, 39.2 mmol), and NH$_4$Cl (2.10 mg, 39.2 mmol) in MeOH (5 mL) and HOAc (3 mL) was stirred at 80° C. for 4 h. The mixture was cooled to RT and the solid filtered. The filtrate was concentrated under reduced pressure. To the residue was added ammonia solution (50 mL) and the reaction mixture was extracted with DCM (3×50 mL). The combined organic extracts were concentrated under reduced pressure. The crude product was purified by SiO$_2$ chromatography eluting with DCM/MeOH/TEA (15:1:0.2) to afford 1.08 g (87.4%) (±)-1-(1-tosyl-1H-pyrrolo[3,2-c]pyridin-4-yl)ethanamine as a yellow solid: MS (ESI) m/z: 316.2 [M+1]$^+$.

Referential Example 12

(1-tosyl-1H-pyrrolo[2,3-b]pyridin-5-yl)methanamine

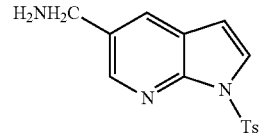

step 1: To a solution of 5-bromo-1H-pyrrolo[2,3-b]pyridine (2.0 g, 10 mmol) in anhydrous THF (50 mL) at −70° C. under nitrogen was added n-butyl lithium (2.5 M in hexane, 50 mmol) and the reaction mixture was stirred for 1 h at −70° C. The resulting orange gel was quenched with methyl formate (10 mL) and the reaction mixture was slowly warmed to RT. The mixture was poured into water (20 mL) and extracted with EtOAc (2×250 mL). The organic layers were combined, dried (Na$_2$SO$_4$), filtered, and concentrated to afford 500 mg, (33%) of 1H-pyrrolo[2,3-b]pyridine-5-carbaldehyde as yellow solid. MS (ESI) m/z: 147.2 [M+1]+.

step 2: To a solution of 1H-pyrrolo[2,3-b]pyridine-5-carbaldehyde (500 mg, 3.42 mmol) in THF (50 mL) at 0° C. was added NaH (205 mg, 60% in oil, 5.13 mmol) with vigorous stirring. After 30 min, TsCl (845 mg, 4.45 mmol) was added. The reaction mixture was stirred at RT for 18 h, and then the solvent was removed in vacuo. The residue was partitioned between DCM (300 mL) and water (100 mL). The organic layer was separated, dried ($MgSO_4$), filtered, and concentrated to afford 580 mg (56%) of 1-tosyl-1H-pyrrolo[2,3-b]pyridine-5-carbaldehyde as yellow solid. MS (ESI) m/z: 301.2 [M+1]+.

step 3: To a solution of 1-tosyl-1H-pyrrolo[2,3-b]pyridine-5-carbaldehyde (0.58 g, 1.93 mmol) in EtOH (5 mL) was added hydroxylamine hydrochloride (0.7 g, 9.6 mmol) and pyridine (0.5 mL). The reaction mixture was heated at 70° C. for 18 h and then the solvent was removed under reduced pressure to afford 0.6 g (98%) of 1-tosyl-1H-pyrrolo[2,3-b]pyridine-5-carbaldehyde oxime as white solid which was used in the next step without further purification. MS (ESI) m/z: 316.2 [M+1]+.

step 4: To a solution of 1-tosyl-1H-pyrrolo[2,3-b]pyridine-5-carbaldehyde oxime (600 mg, 1.9 mmol) in MeOH (10 mL) was added zinc powder (600 mg, 9.5 mmol) and ammonium chloride (1.0 g, 19 mmol). The suspension was refluxed for 18 h and then the solid was filtered. The filtrate was diluted with DCM (200 mL) and water (50 mL). The organic layer was separated, dried ($MgSO_4$), filtered, and concentrated to afford 503 mg (98%) of (1-tosyl-1H-pyrrolo[2,3-b]pyridin-5-yl)methanamine as yellow solid which was used in the next step without further purification; MS (ESI) m/z: 302.1 [M+1]

Referential Example 13

1-(1H-pyrrolo[3,2-b]pyridin-5-yl)ethanamine

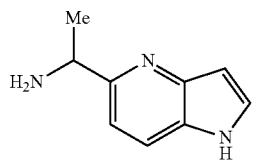 [SMILES: CC(N)c1ccc2[nH]ccc2n1]

step 1: To a stirred solution of 5-chloro-1H-pyrrolo[3,2-b]pyridine (3.0 g, 19.66 mmol) and DMAP (243 mg, 1.97 mmol) in anhydrous MeCN (50 mL) at 0° C. was added di-tert-butyl dicarbonate (5.15 g, 23.59 mmol), and the reaction mixture was stirred at RT under $N_2$ for 18 h. The solvent was removed under reduced pressure, and the crude residue was diluted with EtOAc. The EtOAc layer was washed with water and brine, dried ($Na_2SO_4$), filtered, and concentrated in vacuo. The crude product was purified by $SiO_2$ chromatography eluting with EtOAc/heptane to give 4.94 g (99.4%) of tert-butyl 5-chloro-1H-pyrrolo[3,2-b]pyridine-1-carboxylate as a white solid. $^1$H NMR (400 MHz, DMSO-$d_6$) δ 8.34 (d, J=8.7 Hz, 1H), 8.06 (d, J=3.8 Hz, 1H), 7.41 (d, J=8.7 Hz, 1H), 6.82 (d, J=3.8 Hz, 1H), 1.64 (s, 9H); MS (ESI) m/z: 253 [M+1]+.

step 2: A high-pressure tube was charged with tributyl(1-ethoxyvinyl)stannane (7.75 g, 21.45 mmol) and tert-butyl 5-chloropyrrolo[3,2-b]pyridine-1-carboxylate (4.17 g, 16.50 mmol) in degassed DMF (64.0 mL) and $Pd(PPh_3)_4$ (1.9 g, 1.65 mmol) was added in one batch. The tube was closely tightly and the reaction mixture was stirred at 100° C. under $N_2$ for 2 d. The reaction mixture was cooled, diluted with EtOAc (350 mL), and filtered through a pad of Celite® to remove solid Pd. The filtrate was washed with water and brine, dried ($Na_2SO_4$), filtered, and concentrated in vacuo. The crude product was dissolved in anhydrous THF (80.2 mL), and 2N HCl (41 mL) was added. The reaction mixture was stirred at RT under $N_2$ for 16 h, poured into 10% aq. NaOH solution (100 mL) and then extracted with EtOAc (3×150 mL). The combined organic phases were washed with water and brine, dried ($Na_2SO_4$), filtered, and concentrated under reduced pressure. The crude product was purified by $SiO_2$ chromatography eluting with EtOAc/heptane to afford 1.69 g (64.1%) of 1-(1H-pyrrolo[3,2-b]-pyridin-5-yl)ethanone as a white solid. $^1$H NMR (400 MHz, $CDCl_3$) δ 8.49 (s, 1H), 7.99 (d, J=8.5 Hz, 1H), 7.74 (d, J=8.5 Hz, 1H), 7.54 (t, J=3.0 Hz, 1H), 6.86 (s, 1H), 2.80 (s, 3H); MS (ESI) m/z: 161.3 [M+1]+.

step 3: To 1-(1H-pyrrolo[3,2-b]pyridin-5-yl)ethanone (2.32 g, 14.48 mmol) and DMAP (178.7 mg, 1.448 mmol) in anhydrous MeCN (98.4 mL) at 0° C. was added di-tert-butyl dicarbonate (3.79 g, 17.38 mmol), and the reaction mixture was stirred at RT under $N_2$ for 18 h. The solvent was removed in vacuo and the crude residue was diluted with EtOAc. The EtOAc layer was washed with water and brine, dried ($Na_2SO_4$), filtered and concentrated invacuo. Trituration with DCM (10 mL) gave 3.30 g (87.5%) of tert-butyl 5-acetyl-1H-pyrrolo-[3,2-b]pyridine-1-carboxylate a white solid; $^1$H NMR (400 MHz, $CDCl_3$) δ 8.45 (d, J=8.5 Hz, 1H), 8.07 (d, J=8.6 Hz, 1H), 7.92 (d, J=3.8 Hz, 1H), 6.87 (d, J=3.9 Hz, 1H), 2.80 (s, 3H), 1.69 (s, 9H); MS (ESI) m/z: 261.4 [M+1]+.

step 4: Following the procedure as described in step 3 or Referential Example 12, tert-butyl 5-(1-(hydroxyimino)ethyl)-1H-pyrrolo[3,2-b]pyridine-1-carboxylate was prepared using tert-butyl 5-acetyl-1H-pyrrolo-[3,2-b]pyridine-1-carboxylate in place of 1-tosyl-1H-pyrrolo[2,3-b]pyridine-5-carbaldehyde as the starting material: $^1$H NMR (400 MHz, DMSO-$d^6$) δ 11.39 (s, 1H), 8.30 (d, J=8.8 Hz, 1H), 7.97 (d, J=3.8 Hz, 1H), 7.88 (d, J=8.8 Hz, 1H), 6.87 (d, J=3.8 Hz, 1H), 2.27 (s, 3H), 1.64 (s, 9H); MS (ESI) m/z: 276.2 [M+1]+.

step 5: Following the procedure as described for step 4 of Referential Example 12, 1-(1H-pyrrolo[3,2-b]pyridin-5-yl)ethanamine was prepared using tert-butyl 5-(1-(hydroxylimino)ethyl)-1H-pyrrolo[3,2-b]pyridine-1-carboxylate in place of 1-tosyl-1H-pyrrolo[2,3-b]pyridine-5-carbaldehyde oxime as the starting material: $^1$H NMR (400 MHz, $CDCl_3$) δ 9.29 (s, 1H), 7.61 (d, J=8.4 Hz, 1H), 7.42 (d, J=3.0 Hz, 1H), 7.12 (d, J=8.4 Hz, 1H), 6.70 (d, J=2.8 Hz, 1H), 4.30 (q, J=6.7 Hz, 1H), 2.00 (s, 2H), 1.50 (d, J=6.7 Hz, 3H); MS (ESI) m/z: 161.9

Referential Example 14

(S)-1-(1H-pyrrolo[3,2-b]pyridin-5-yl)ethanamine hydrochloride

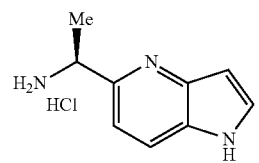 [SMILES: C[C@H](N)c1ccc2[nH]ccc2n1 ; Cl]

step 1: To a solution of tert-butyl 5-acetylpyrrolo[3,2-b]pyridine-1-carboxylate (2.0 g, 7.68 mmol) and (R)-2-methylpropane-2-sulfinamide (1.04 g, 8.45 mmol) dissolved in anhydrous THF (50 mL) was added titanium (IV) ethoxide (3.2 mL, 15.37 mmol) at RT under a $N_2$ atmosphere. The reaction mixture was stirred at 75° C. under $N_2$ for 16 h. The solvent was removed in vacuo and the crude residue was diluted with EtOAc (ca. 100 mL). The reaction mixture was vigorously stirred while a saturated solution of brine (~20 mL) was added slowly. The reaction mixture was stirred for 15 min and filtered through a pad of Celite®. The organic layer from the filtrate was washed with water and brine, dried ($Na_2SO_4$), filtered, and concentrated in vacuo. The crude product was purified by $SiO_2$ chromatography eluting with EtOAc/heptane to afford 1.50 g (53.7%) of (R)-tert-butyl 5-(1-(tert-butylsulfinylimino)-ethyl)-1H-pyrrolo[3,2-b]pyridine-1-carboxylate as yellow solid: $^1H$ NMR (400 MHz, $CDCl_3$) δ 8.38 (d, J=8.6 Hz, 1H), 8.16 (d, J=8.8 Hz, 1H), 7.88 (d, J=3.8 Hz, 1H), 6.83 (d, J=3.8 Hz, 1H), 2.94 (s, 3H), 1.69 (s, 9H), 1.35 (s, 9H); MS (ESI) m/z: 364.3 $[M+1]^+$.

step 2: To a solution of (R)-tert-butyl 5-(1-(tert-butylsulfinylimino)ethyl)-1H-pyrrolo[3,2-b]-pyridine-1-carboxylate (1.18 g, 3.25 mmol) in anhydrous THF (21.1 mL) at 0° C. was added dropwise L-selectride (1.0 mol/L) in THF (4.9 mL). The resultant orange reaction mixture was warmed to RT and stirred under $N_2$ for 3 h. The solvent was removed in vacuo, and the crude product was purified by $SiO_2$ chromatography eluting with MeOH/EtOAc+1% TEA to afford 700 mg (81.3%) of (R)—N—((S)-1-(1H-pyrrolo[3,2-b]-pyridin-5-yl)ethyl)-2-methylpropane-2-sulfinamide as a foam (95% ee). The enantiomers were separated via chiral SFC chromatography to give 597.0 mg (100% ee) of (R)—N—((S)-1-(1H-pyrrolo[3,2-b]-pyridin-5-yl)ethyl)-2-methylpropane-2-sulfinamide: $^1H$ NMR (400 MHz, MeOD) δ 7.79 (d, J=8.5 Hz, 1H), 7.55 (d, J=3.3 Hz, 1H), 7.24 (d, J=8.4 Hz, 1H), 6.58 (d, J=3.1 Hz, 1H), 4.73-4.66 (m, 1H), 1.63 (d, J=6.9 Hz, 3H), 1.19 (s, 9H); MS (ESI) m/z: 266.3 $[M+1]^+$.

step 3: To a solution of (R)—N—((S)-1-(1H-pyrrolo[3,2-b]pyridin-5-yl)ethyl)-2-methylpropane-2-sulfinamide (597.0 mg, 2.25 mmol) in anhydrous MeOH (9 mL) was added HCl (4.0 mol/L) in dioxane (11 mL). The reaction mixture was stirred at 40° C. under $N_2$ for 7 h. Volatile solvent was removed under reduced pressure. The crude product was triturated with MeOH/ether until solid is seen. The light yellow solid was filtered and dried under high vacuum to afford 524.0 mg (99.5%) of the desired product as HCl salt: $^1H$ NMR (400 MHz, DMSO-$d^6$) δ 12.57 (s, 1H), 9.00 (s, 3H), 8.42 (d, J=6.8 Hz, 1H), 8.10 (s, 1H), 7.74 (d, J=7.4 Hz, 1H), 6.79 (s, 1H), 4.88 (s, 1H), 1.67 (d, J=6.8 Hz, 3H); MS (ESI) m/z: 162.1 $[M+1]^+$.

Referential Example 15

N-methyl-1-(1H-pyrrolo[3,2-b]pyridin-5-yl)ethanamine

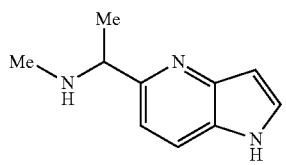 [SMILES: CNC(C)c1ccc2[nH]ccc2n1]

A microwave vial was charged with 1-(1H-pyrrolo[3,2-b]pyridin-5-yl)ethanone (1.50 g, 9.36 mmol), methanamine hydrochloride (8.85 g, 131.1 mol), $NaBH_3CN$ (765.0 mg, 12.18 mmol), and anhydrous EtOH (31 mL) and stirred while irradiated in a microwave (300 Watts) at 130° C. for 2 min. The resulting solid was filtered and rinsed well with EtOH. The filtrate was concentrated in vacuo. The crude product was redissolved in EtOAc and twice washed with 10% aq. NaOH, water and brine. The organic phase was dried ($Na_2SO_4$), filtered, and concentrated in vacuo. The crude product was triturated with DCM, and the insoluble solid was filtered through a pad of Celite®. The filtrate was concentrated in vacuo and dried under high vacuum to afford N-methyl-1-(1H-pyrrolo[3,2-b]pyridin-5-yl)ethanamine as a solid: $^1H$ NMR (400 MHz, $CDCl_3$) δ 8.87 (s, 1H), 7.66 (d, J=8.4 Hz, 1H), 7.45 (d, J=3.3 Hz, 1H), 7.14 (d, J=8.4 Hz, 1H), 6.72 (d, J=3.3 Hz, 1H), 3.95 (q, J=6.7 Hz, 1H), 2.37 (s, 3H), 1.47 (d, J=6.7 Hz, 3H).

Referential Example 16

N-methyl-1-(1H-pyrrolo[3,2-b]pyridin-5-yl)methanamine hydrochloride

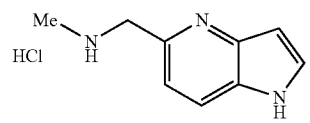

step 1: To a stirred mixture of 1H-pyrrolo[3,2-b]pyridin-5-yl-methanamine hydrochloride (1.0 g, 5.44 mmol), DIPEA (1.05 mL, 5.99 mmol), and DMAP (67.2 mg, 0.54 mmol) in anhydrous MeCN (28 mL) at 0° C. was added di-tert-butyl dicarbonate (2.97 g, 13.6 mmol) and the reaction mixture was stirred at RT under $N_2$ for 18 h. The solvent was removed in vacuo. The crude product was diluted with EtOAc and washed with water and brine, dried ($Na_2SO_4$), filtered, and concentrated in vacuo. The crude material was purified by $SiO_2$ chromatography eluting with a mixture of EtOAc containing 1% TEA and heptane to afford 1.50 g (79.3%) of tert-butyl 5-((tert-butoxycarbonylamino)methyl)-1H-pyrrolo[3,2-b]pyridine-1-carboxylate as a foam: $^1H$ NMR (400 MHz, $CDCl_3$) δ 8.32 (d, J=8.1 Hz, 1H), 7.82 (d, J=3.6 Hz, 1H), 7.22 (d, J=8.5 Hz, 1H), 6.73 (d, J=3.8 Hz, 1H), 5.56 (br s, 1H), 4.53 (d, J=5.1 Hz, 2H), 1.68 (s, 9H), 1.46 (s, 9H); MS (ESI) m/z: 348.3 $[M+1]^+$.

step 2: To a stirred solution of tert-butyl 5-[(tert-butoxycarbonylamino)methyl]-pyrrolo-[3,2-b]pyridine-1-carboxylate (360.0 mg, 1.036 mmol) and iodomethane (0.065 mL, 1.036 mmol) in anhydrous THF (6.3 mL) cooled to −40° C. was added dropwise lithium bis(trimethylsilyl)amide in THF (1.24 mL, 1.24 mmol, 1M). The reaction mixture was warmed to 0° C. and stirred at 0° C. for 1 h. The reaction was quenched with water and then diluted with EtOAc. The organic layer was washed with water and brine, dried ($Na_2SO_4$), filtered, and concentrated in vacuo. The crude material was purified by $SiO_2$ chromatography eluting with a mixture of EtOAc containing 1% TEA and heptane to afford 130.0 mg (37.3%) of tert-butyl 5-((tert-butoxycarbonyl(methyl)amino)methyl)-1H-pyrrolo[3,2-b]pyridine-1-carboxylate as a foam: $^1H$ NMR (400 MHz, $CDCl_3$) δ 8.33 (d, J=7.6 Hz, 1H), 7.82 (d, J=3.5 Hz, 1H), 7.27-7.10 (m, 1H), 6.73 (d, J=3.7 Hz, 1H), 4.64 (s, 2H), 3.02-2.82 (m, 3H), 1.68 (s, 9H), 1.56-1.41 (m, 9H); MS (ESI) m/z: 362.3 $[M+1]^+$ step 3: To a stirred solution of tert-butyl 5-((tert-butoxy-carbonyl(methyl)amino)-methyl)-1H-pyrrolo[3,2-b]pyridine-1-carboxylate (140.0 mg, 0.387 mmol) in MeOH (2 mL) and DCM (2 mL) was added HCl in dioxane (2.3 mL, 9.05 mmol, 4M) and the reaction mixture was stirred at 50° C. under N$_2$ for 7 h. The solvent was removed in vacuo and the crude product was pumped dry on high-vacuum line to afford 87.1 mg (96.1%) of the desired product as HCl salt: $^1$H NMR (400 MHz, DMSO-d$^6$) δ 12.51 (br s, 1H), 9.74 (br s, 2H), 8.38 (d, J=7.9 Hz, 1H), 8.10 (s, 1H), 7.68 (d, J=8.0 Hz, 1H), 6.78 (s, 1H), 4.52 (s, 2H), 2.63 (s, 3H); MS (ESI) m/z: 162.3 [M+1]$^+$.

Referential Example 17 tert-butyl 5-acetyl-1H-pyrrolo[2,3-c]pyridine-1-carboxylate

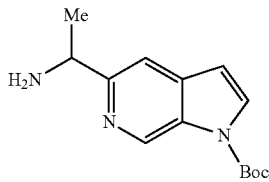

step 1: Following the procedure as described for step 1 of referential example 13, tert-butyl 5-bromo-1H-pyrrolo[2,3-c]pyridine-1-carboxylate was prepared using 5-bromo-1H-pyrrolo-[2,3-c]pyridine in place of 5-chloro-1H-pyrrolo[3,2-b]pyridine as the starting material: MS (ESI) m/z: 297.2 [M+1]$^+$.

step 2: Following the procedure as described for step 2 of referential example 13, 1-(1H-pyrrolo[2,3-c]pyridin-5-yl)ethanone was prepared using tert-butyl 5-bromo-1H-pyrrolo-[2,3-c]pyridine-1-carboxylate in place of tert-butyl 5-chloro-pyrrolo[3,2-b]pyridine-1-carboxylate as the starting material. MS (ESI) m/z: 161.2 [M+1]$^+$.

step 3: Following the procedure as described in step 3 of referential Example 13, tert-butyl 5-acetyl-1H-pyrrolo[2,3-c]pyridine-1-carboxylate was prepared using 1-(1H-pyrrolo[2,3-c]-pyridin-5-yl)ethanone in place of 1-(1H-pyrrolo[3,2-b]pyridin-5-yl)ethanone as the starting material: MS (ESI) m/z: 261.2 [M+1]$^+$.

step 4: A sealed-cap vial was charged with tert-butyl 5-acetyl-1H-pyrrolo[2,3-c]pyridine-1-carboxylate (225 mg, 0.86 mmol), NH$_4$OAc ammonium acetate (666 mg, 8.6 mmol), NaBH$_3$CN (71 mg, 1.1 mmol) and MeOH (7 mL). The reaction was stirred at RT for 24 h, after which additional NH$_4$OAc (333 mg, 4.3 mmol) and NaBH$_3$CN (27 mg, 0.43 mmol) were added. The reaction mixture was stirred for another 24 h then concentrated in vacuo. The residue was partitioned between 2N NaOH and EtOAc. The aqueous layer was thrice extracted with EtOAc. The organic extracts were combined and dried (Na$_2$SO$_4$), filtered and concentrated in vacuo. The crude residue was purified by SiO$_2$ chromatography eluting with a mixture of EtOAc containing 1% TEA and MeOH to afford 95 mg (42%) of tert-butyl 5-(1-aminoethyl)-1H-pyrrolo[2,3-c]pyridine-1-carboxylate: MS (ESI) m/z: 262.2 [M+1]$^+$.

Referential Example 18

(S)-1-(3-chloro-1H-pyrrolo[3,2-b]pyridin-5-yl)ethanamine

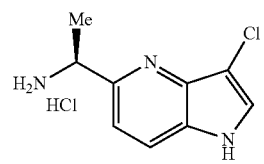 [SMILES: C[C@H](N)c1ccc2[nH]cc(Cl)c2n1 ; Cl]

step 1: To a solution 1-(1H-pyrrolo[3,2-b]pyridin-5-yl)ethanone (517.0 mg, 3.23 mmol) in anhydrous DMF (5.0 mL) at 0° C. was added a solution of NCS (462.0 mg, 3.39 mmol) dissolved in anhydrous DMF (10 mL). The reaction mixture was stirred at 0° C. for 1 h and then at RT for 18 h. The reaction mixture was diluted with EtOAc, and the organic layer was washed with sat'd. aq. NaHCO$_3$ solution, water and brine, dried (Na$_2$SO$_4$), filtered and concentrated in vacuo. The crude residue was purified by SiO$_2$ chromatography eluting with EtOAc/heptane. Recovered product was crystallized from DCM to afford 600 mg (95.5%) of 1-(3-chloro-1H-pyrrolo[3,2-b]pyridin-5-yl)ethanone as a white solid: $^1$H NMR (400 MHz, DMSO-d$^6$) δ 11.96 (br s, 1H), 8.01 (d, J=2.9 Hz, 1H), 7.96 (d, J=8.6 Hz, 1H), 7.88 (d, J=8.6 Hz, 1H), 2.71 (s, 3H); MS (ESI) m/z: 195.2 [M+1]$^+$.

step 2: Following the procedure as described for step 1 of referential example 13, tert-butyl 5-acetyl-3-chloro-1H-pyrrolo[3,2-b]pyridine-1-carboxylate was prepared using 1-(3-chloro-1H-pyrrolo[3,2-b]pyridin-5-yl)ethanone in place of 5-chloro-1H-pyrrolo[3,2-b]pyridine as the starting material: $^1$H NMR (400 MHz, CDCl$_3$) δ 8.48 (d, J=8.5 Hz, 1H), 8.12 (d, J=8.7 Hz, 1H), 7.91 (s, 1H), 2.84 (s, 3H), 1.68 (d, J=6.5 Hz, 9H); MS (ESI) m/z: 295.1 [M+1]$^+$.

step 3: Following the procedures as described in steps 1-3 of referential example 14, hydrochloride was prepared using tert-butyl 5-acetyl-3-chloro-1H-pyrrolo[3,2-b]pyridine-1-carboxylate in place of tert-butyl acetylpyrrolo[3,2-b]pyridine-1-carboxylate: NMR (400 MHz, DMSO-d$^6$) δ 11.90 (br s, 1H), 8.47 (br s, 3H), 7.93 (d, J=8.5 Hz, 1H), 7.90 (d, J=2.9 Hz, 1H), 7.37 (d, J=8.5 Hz, 1H), 4.60 (dt, J=12.4, 6.1 Hz, 1H), 1.56 (d, J=6.8 Hz, 3H); MS (ESI) m/z: 196 [M+1]$^+$.

Referential Example 19

(1-(tetrahydro-2H-pyran-2-yl)-1H-imidazo[4,5-c]pyridin-7-yl)methan-amine and (3-(tetrahydro-2H-pyran-2-yl)-3H-imidazo[4,5-c]pyridin-7-yl)methanamine

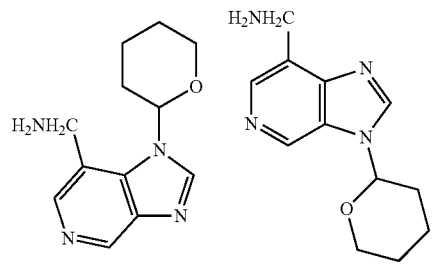

step 1: To a solution of 5-bromopyridine-3,4-diamine (12 g, 63 mmol) in (EtO)$_3$CH (150 mL) was added camphorsulfuric acid (0.5 g). The reaction mixture was heated at reflux for 2 h then the EtOH was distilled to afford a solid. The solid was filtered to afford 9.5 g (75%) 7-bromo-1H-imidazo[4,5-c]pyridine as a white solid; MS (ESI) m/z: 199.0 [M+1]$^+$.

step 2: To a solution of 7-bromo-1H-imidazo[4,5-c]pyridine (3 g, 15.6 mmol) in DMF (10 mL) was added Pd(PPh$_3$)$_4$ (1.0 g) and Zn(CN)$_2$ (1.2 g, 10 mmol). The reaction mixture was irradiated in a microwave at 100° C. for 2 h under Ar. The reaction mixture was poured into aqueous NH$_4$OH and extracted with DCM. The organic extracts were dried (Na$_2$SO$_4$), filtered and concentrated in vacuo. The crude product was purified by SiO$_2$ chromatography to afford 1.5 g (67%) of 3H-imidazo[4,5-c]pyridine-7-carbonitrile as a white solid; MS (ESI)/v/z: 145.0 [M+1]$^+$.

step 3: To the solution of 3H-imidazo[4,5-c]pyridine-7-carbonitrile (1.5 g, 10 mmol) in THF (10 mL) was added 3,4-dihydro-2H-pyran (2 mL) and camphorsulfuric acid (0.1 g), and the reaction mixture was heated at reflux for 2 h. The mixture was poured into water and extracted with EtOAc. The organic extract was dried (Na$_2$SO$_4$), filtered and concentrated in vacuo. The crude product was purified by SiO$_2$ chromatography to afford 1.4 g (60%) of a 1:1 mixture of 1-(tetrahydro-2H-pyran-2-yl)-1H-imidazo[4,5-c]pyridine-7-carbonitrile and 3-(tetrahydro-2H-pyran-2-yl)-3H-imidazo[4,5-c]pyridine-7-carbonitrile as an oil: MS (ESI) m/z: 229.0 [M+1]$^+$.

step 4: To a stirred solution of 1-(tetrahydro-2H-pyran-2-yl)-1H-imidazo[4,5-c]-pyridine-7-carbonitrile and 3-(tetrahydro-2H-pyran-2-yl)-3H-imidazo[4,5-c]pyridine-7-carbonitrile (1.4 g, 6 mmol, 1:1 mixture) in NH$_3$/MeOH (7M, 10 mL) was added Raney-Ni (200 mg). The reaction mixture was stirred under an atmospheric pressure of H$_2$ overnight. The reaction mixture was filtered through a pad of Celite®, and the filtrate was concentrated in vacuo. The crude product was purified by SiO$_2$ chromatography to afford 1.1 g (75%) of a 1:1 mixture of the title compounds as an oil: MS (ESI) m/z: 233.1 [M+1]$^+$.

Referential Example 20

1-(5H-pyrrolo[3,2-d]pyrimidin-2-yl)ethanamine hydrochloride

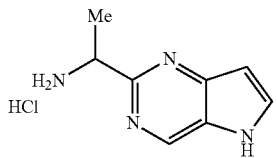 [SMILES: Cl ; CC(N)c1ncc2[nH]ccc2n1]

step 1: Following the procedures as described in steps 1-3 of referential example 13, tert-butyl 2-acetyl-5H-pyrrolo[3,2-d]pyrimidine-5-carboxylate was prepared using 2-chloro-5H-pyrrolo[3,2-d]pyrimidine in place of 5-chloro-1H-pyrrolo[3,2-b]pyridine: $^1$H NMR (400 MHz, CDCl$_3$) δ 9.50 (s, 1H), 8.07 (d, J=3.6 Hz, 1H), 6.93 (d, J=3.7 Hz, 1H), 2.86 (s, 3H), 1.72 (s, 9H); MS (ESI) m/z: 262.2 [M+1]$^+$.

step 2: Following the procedure in step 1 of referential example 14, using tert-butyl 2-acetyl-5H-pyrrolo[3,2-d]pyrimidine-5-carboxylate in place of tert-butyl 5-acetylpyrrolo[3,2-b]pyridine-1-carb oxylate, (R)-ethyl 2-(1-(tert-butylsulfinylimino)ethyl)-5H-pyrrolo[3,2-d]pyrimidine-5-carboxylate was obtained: $^1$H NMR (400 MHz, CDCl$_3$) δ 9.49 (s, 1H), 8.05 (d, J=3.6 Hz, 1H), 6.89 (d, J=3.1 Hz, 1H), 4.59 (q, J=7.2 Hz, 2H), 2.99 (s, 3H), 1.52 (t, J=7.1 Hz, 3H), 1.37 (s, 9H); MS (ESI) m/z: 337.3 [M+1]$^+$.

step 3: To (R)-ethyl 2-(1-(tert-butylsulfinylimino)ethyl)-5H-pyrrolo[3,2-d]pyrimidine-5-carboxylate (259.0 mg, 0.77 mmol) in anhydrous THF (5 mL) at 0° C. was added dropwise L-selectride (1.0 mol/L) in THF (1.2 mL). The resultant orange reaction mixture was warmed to RT and stirred under N$_2$ for 16 h. The solvent was removed in vacuo and the crude was partitioned between EtOAc and water. The organic layer was washed with sat'd. aq. NaHCO$_3$, water and brine, dried (Na$_2$SO$_4$), filtered, and concentrated in vacuo. The crude was purified by SiO$_2$ chromatography eluted with a mixture of EtOAc containing 1% TEA and MeOH to afford 180.0 mg (87.8%) of (R)—N-(1-(5H-pyrrolo[3,2-d]pyrimidin-2-yl)ethyl)-2-methylpropane-2-sulfinamide as racemic mixture. MS (ESI) m/z: 267 [M+1]$^+$.

step 4: Following the procedure in step 3 f referential example 14, 1-(5H-pyrrolo[3,2-d]pyrimidin-2-yl)ethanamine hydrochloride was prepared using (R)—N-(1-(5H-pyrrolo[3,2-d]pyrimidin-2-yl)ethyl)-2-methylpropane-2-sulfinamide in place of (R)—N—((S)-1-(1H-pyrrolo[3,2-b]pyridin-5-yl)ethyl)-2-methylpropane-2-sulfinamide: $^1$H NMR (400 MHz, DMSO-d$^6$) δ 12.26 (br s, 1H), 9.02 (s, 1H), 8.54 (br s, 3H), 8.07 (t, J=3.0 Hz, 1H), 6.68 (s, 1H), 4.58 (dt, J=12.4, 6.0 Hz, 1H), 1.60 (d, J=6.9 Hz, 3H); MS (ESI) m/z: 163.3 [M+1]$^+$.

Referential Example 21

(2-methyl-1-((2-(trimethylsilyl)ethoxy)methyl)-1H-imidazo[4,5-c]pyridin-7-yl)methanamine and (2-methyl-3-((2-(trimethylsilyl)ethoxy)methyl)-3H-imidazo[4,5-c]pyridin-7-yl)methanamine

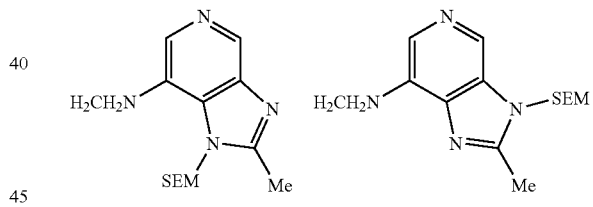

step 1: A mixture of 5-bromopyridine-3,4-diamine (20 g, 107 mmol) and (EtO)$_3$CMe (100 mL) in HOAc (40 mL) was stirred and heated at reflux for 2 h then the EtOH was removed by distillation to afford a solid. The solid was filtered to give 15 g (52%) of 7-bromo-2-methyl-1H-imidazo-[4,5-c]pyridine acetate as a light yellow solid: MS (ESI) m/z: 212 [M+1]$^+$.

step 2: To a solution of 7-bromo-2-methyl-1H-imidazo-[4,5-c]pyridine acetate (10 g, 37 mmol) in anhydrous THF (200 mL) was added sodium hydride (4.5 g, 120 mmol) portionwise at 0° C. After stirring at 0° C. for 0.5 h, SEMCl (9.1 g, 55.5 mmol) was added. The reaction mixture was stirred at RT for 5 h and then poured into water. The mixture was extracted with EtOAc. The organic layers were dried (Na$_2$SO$_4$), filtered, and concentrated in vacuo. The crude product was purified by SiO$_2$ chromatography to afford 8.0 g (63%) of a 1:1 mixture of 7-bromo-2-methyl-1-((2-(trimethylsilyl)ethoxy)methyl)-1H-imidazo[4,5-c]pyridine and 7-bromo-2-methyl-3-((2-(trimethylsilyl)ethoxy)methyl)-3H-imidazo[4,5-c]pyridine as an oil: MS (ESI) m/z: 342/344 [M+1]$^+$.

step 3: Following the procedure in step 2 of referential example 19, a 1:1 mixture of 2-methyl-1-((2-(trimethylsilyl)ethoxy)methyl)-1H-imidazo[4,5-c]pyridine-7-carbonitrile and 2-methyl-3-((2-(trimethylsilyl)ethoxy)methyl)-3H-imidazo[4,5-c]pyridine-7-carbonitrile was prepared using a 1:1 mixture of 7-bromo-2-methyl-1-((2-(trimethylsilyl)ethoxy)methyl)-1H-imidazo[4,5-c]pyridine and 7-bromo-2-methyl-3-((2-(trimethylsilyl)ethoxy)methyl)-3H-imidazo[4,5-c]pyridine in place of 7-bromo-1H-imidazo[4,5-c]pyridine: MS (ESI) m/z: 289.1 [M+1]⁺.

Following the procedure in step 4 of referential example 19, (2-methyl-1-((2-(trimethylsilyl)ethoxy)methyl)-1H-imidazo[4,5-c]pyridin-7-yl)methanamine and (2-methyl-3-((2-(trimethylsilyl)ethoxy)methyl)-3H-imidazo[4,5-c]pyridin-7-yl)methanamine (1:1 mixture) were prepared using 7-bromo-2-methyl-1-((2-(trimethylsilyl)ethoxy)methyl)-1H-imidazo[4,5-c]pyridine and 7-bromo-2-methyl-3-((2-(trimethylsilyl)ethoxy)methyl)-3H-imidazo[4,5-c]pyridine (1:1 mixture) in place of 1-(tetrahydro-2H-pyran-2-yl)-1H-imidazo[4,5-c]-pyridine-7-carbonitrile and 3-(tetrahydro-2H-pyran-2-yl)-3H-imidazo[4,5-c]pyridine-7-carbonitrile: MS (ESI) m/z: 293.2 [M+1]⁺.

Referential Example 22

1-(6-Chloro-1-tosyl-1H-pyrrolo[3,2-b]pyridin-5-yl)ethanamine

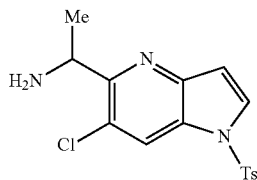 [SMILES: Cc1ccc(S(=O)(=O)n2ccc3nc(C(C)N)c(Cl)cc32)cc1]

step 1: To a solution of 6-chloro-1H-pyrrolo[3,2-b]pyridine (5.0 g, 32.8 mmol) in THF (150 mL) in an ice bath was added NaH (1.57 g, 60% in mineral oil, 39.3 mmol). After stirring in an ice bath for 30 min, 4-toluenesulfonyl chloride (6.87 g, 36.1 mmol) was added. The mixture was stirred at RT overnight. The reaction mixture was quenched with water (50 mL) at 0° C. and extracted with EtOAc (300 mL). The extract was dried (Na₂SO₄), filtered, and concentrated under reduced pressure. The crude product was purified by SiO₂ chromatography eluting with petroleum ether/EtOAc gradient (8:1 to 2:1) to afford 6-chloro-1-tosyl-1H-pyrrolo[3,2-b]pyridine as a yellow solid (8.5 g, 84%). MS (ESI): m/z=307.0 [M+1]⁺.

step 2: To a solution of 6-chloro-1-tosyl-1H-pyrrolo[3,2-b]pyridine (8.5 g, 27.7 mmol) in CH₂Cl₂ (150 mL) in an ice bath was added m-chloroperbenzoic acid (85%, 8.4 g, 41.6 mmol). The mixture was stirred at RT for two h. The reaction mixture was quenched by saturated sodium thiosulphate solution. The organic layer was washed with saturated NaHCO₃ solution and water, dried (Na₂SO₄) filtered, and concentrated under reduced pressure to afford 8.75 g (90%) of 6-chloro-1-tosyl-1H-pyrrolo[3,2-b]pyridine-4-oxide as a yellow solid. MS (ESI): m/z=323.0 [M+1]⁺.

step 3: To a solution of 6-chloro-1-tosyl-1H-pyrrolo[3,2-b]pyridine-4-oxide (8.75 g, 27.12 mmol) in 1,2-dichloroethane (250 mL) was added dimethylcarbamic chloride (4.37 g, 40.66 mmol) and trimethylsilyl cyanide (4.03 g, 40.66 mmol) successively. The mixture was stirred under nitrogen at 80° C. overnight. The reaction mixture was quenched by adding sat'd. aq. NaHCO₃ solution. The organic layer was washed with water (50 mL×3), dried (Na₂SO₄), filtered, and concentrated in vacuo. The crude product was purified by SiO2 chromatography eluting with petroleum ether EtOAc (8:1) to afford 4.8 g (53%) of 6-chloro-1-tosyl-1H-pyrrolo[3,2-b]pyridine-5-carbonitrile as a white solid. MS (ESI): m/z=332.0 [M+1]⁺.

step 4: To a solution of 6-chloro-1-tosyl-1H-pyrrolo[3,2-b]pyridine-5-carbonitrile (2.5 g, 7.54 mmol) in THF (50 mL) at −10° C. under nitrogen atmosphere was slowly added a solution of MeMgCl in THF (3 M, 12.6 mL, 37.7 mmol). The mixture was stirred at 0° C. for 1.5 h and then was quenched with sat'd. aq. NH₄Cl solution (20 mL). The reaction mixture was partitioned between EtOAc (300 mL) and water (50 mL). The organic layer was separated, washed with brine, dried (NaSO₄), filtered, and concentrated under reduced pressure. The residue was purified by SiO₂ chromatography eluting with petroleum ether/EtOAc (8:1) to afford 1-(6-chloro-1-tosyl-1H-pyrrolo[3,2-b]pyridin-5-yl)ethanone as white solid (480 mg, 18%). MS (ESI): m/z=349.0 [M+1]⁺.

step 5: A mixture of 1-(6-chloro-1-tosyl-1H-pyrrolo[3,2-b]pyridin-5-yl)ethanone (480 mg, 1.38 mmol), hydroxylamine hydrochloride (478 mg, 6.88 mmol), NaOAc (1.13 g, 13.76 mmol) in EtOH (10 mL) was stirred at RT overnight. The reaction mixture was filtered and the filtrate concentrated under reduced pressure. The residue was purified by SiO₂ chromatography eluting with petroleum ether/EtOAc (4:1) to afford 514 mg (94%) of 1-(6-chloro-1-tosyl-1H-pyrrolo[3,2-b]pyridin-5-yl)ethanone oxime as white solid. MS (ESI): m/z=364.0 [M+1]⁺.

step 6: A mixture of 1-(6-chloro-1-tosyl-1H-pyrrolo[3,2-b]pyridin-5-yl)ethanone oxime (514 mg, 1.41 mmol), Zn power (4.6 g, 70.64 mmol), NH₄Cl (1.5 g, 28.26 mmol) in MeOH (20 mL) and HOAc (4 mL) was heated at reflux overnight. The reaction mixture was filtered and the filtrate concentrated under reduced pressure. The residue was diluted with CH₂Cl₂ (200 mL) and aqueous ammonia (20 mL). The organic layer was separated, washed with H₂O, dried (NaSO₄), filtered, and concentrated under reduced pressure. The crude product was purified by SiO₂ chromatography eluting with MeOH—CH₂Cl₂ (1:15) to afford 385 mg (78%) of 1-(6-chloro-1-tosyl-1H-pyrrolo[3,2-b]pyridin-5-yl)ethanamine as yellow oil. MS (ESI): m/z=350.0 [M+1]⁺.

Referential Example 23

1-(6-Fluoro-1-tosyl-1H-pyrrolo[3,2-b]pyridin-5-yl)ethanamine

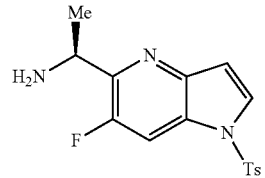 [SMILES: Cc1ccc(S(=O)(=O)n2ccc3nc([C@H](C)N)c(F)cc32)cc1]

step 1: A suspension of 2-bromo-5-fluoro-3-nitropyridine (4.42 g, 20 mmol) and SnCl₂ (22.56 g, 100 mmol) in EtOH (40 mL) and concentrated HCl (40 mL) was heated at 60° C. for 1 h. The reaction mixture was concentrated under reduced pressure. To the residue was added EtOAc (100 mL) and sat'd aq. NaHCO₃ solution (200 mL), and the mixture was filtered with Celite® and extracted with EtOAc (100 mL×3). The organic layer was washed with saturated NaHCO₃, water and brine, dried (MgSO₄), filtered, and concentrated under reduced pressure to afford 3.1 g (80%) of 2-bromo-5-fluoro-pyridin-3-amine as a brown solid. MS (ESI): m/z=191.1 [M+1]$^+$.

step 2: To a mixture of 2-bromo-5-fluoropyridin-3-amine (3.3 g, 17.3 mmol), TEA (7.3 mL, 51.9 mmol), PdCl$_2$(PPh$_3$)$_2$ (1.2 g, 1.73 mmol), and Cu(I)I (0.33 g, 1.73 mmol) in THF (50 mL) at 0° C. under nitrogen was added a solution of (trimethylsilyl)acetylene (3.39 mL, 34.6 mmol). The mixture was stirred at RT for 2 h and then concentrated under reduced pressure. The residue was purified by SiO2 chromatography eluting with petroleum ether/EtOAc (5:1) to afford 2.0 g (915) of 5-fluoro-2-((trimethylsilyl)ethynyl)pyridin-3-amine as a yellow solid. MS (ESI): m/z=209.1 [M+1]$^+$.

step 3: To a solution of 5-fluoro-2-((trimethylsilyl)ethynyl)pyridin-3-amine (2.22 g, 10.7 mmol) in DMF (30 mL) at 0° C. under nitrogen was added NaH (60% in mineral oil, 1.025 g, 42.7 mmol) in several portions. After stirring at RT for 2 h, the reaction mixture was poured into ice-cold water and extracted with EtOAc. The extract was dried (MgSO$_4$), filtered, and concentrated under reduced pressure to afford 1.46 g (100%) of 6-fluoro-1H-pyrrolo[3,2-b]pyridine as a brown solid. MS (ESI): m/z=137.2 [M+1]$^+$.

step 4: To a solution of 6-fluoro-1H-pyrrolo[3,2-b]pyridine (9.52 g, 70 mmol) in THF (150 mL) at 0° C. was added NaH (60% in mineral oil, 2.02 g, 84 mmol) in three portions. After stirring at RT for 30 min, the mixture was cooled to 0° C. and p-TsCl (14.7 g, 77 mmol) was added. The reaction mixture was stirred for 3 h and the temperature was slowly raised to RT. The reaction mixture was poured into ice-cold water and a precipitate was formed. The precipitate was collected by filtration. The crude product was purified by SiO$_2$ chromatography eluting with DCM to afford 18 g (80%) of 6-fluoro-1-tosyl-1H-pyrrolo[3,2-b]pyridine as a solid. MS (ESI): m/z=291.1 [M+1]$^+$.

step 5: To a solution of 6-fluoro-1-tosyl-1H-pyrrolo[3,2-b]pyridine (18 g, 62 mmol) in DCM (300 mL) was added MCPBA (16 g, 93 mmol). The mixture was stirred at RT overnight and then concentrated under reduced pressure. The residue was purified by SiO$_2$ chromatography eluting with DCM:MeOH (30:1) to afford 23 g (100%) of 6-fluoro-1-tosyl-1H-pyrrolo[3,2-b]pyridine 4-oxide as a solid. MS (ESI) m/z: 307.1 [M+1]$^+$.

step 6: To a solution of 6-fluoro-1-tosyl-1H-pyrrolo[3,2-b]pyridine 4-oxide (2.4 g, 7.84 mmol) in 1,2-dichloroethane (60 mL) was added dimethylcarbamic chloride (1.3 g, 11.76 mmol), followed by addition of trimethylsilyl cyanide (1.2 g, 11.76 mmol). The mixture was stirred under nitrogen at 80° C. overnight. The resulting mixture was quenched by addition of a sat'd aq. NaHCO$_3$ solution. The organic layer was washed with H$_2$O (50 mL×3) and concentrated under reduced pressure. The crude product was purified by SiO$_2$ chromatography eluting with petroleum ether/EtOAc (4:1) as eluent to afford 1.1 g (44.5%) of 6-fluoro-1-tosyl-1H-pyrrolo[3,2-b]pyridine-5-carbonitrile. MS (ESI) m/z: 316.1 [M+1]$^+$.

step 7: To a solution of 6-fluoro-1-tosyl-1H-pyrrolo[3,2-b]pyridine-5-carbonitrile (0.5 g, 1.6 mmol) in anhydrous THF (10 mL) at 0° C. under nitrogen was added dropwise a solution of MeMgCl in THF (3.0 M, 1.6 mL, 4.8 mmol). After stirring at 0° C. for 1 h, the reaction mixture was poured into aqueous NH$_4$Cl and extracted with EtOAc (50 mL×3). The combined extracts were washed with brine, dried (Na$_2$SO$_4$), filtered and concentrated under reduced pressure. The residue was purified by SiO$_2$ chromatography eluting with petroleum ether:EtOAc (1:1) to afford 0.3 g (40%) of 1-(6-fluoro-1-tosyl-1H-pyrrolo[3,2-b]pyridin-5-yl)ethanone as yellow solid. MS (ESI): m/z=333.1 [M+1]$^{4"}$.

step 8: A mixture of 1-(6-fluoro-1-tosyl-1H-pyrrolo[3,2-b]pyridin-5-yl)ethanone (0.7 g, 2.118 mmol), NaOAc (1.73 g, 21.1 mmol), and hydroxylamine hydrochloride (0.735 g, 10.55 mmol) in EtOH (20 mL) was heated at 60° C. for 1 h. The reaction mixture was concentrated under reduced pressure, water (200 mL) was added, and the mixture was extracted with EtOAc (50 mL×3). The combined extracts were concentrated under reduced pressure to afford 0.66 mg (90%) of 1-(6-fluoro-1-tosyl-1H-pyrrolo[3,2-b]pyridin-5-yl)ethanone oxime as a white solid. MS (ESI): m/z=348.2 [M+1]$^+$.

step 9: A mixture of 1-(6-fluoro-1-tosyl-1H-pyrrolo[3,2-b]pyridin-5-yl)ethanone oxime (0.75 mg, 2.16 mmol), zinc powder (7.06 g, 108 mmol), and NH$_4$Cl (2.31 g, 43.2 mmol) in MeOH (30 mL) and HOAc (6 mL) was heated at 60° C. for 2 h. The reaction mixture was filtered and the filtrate concentrated under reduced pressure. The residue was suspended in ammonia solution (50 mL) and extracted with DCM (50 mL×3). The combined extracts were dried (MgSO$_4$), filtered, and concentrated under reduced pressure. The crude was purified by SiO$_2$ chromatography eluting with DCM/MeOH/Et$_3$N to afford 0.5 g (97.7%) of 1-(6-fluoro-1-tosyl-1H-pyrrolo[3,2-b]pyridin-5-yl)ethanamine as a yellow solid. MS (ESI): m/z=334.3 [M+1]$^+$.

Referential Example 24

(6-Fluoro-1-((2-(trimethylsilyl)ethoxy)methyl)-1H-pyrrolo[3,2-b]pyridin-5-yl)-N-methylmethanamine

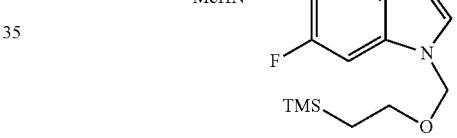

step 1: To a solution of 6-fluoro-1-tosyl-1H-pyrrolo[3,2-b]pyridine-5-carbonitrile (2742 mg, 7.85 mmol) in MeOH (20 mL) and water (20 mL) was added NaOH (628 mg 15.7 mmol). The mixture was stirred at RT for 1 h. The reaction mixture was quenched by adding a sat'd aq. NH$_4$Cl and extracted with EtOAc. The extract was dried (MgSO$_4$), filtered, and concentrated under reduced pressure. The residue was purified by SiO$_2$ chromatography eluting with a petroleum ether:EtOAc gradient (10:1-0:1) to afford 758 mg (60%) of 6-fluoro-1H-pyrrolo[3,2-b]pyridine-5-carbonitrile. MS (ESI): m/z=162.3 [M+1]$^+$.

step 2: To a solution of 6-fluoro-1H-pyrrolo[3,2-b]pyridine-5-carbonitrile (758 mg, 4.71 mmol) in THF (20 mL) was added NaH (60% in mineral oil, 452 mg, 9.42 mmol). After stirring for 30 min, SEM-Cl (1527 mg, 9.42 mmol) was added, followed by stirring at RT for 16 h. The reaction mixture was quenched by adding sat'd aq.NH$_4$Cl and extracted with EtOAc (100 mL×2). The combined extracts were dried (MgSO$_4$), filtered, and concentrated under reduced pressure. The residue was purified by SiO$_2$ chromatography eluting with a petroleum ether:EtOAc gradient (10:1-0:10) to afford 1096 mg (80%) of 6-fluoro-1-((2-(trimethylsilyl)-ethoxy)methyl)-1H-pyrrolo[3,2-b]pyridine-5-carbonitrile. MS (ESI): m/z=292.1[M+1]$^+$.

step 3: To a solution of 6-fluoro-1-((2-(trimethylsilyl)ethoxy)methyl)-1H-pyrrolo[3,2-b]pyridine-5-carbonitrile (1096 mg, 3.77 mmol) in a solution of NH$_3$/MeOH (7 N, 100 mL) was added Raney nickel (1000 mg), followed by stirring under a hydrogen atmosphere overnight. The reaction mixture was filtered and the filtrate concentrated under reduced pressure to afford (6-fluoro-1-((2-(trimethylsilyl)ethoxy)methyl)-1H-pyrrolo[3,2-b]pyridin-5-yl)methanamine (1000 mg, 90%). MS (ESI): m/z=296.1 [M+1]$^+$.

step 4: To a mixture of (6-fluoro-1-((2-(trimethylsilyl)ethoxy)methyl)-1H-pyrrolo[3,2-b]pyridin-5-yl)methanamine (1000 mg, 3.39 mmol) in THF (20 mL) and DMF (1 mL) was added (Boc)$_2$O (888 mg, 4.07 mmol) and TEA (1027 mg, 10.3 mmol). The mixture was stirred at RT for 3 h. The reaction mixture was quenched by water and extracted by EtOAc (100 mL×2). The combined extracts were dried (MgSO$_4$), filtered, and concentrated under reduced pressure. The residue was purified by SiO$_2$ chromatography eluting with a petroleum ether:EtOAc gradient (10:1-5:1) to afford 1.50 g (80%) tert-butyl (6-fluoro-1-((2-(trimethylsilyl)ethoxy)methyl)-1H-pyrrolo[3,2-b]pyridin-5-yl)methylcarbamate as a brown oil. MS (ESI): m/z=396.3 [M+1]$^+$.

step 5: To a mixture of tert-butyl (6-fluoro-1-((2-(trimethylsilyl)ethoxy)methyl)-1H-pyrrolo[3,2-b]pyridin-5-yl)methylcarbamate (300 mg, 0.75 mmol) in THF (5 mL) was added NaH (60% dispersion in mineral oil, 110 mg, 2.25 mmol). After stirring at RT for 30 min, CH$_3$I (320 mg, 2.25 mmol) was added, followed by stirring at RT for 3 h. The reaction mixture was quenched by adding a sat'd. aq.solution of NH$_4$Cl and extracted with EtOAc (30 mL×2). The combined extracts were dried (MgSO$_4$), filtered, and concentrated under reduced pressure. The residue was purified by SiO$_2$ chromatography eluting with a petroleum ether:EtOAc gradient (10:1 to 1:1) to afford 200 mg (66.6%) of tert-butyl (6-fluoro-1-((2-(trimethylsilyl)ethoxy)methyl)-1H-pyrrolo[3,2-b]pyridin-5-yl)methyl(methyl)carbamate as a brown oil. MS (ESI): m/z=410.3 [M+1]$^+$.

step 6: A mixture of tert-butyl (6-fluoro-1-((2-(trimethylsilyl)ethoxy)methyl)-1H-Pyrrolo[3,2-b]pyridin-5-yl)methyl(methyl)carbamate (200 mg, 0.5 mmol) in CH$_2$Cl$_2$ (5 mL) and TFA (0.5 mL) was stirred at RT for 2 h. The reaction mixture was cooled to 0° C. and then quenched by adding a sat'd. aq. NaHCO$_3$ until the pH was about 8. The mixture was extracted with EtOAc (20 mL×2), and the combined extracts dried (MgSO$_4$), filtered and concentrated under reduced pressure to afford 120 mg (70%) of (6-fluoro-1-((2-(trimethylsilyl)ethoxy)methyl)-1H-pyrrolo[3,2-b]pyridin-5-yl)-N-methylmethanamine as a brown oil. MS (ESI): m/z=310.3 [M+1]$^+$.

Referential Example 25

1-(3-(4-Methoxybenzyl)-3H-imidazo[4,5-c]pyridin-6-yl)ethanamine

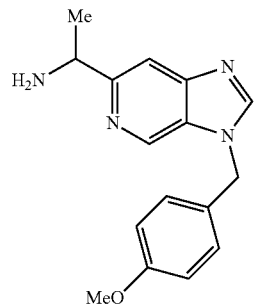 [SMILES: COc1ccc(Cn2cnc3cc(C(C)N)ncc32)cc1]

step 1: To a solution of 2-chloro-5-nitropyridin-4-amine (4.50 g, 25.93 mmol) in EtOAc (100 mL) was added Raney nickel (0.45 g) followed by stirring under hydrogen at RT for 2 h. The reaction mixture was filtered and the filtrate concentrated under reduced pressure to afford 4.00 g (ca. 100%) of crude 6-chloropyridine-3,4-diamine as yellow oil. MS (ESI): m/z=144.3 [M+1]$^+$.

step 2: A mixture of 6-chloropyridine-3,4-diamine (4.00 g, 27.86 mmol) in formic acid (20.0 mL) was heated at reflux overnight. The reaction mixture was concentrated under reduced pressure to give a brown oil, which was partitioned between EtOAc (300 mL) and a sat'd aq NaHCO$_3$ (100 mL). The organic layer was dried (MgSO$_4$), filtered and concentrated under reduced pressure. The residue was purified by SiO$_2$ chromatography eluting with a MeOH/DCM gradient (6% to 9% MeOH) to afford 3.5 g (82%) of 6-chloro-3H-imidazo[4,5-c]pyridine as white solid, MS (ESI): m/z=154.1 [M+1]$^+$.

step 3: To a solution of 6-chloro-3H-imidazo[4,5-c]pyridine (3.50 g, 22.79 mmol) in THF (50 mL) at 0° C. was slowly added sodium hydride (60% dispersion in mineral oil, 1.82 g, 45.58 mmol) in several portions. After stirring at RT for 30 min, 1-(chloromethyl)-4-methoxybenzene (4.30 g, 27.48 mmol) was added and the mixture was stirred at RT for 2 h. The reaction mixture was poured into water (100 mL) and extracted with EtOAc (100 mL×2). The combined extracts were washed with water (100 mL) and brine (50 mL), dried (MgSO$_4$), filtered and evaporated under reduced pressure. The residue was purified by SiO2 chromatography eluting with hexane/EtOAc (1:1) to afford 5.0 g (80%) of 6-chloro-3-(4-methoxybenzyl)-3H-imidazo[4,5-c]pyridine as a white solid. MS (ESI): m/z=274.2 [M+1]$^+$.

step 4: A mixture of 6-chloro-3-(4-methoxybenzyl)-3H-imidazo[4,5-c]pyridine (500 mg, 1.83 mmol), tributyl(1-ethoxyvinyl)stannane (866 mg, 2.40 mmol), Pd (PPh$_3$)$_4$ (243 mg, 0.27 mmol) in NMP (10 mL) was heated at 140° C. for 72 h. The reaction mixture was quenched with water and extracted with EtOAc (50 mL×3). The combined extracts were washed with water (100 mL) and brine (50 mL), dried (MgSO$_4$) filtered and concentrated under reduced pressure. The residue was purified by SiO$_2$ chromatography eluting with 3% MeOH/DCM to afford 440 mg (78%) of 6-(1-ethoxyvinyl)-3-(4-methoxybenzyl)-3H-imidazo[4,5-c]pyridine as a gray solid. MS (EST): m/z=310.3 [M+1]$^+$.

step 5: A mixture of 6-(1-ethoxyvinyl)-3-(4-methoxybenzyl)-3H-imidazo[4,5-c]pyridine (440 mg, 1.42 mmol) in MeOH (2 mL) was added an aqueous solution of HCl (1N, 0.5 mL) and stirred at RT for 30 min. To the reaction mixture was added an aqueous ammonia solution (35%) until the pH was approximately 8. The aqueous solution was extracted with EtOAc (50 mL×3). The combined extracts were washed with water and brine, dried (MgSO$_4$), filtered, and concentrated under reduced pressure. The residue was purified by SiO$_2$ chromatography eluting with petroleum ether:EtOAc (1:1) to afford 300 mg (75%) of 1-(3-(4-methoxybenzyl)-3H-imidazo[4,5-c]pyridin-6-yl)ethanone as a white solid. MS (ESI): m/z=282.3 [M+1]$^+$.

step 6: To a mixture of 1-(3-(4-methoxybenzyl)-3H-imidazo[4,5-c]pyridin-6-yl)ethanone (500 mg, 1.78 mmol) and NaOAc (1.21 g, 17.80 mmol) in MeOH (10 mL) at RT was added hydroxylamine hydrochloride (618 mg, 8.90 mmol). The reaction was stirred at RT for 2 h. The reaction mixture was concentrated under reduced pressure. To the residue was added water (100 mL) followed by extraction with EtOAc (50 mL×3). The combined extracts were dried (MgSO$_4$), filtered and concentrated under reduced pressure to afford 320 mg (61%) of 1-(3-(4-methoxybenzyl)-3H-imidazo[4,5-c]pyridin-6-yl)ethanone oxime as a yellow solid. MS (ESI): m/z=297.2 [M+1]$^+$.

step 7: A mixture of 1-(3-(4-methoxybenzyl)-3H-imidazo[4,5-c]pyridin-6-yl)ethanone oxime (320 mg, 1.08 mmol), zinc (3.53 g, 54.00 mmol), and ammonium chloride (2.89 g, 54.00 mmol) in MeOH (10 mL) and HOAc (2 mL) was heated at 60° C. for 4 h. The reaction mixture was filtered and the filtrate was concentrated under reduced pressure. To the residue was added an aqueous solution of ammonia (50 mL) and the resulting mixture was extracted with DCM (50 mL×3). The combined extracts were dried (MgSO$_4$), filtered and concentrated under reduced pressure. The residue was purified by SiO$_2$ chromatography eluting with CH$_2$Cl$_2$:MeOH:Et$_3$N (10:1:0.2) to afford 200 mg (66%) of 1-(3-(4-methoxybenzyl)-3H-imidazo[4,5-c]pyridin-6-yl)ethanamine as a colorless oil. MS (ESI): m/z=283.2[M+1]$^+$.

Referential Example 26

N-Methyl(1-((2-(trimethylsilyl)ethoxy)methyl)-1H-pyrrolo[2,3-c]pyridin-4-yl)methanamine

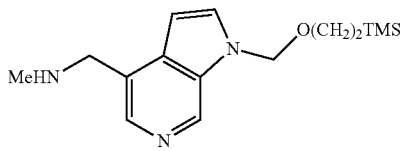

step 1: To a solution of 4-bromo-1H-pyrrolo[2,3-c]pyridine (1.0 g, 5.08 mmol) in NMP (20 mL) under an argon atmosphere was added Zn(CN)$_2$ (1.19 g, 10.15 mmol) and Pd(PPh$_3$)$_4$ (0) (590 mg, 0.51 mmol). The mixture was heated at 100° C. for 18 h. The reaction mixture was partitioned between EtOAc (300 mL) and water (50 mL). The organic layer was washed with brine, dried (MgSO$_4$), filtered and concentrated under reduced pressure. The residue was purified by SiO$_2$ chromatography eluting with petroleum ether: EtOAc (1:1) to afford 618 mg (85.1%) of 1H-pyrrolo[2,3-c]pyridine-4-carbonitrile as yellow solid. MS (ESI): m/z=144.3 [M+1]$^+$.

step 2: To a solution of 1H-pyrrolo[2,3-c]pyridine-4-carbonitrile (618 mg, 4.32 mmol) in anhydrous THF (30 mL) at 0° C. was slowly added NaH (60% in mineral oil, 346 mg, 8.64 mmol). After stirring at 0° C. for 30 min, (2-(chloromethoxy)ethyl)trimethylsilane (865 mg, 5.19 mmol) was added followed by stirring at RT for 1 h. The reaction mixture was quenched with ice water (50 ml) and extracted with EtOAc (50 mL×3). The combined extracts were dried over (MgSO$_4$) filtered, and concentrated under reduced pressure. The residue was purified by SiO$_2$ chromatography eluting with petroleum ether:EtOAc (3:1) to afford 683 mg (57.9%) of 1-((2-(trimethylsilyl)ethoxy)methyl)-1H-pyrrolo[2,3-c]pyridine-4-carbonitrile as a yellow solid. MS (ESI): m/z=274.2 [M+1]$^+$.

step 3: To a solution of 1-((2-(trimethylsilyl)ethoxy)methyl)-1H-pyrrolo[2,3-c]pyridine-4-carbonitrile (683 mg, 2.5 mmol) in a solution of NH$_3$/MeOH (7 N, 20 mL) was added Raney nickel (300 mg). The mixture was stirred under hydrogen for 3 h. The reaction mixture was filtered and the filtrate concentrated under reduced pressure to afford 673 mg (97.1%) of (1-((2-(trimethylsilyl)ethoxy)methyl)-1H-pyrrolo[2,3-c]pyridin-4-yl)methanamine as a yellow oil. MS (ESI): m/z=278.1 [M+1]$^+$.

step 4: To a mixture of (1-((2-(trimethylsilyl)ethoxy)methyl)-1H-pyrrolo[2,3-c]pyridin-4-yl)methanamine (400 mg, 1.44 mmol) and TEA (436 mg, 4.33 mmol) in DCM (50 mL) was added at RT di-tert-butyl dicarbonate (468 mg, 2.17 mmol) followed by stirring for 18 h. The reaction mixture was concentrated under reduced pressure. The residue was purified by SiO$_2$ chromatography eluting with petroleum ether: EtOAc (2:1) to afford 312 mg (57.2%) of tert-butyl (1-((2-(trimethylsilyl)ethoxy)methyl)-1H-pyrrolo[2,3-c]pyridin-4-yl)methylcarbamate as a yellow solid. MS (ESI): m/z=378.3 [M+1]$^+$.

step 5: To a solution of tert-butyl (1-((2-(trimethylsilyl)ethoxy)methyl)-1H-pyrrolo[2,3-c]pyridin-4-yl)methylcarbamate (300 mg, 0.796 mmol) in anhydrous THF (30 mL) at 0° C. was slowly added NaH (60% in mineral oil, 48 mg, 1.194 mmol) and stirred at 0° C. for 30 min. To the mixture was added methyl 4-methylbenzenesulfonate (178 mg, 0.955 mmol) followed by stirring at RT for 18 h. The reaction mixture was quenched with water (100 mL) and extracted with EtOAc (50 mL×3). The combined extracts were dried (MgSO$_4$), filtered, and concentrated under reduced pressure. The residue was purified by SiO$_2$ chromatography eluting with petroleum ether:EtOAc (2:1) to afford 232 mg (74.6%) of tert-butyl methyl((1-((2-(trimethylsilyl)ethoxy)methyl)-1H-pyrrolo[2,3-c]pyridin-4-yl)methyl)carbamate as a yellow solid. MS (ESI): m/z=392.2 [M+1]$^+$.

step 6: A solution of tert-butyl methyl((1-((2-(trimethylsilyl)ethoxy)methyl)-1H-pyrrolo[2,3-c]pyridin-4-yl)methyl)carbamate (232 mg, 0.593 mmol) in DCM (20 mL) and TFA (10 mL) was stirred at RT for 3 h. The reaction mixture was quenched with water (100 mL) and extracted with DCM (50 mL×3). The combined extracts were dried (MgSO$_4$), filtered, and concentrated under reduced pressure to afford 132 mg (76.4%) of N-methyl(1-((2-(trimethylsilyl)ethoxy)methyl)-1H-pyrrolo[2,3-c]pyridin-4-yl)methanamine as a yellow solid. MS (ESI): m/z=292.2 [M+1]$^+$.

Referential Example 27

N-ethyl-1-(5-((2-(trimethylsilyl)ethoxy)methyl)-5H-pyrrolo[3,2-d]pyrimidin-2-yl)ethanamine

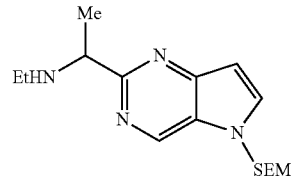

step 1: To a stirred mixture of sodium hydride (12.5 g, 520 mmol, 60% in mineral oil) in anhydrous THF (300 mL) at 0° C. was added dropwise 2-chloro-5H-pyrrolo[3,2-d]pyrimidine (40.0 g, 262 mmol) dissolved in anhydrous THF (200 mL). The reaction mixture was stirred at 0° C. for 15 min them SEMCl (52.5 g, 315 mmol) was added dropwise. The mixture was then stirred at RT for 1 h and then diluted with EtOAc. The organic layer was washed with water and brine, dried over (Na$_2$SO$_4$), filtered and concentrated under reduced pressure. The crude product was purified by SiO$_2$ chromatography to afford 42 g (56.4%) of 2-chloro-5-((2-(trimethylsilyl)ethoxy)methyl)-5H-pyrrolo[3,2-d]pyrimidine as an orange oil. A high-pressure tube charged with 2-chloro-5-((2-(trimethylsilyl)ethoxy)methyl)-5H-pyrrolo[3,2-d]pyrimidine (2.23 g, 7.90 mmol), tributyl(1-ethoxyvinyl)stannane (3.7 g, 10.27 mmol), and Pd(PPh$_3$)$_2$Cl$_2$ (200 mg) in degassed DMF (20 mL) under N$_2$ was sealed and heated at 100° C. for 16 h. The reaction mixture was cooled, diluted with EtOAc, and filtered through a pad of Celite® to remove Pd solid. The filtrate was washed with water and brine, dried (Na$_2$SO$_4$), filtered, and concentrated under reduced pressure. The crude product was dissolved in anhydrous THF (0.3 M), and 2N HCl (5.0 eq.) was added. The reaction mixture was stirred at RT under N$_2$ for 16 h, poured into 10% aq. NaOH solution, and then extracted with EtOAc. The organic layer was washed with water and brine, dried (Na$_2$SO$_4$), filtered, and concentrated under reduced pressure. The crude product was purified by SiO$_2$ chromatography to afford 1.5 g (66%) of 1-(5-((2-(trimethylsilyl)ethoxy)methyl)-5H-pyrrolo[3,2-d]pyrimidin-2-yl)ethanone as pale yellow solid. $^1$H NMR (400 MHz, CDCl$_3$) δ 9.09 (s, 1H), 7.66 (d, J=3.2 Hz, 1H), 6.89 (d, J=4.8 Hz, 1H), 5.60 (s, 2H), 3.49 (t, J=8.0 Hz, 2H), 2.88 (s, 3H), 0.901 (t, J=8.0 Hz, 2H), −0.053 (s, 9H); MS (ESI) m/z: 291 [M$^+$].

step 2: A microwave vial charged with 1-(5-((2-(trimethylsilyl)ethoxy)methyl)-5H-pyrrolo[3,2-d]pyrimidin-2-yl) ethanone (1.50 g, 5.15 mmol), ethylamine hydrochloride (3.36 g, 41.2 mol), sodium cyanoborohydride (420.5 mg, 6.69 mmol), and anhydrous EtOH (40 mL) was stirred under microwave irradiation (300 Watts) at 130° C. for 2 min. The solid was filtered and rinsed well with EtOH. Volatile solvent from the filtrate was removed under reduced pressure. The resultant crude was redissolved in EtOAc and washed with 10% aqueous NaOH solution (2×), water, and brine. The organic phase was dried (Na$_2$SO$_4$), filtered, and concentrated under reduced pressure. The crude was triturated in DCM, and the insoluble solid was filtered through a pad of Celite®. The filtrate was concentrated under reduced pressure and dried on high-vac to afford N-ethyl-1-(5-((2-(trimethylsilyl)ethoxy)methyl)-5H-pyrrolo[3,2-d]pyrimidin-2-yl)ethanamine as an oil. $^1$H NMR (400 MHz, CDCl$_3$) δ 8.92 (s, 1H), 7.50 (d, J=3.2 Hz, 1H), 6.65 (d, J=3.2 Hz, 1H), 5.50 (s, 2H), 4.09 (q, J=6.7 Hz, 1H), 3.46 (t, J=8.1 Hz, 2H), 2.57 (dd, J=11.2, 7.2 Hz, 1H), 2.46 (dd, J=11.2, 7.0 Hz, 1H), 2.08 (br s, 1H), 1.46 (d, J=6.7 Hz, 3H), 1.08 (t, J=7.1 Hz, 3H), 0.88 (t, J=8.1 Hz, 2H), −0.07 (d, J=0.9 Hz, 9H)); MS (ESI) m/z: 321.4 [M+1]$^+$.

Referential Example 28

(S)-1-(3-chloro-1H-pyrrolo[3,2-b]pyridin-5-yl)ethanamine hydrochloride

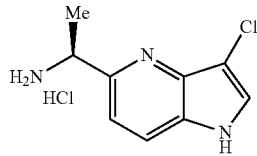 [SMILES: C[C@H](N)c1ccc2[nH]cc(Cl)c2n1 ; Cl]

step 1: To 1-(1H-pyrrolo[3,2-b]pyridin-5-yl)ethanone (2.80 g, 17.48 mmol) in anhydrous DMF (27 mL) at 0° C. was added a solution of N-chlorosuccinimide (2.50 g, 18.36 mmol) dissolved in anhydrous DMF (54 mL). The reaction mixture was stirred at 0° C. for 1 h and then at RT for 18 h. The reaction mixture was diluted with EtOAc, and the organic layer was washed with sat'd. aq. NaHCO$_3$ solution, water and brine, dried (Na$_2$SO$_4$), filtered, and concentrated under reduced pressure. The crude residue was purified by SiO$_2$ chromatography eluting with EtOAc/heptane. Trituration with DCM/heptane afforded 3.35 g (98.59%) of 1-(3-chloro-1H-pyrrolo[3,2-b]pyridin-5-yl)ethanone as a white solid. $^1$H NMR (400 MHz, DMSO) δ 11.96 (br s, 1H), 8.01 (d, J=2.9 Hz, 1H), 7.96 (d, J=8.6 Hz, 1H), 7.88 (d, J=8.6 Hz, 1H), 2.71 (s, 3H); MS (ESI) m/z: 195.2 [M+1]$^+$.

step 2: To a stirred solution of 1-(3-chloro-1H-pyrrolo[3,2-b]pyridin-5-yl)ethanone (2.9 g, 14.90 mmol) and DMAP (184 mg, 1.49 mmol) in anhydrous MeCN (180 mL) at 0° C. was added di-tert-butyl dicarbonate (3.90 g, 17.88 mmol), and the reaction mixture was stirred at RT under N$_2$ for 18 h. Volatile solvent was removed under reduced pressure, and the crude residue was diluted with EtOAc. The EtOAc layer was washed with water and brine, dried (Na$_2$Sa), filtered, and concentrated under reduced pressure. The crude product was purified by SiO$_2$ chromatography eluting with EtOAc/heptane to afford 2.95 g (67.18%) of tert-butyl 5-acetyl-3-chloro-1H-pyrrolo[3,2-b]pyridine-1-carboxylate as a white solid. $^1$H NMR (400 MHz, CDCl$_3$) δ 8.48 (d, J=8.5 Hz, 1H), 8.12 (d, J=8.7 Hz, 1H), 7.91 (s, 1H), 2.84 (s, 3H), 1.68 (d, J=6.5 Hz, 9H); MS (ESI) m/z: 295.1 [M+1]$^+$.

step 3: To tert-butyl 5-acetyl-3-chloro-1H-pyrrolo[3,2-b]pyridine-1-carboxylate (2.90 g, 9.84 mmol) and (R)-2-methylpropane-2-sulfinamide (1.79 g, 14.76 mmol) dissolved in anhydrous THF (96 mL) was added titanium (IV) ethoxide (5.16 mL, 24.60 mmol) at RT under N$_2$. The reaction mixture was then stirred at 75° C. under N$_2$ for 16 h. Volatile solvent was removed under reduced pressure, and the crude residue was diluted with EtOAc (~250 mL). The reaction mixture was vigorously stirred while a saturated solution of brine (~40 mL) was slowly added. The reaction mixture was stirred for 15 min and filtered through a pad of Celite®. The organic layer from the filtrate was washed with water and brine, dried (Na$_2$SO$_4$), filtered, and concentrated under reduced pressure. The crude product was purified by SiO$_2$ chromatography eluting with EtOAc/heptane to afford 1.17 g (29.88%) of (R)-tert-butyl 5-(1-((tert-butylsulfinyl)imino)ethyl)-3-chloro-1H-pyrrolo[3,2-b]pyridine-1-carboxylate and 2.06 g (56.59%) of (R)-ethyl 5-(1-((tert-butylsulfinyl)imino)ethyl)-3-chloro-1H-pyrrolo[3,2-b]pyridine-1-carboxylate.

(R)-tert-butyl 5-(1-((tert-butylsulfinyl)imino)ethyl)-3-chloro-1H-pyrrolo[3,2-b]pyridine-1-carboxylate: $^1$H NMR (400 MHz, CDCl$_3$) δ 8.49-8.38 (m, 1H), 8.22 (d, J=8.8 Hz, 1H), 7.87 (s, 1H), 2.99 (s, 3H), 1.69 (s, 9H), 1.35 (s, 9H); MS (ESI) m/z: 398.2 [M+1]$^+$.

(R)-ethyl 5-(1-((tert-butylsulfinyl)imino)ethyl)-3-chloro-1H-pyrrolo[3,2-b]pyridine-1-carboxylate: $^1$H NMR (400 MHz, CDCl$_3$) δ 8.45 (d, J=8.5 Hz, 1H), 8.24 (d, J=8.8 Hz, 1H), 7.92 (s, 1H), 4.54 (q, J=7.1 Hz, 2H), 2.99 (s, 3H), 1.50 (t, J=7.1 Hz, 3H), 1.35 (s, 9H)); MS (ESI) m/z: 370.2 [M+1]$^+$.

step 4: To (R)-ethyl 5-(1-((tert-butylsulfinyl)imino)ethyl)-3-chloro-1H-pyrrolo[3,2-b]pyridine-1-carboxylate (2.06 g, 5.569 mmol) in anhydrous THF (36.2 mL) at 0° C. was added dropwise L-selectride (1.0 mol/L) in THF (8.4 mL). The resultant orange reaction mixture was then warmed to RT and stirred at this temperature under N$_2$ for 16 h. Volatile solvent was removed under reduced pressure, and the crude residue was diluted with EtOAc. The EtOAc layer was washed with sat'd. aq. NaHCO$_3$, water and brine, dried (Na$_2$SO$_4$), filtered, and concentrated under reduced pressure. The crude product was purified by SiO$_2$ chromatography eluting with MeOH/EtOAc+1% TEA. Trituration with DCM afforded 1.08 g (65.03%) of (R)—N—((S)-1-(3-chloro-1H-pyrrolo[3,2-b]pyridin-5-yl)ethyl)-2-methylpropane-2-sulfinamide as pale yellow solid (100% ee). $^1$H NMR (400 MHz, DMSO) δ 11.52 (s, 1H), 7.80 (d, J=8.5 Hz, 1H), 7.77 (s, 1H), 7.29 (d, J=8.5 Hz, 1H), 5.43 (d, J=5.4 Hz, 1H), 4.62-4.51 (m, 1H), 1.53 (d, J=6.8 Hz, 3H), 1.11 (s, 9H); MS (ESI) m/z: 300.0 [M+1]+.

step 5: To (R)—N—((S)-1-(3-chloro-1H-pyrrolo[3,2-b]pyridin-5-yl)ethyl)-2-methylpropane-2-sulfinamide (1.08 g, 3.23 mmol) in anhydrous MeOH (10 mL) was added HCl (4.0 mol/L) in dioxane (14 mL). The reaction mixture was stirred at 40° C. under N₂ for 16 h. Volatile solvent was removed under reduced pressure. The crude product was triturated with DCM until solid is seen. Light yellow solid was filtered and dried under a high vacuum to afford 868.2 mg (89.3%) of (S)-1-(3-chloro-1H-pyrrolo-[3,2-b]pyridin-5-yl)ethanamine as HCl salt. ¹H NMR (400 MHz, DMSO) δ 11.90 (br s, 1H), 8.47 (br s, 3H), 7.93 (d, J=8.5 Hz, 1H), 7.90 (d, J=2.9 Hz, 1H), 7.37 (d, J=8.5 Hz, 1H), 4.60 (dt, J=12.4, 6.1 Hz, 1H), 1.56 (d, J=6.8 Hz, 3H); MS (ESI) m/z: 196 [M+1]+.

Example 1

$N^2$-((1H-Pyrrolo[2,3-c]pyridin-4-yl)methyl)-$N^4$-(5-cyclopropyl-1H-pyrazol-3-yl)pyrimidine-2,4-diamine (I-1)

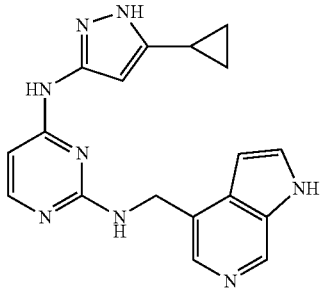 [SMILES: c1cc(Nc2cc(C3CC3)[nH]n2)nc(NCc2cncc3[nH]ccc23)n1]

A mixture of (1H-pyrrolo[2,3-c]pyridin-4-yl)methanamine (236 mg, 1.61 mmol), 2-chloro-N-(5-cyclopropyl-1H-pyrazol-3-yl)pyrimidin-4-amine (344 mg, 1.46 mmol) and DIPEA (565 mg, 4.38 mmol) in IPA (2 mL) was stirred in a sealed tube at 120° C. for 18 h. The reaction mixture was cooled to RT and concentrated in vacuo. The crude residue was purification by preparative HPLC to afford 56 mg (11.1%) of the title compound as white solid: ¹H NMR (500 MHz, CD₃OD) δ 8.64 (s, 1H), 8.06 (s, 1H), 7.85 (s, 1H), 7.59 (d, J=3.0, 1H), 6.72 (d, J=3.0, 1H), 6.17-5.96 (m, 2H), 4.92 (s, 2H), 1.75 (s, 1H), 0.85 (d, J=4.5, 2H), 0.51 (s, 2H); MS (ESI) m/z: 347.2 [M+1]+.

Example 2

$N^2$-((1H-pyrrolo[2,3-b]pyridin-4-yl)methyl)-$N^4$-(5-cyclopropyl-1H-pyrazol-3-yl)pyrimidine-2,4-diamine (I-2)

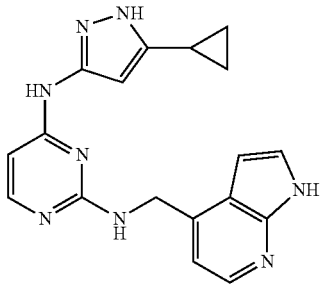 [SMILES: c1cc(Nc2cc(C3CC3)[nH]n2)nc(NCc2ccnc3[nH]ccc23)n1]

The title compound was prepared following the procedure as in Example 1, using (1H-pyrrolo[2,3-b]pyridin-4-yl)methanamine (referential example 9) in place of (1H-pyrrolo[2,3-c]pyridin-4-yl)methanamine (referential example 8) as the starting material: ¹H NMR (500 MHz, CD₃OD) δ 8.13 (d, J=5.0 Hz, 1H), 7.84 (d, J=4.5 Hz, 1H), 7.39 (d, J=4.0 Hz, 1H), 7.08 (d, J=5.0 Hz, 1H), 6.65 (d, J=4.0 Hz, 1H), 6.16-5.81 (m, 2H), 4.94 (s, 2H), 1.69 (brs, 1H), 0.81 (brs, 2H), 0.39 (brs, 2H); MS (ESI) m/z: 347.2 (M+1).

Example 3

$N^2$-((1H-pyrrolo[3,2-c]pyridin-4-yl)methyl)-$N^4$-(5-cyclopropyl-1H-pyrazol-3-yl)pyrimidine-2,4-diamine formic acid salt (I-3)

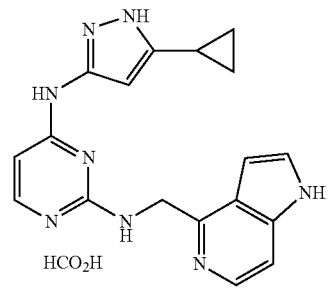 [SMILES: "HCO2H" ; c1cc(Nc2cc(C3CC3)[nH]n2)nc(NCc2nccc3[nH]ccc23)n1]

The title compound was prepared following the procedure as in Example 1, using (1H-Pyrrolo[3,2-c]-pyridin-4-yl)methanamine (referential example 8) in place of (1H-pyrrolo[2,3-c]pyridin-4-yl)methanamine (referential example 10) as the starting material: ¹H NMR (500 MHz, CD₃OD) δ 8.30 (brs, 1H), 8.03 (d, J=6.5 Hz, 1H), 7.73 (d, J=6.0 Hz, 1H), 7.70-7.68 (m, 2H), 7.90 (d, J=3.0 Hz, 1H), 6.11 (brs, 1H), 5.61 (brs, 1H), 5.02 (s, 2H), 1.68 (brs, 1H), 0.85-0.81 (m, 2H), 0.50 (brs, 2H); MS (ESI) m/z: 347.2 (M+1).

Examples 4 and 5

$N^2$-((S)-1-(1H-pyrrolo[3,2-c]pyridin-4-yl)ethyl)-$N^4$-(5-cyclopropyl-1H-pyrazol-3-yl)pyrimidine-2,4-diamine (I-4) and $N^2$-((R)-1-(1H-pyrrolo[3,2-c]pyridin-4-yl)ethyl)-$N^4$-(5-cyclopropyl-1H-pyrazol-3-yl)pyrimidine-2,4-diamine (I-5)

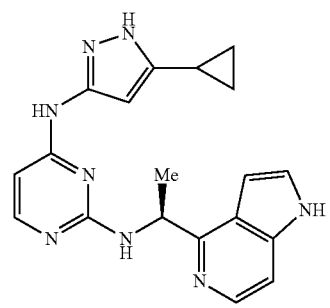

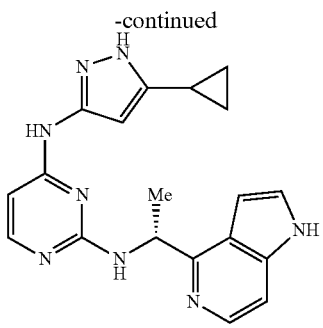

step 1: A mixture of (±)-1-(1-tosyl-1H-pyrrolo[3,2-c]pyridin-4-yl)ethanamine (referential example 11) (800 mg, 2.54 mmol), 2-chloro-N-(5-cyclopropyl-1H-pyrazol-3-yl)-pyrimidin-4-amine (500 mg, 2.12 mmol), and DIPEA (820 mg, 6.36 mmol) in 2,4-dimethylpentan-3-ol (10 mL) in a sealed tube under nitrogen was stirred at 140° C. for 18 h. The crude product was purified by preparative HPLC to afford 563 mg (51.7%) of (±)—N⁴-(5-cyclopropyl-1H-pyrazol-3-yl)-N²-(1-(1-tosyl-1H-pyrrolo[3,2-c]pyridin-4-yl)ethyl)pyrimidine-2,4-diamine as a yellow solid (563 mg, 51.7%): MS (ESI) m/z: 515.2 [M+1]⁺ step 2: A mixture of (±)—N⁴-(5-cyclopropyl-1H-pyrazol-3-yl)-N²-(1-(1-tosyl-1H-pyrrolo[3,2-c]pyridin-4-yl)ethyl) pyrimidine-2,4-diamine (563 mg, 1.10 mmol) and sodium hydroxide (132 mg, 3.29 mmol) in MeOH (20 mL) and water (50 mL) was stirred at 80° C. for 3 h. The reaction mixture was concentrated in vacuo. The crude product was purified by reverse phase preparative HPLC to afford N²-1-(1H-pyrrolo[3,2-c]pyridin-4-yl)ethyl)-N⁴-(5-cyclopropyl-1H-pyrazol-3-yl)pyrimidine-2,4-diamine: MS (ESI) m/z: 361.2 [M+1]⁺.

step 3: Chiral preparative HPLC of racemic N²-1-(1H-pyrrolo[3,2-c]pyridin-4-yl)ethyl)-N⁴-(5-cyclopropyl-1H-pyrazol-3-yl)pyrimidine-2,4-diamine resolved the two enantiomers:

N²-((S)-1-(1H-pyrrolo[3,2-c]pyridin-4-yl)ethyl)-N⁴-(5-cyclopropyl-1H-pyrazol-2,4-diamine (36 mg, 9.1%): ¹H NMR (500 MHz, MeOD-d₄) δ 8.15 (d, J=5.5 Hz, 1H), 7.79 (d, J=6.0 Hz, 1H), 7.35 (d, J=3.5 Hz, 1H), 7.32 (d, J=6.0 Hz, 1H), 6.84 (d, J=2.5 Hz, 1H), 6.10 (brs, 2H), 5.58 (d, J=6.0 Hz, 1H), 1.94-1.89 (m, 1H), 1.66 (d, J=7.0 Hz, 3H), 0.98 (d, J=7.0 Hz, 2H), 0.75 (brs, 2H). MS (ESI) m/z: 361.2 [M+1]⁺.

N²-((R)-1-(1H-pyrrolo[3,2-c]pyridin-4-yl)ethyl)-N⁴-(5-cyclopropyl-1H-pyrazol-3-yl)pyrimidine-2,4-diamine (41 mg, 10.4%): ¹H NMR (500 MHz, MeOD-d₄) δ 8.15 (d, J=5.5 Hz, 1H), 7.79 (d, J=6.0 Hz, 1H), 7.35 (d, J=3.0 Hz, 1H), 7.33 (d, J=6.0 Hz, 1H), 6.84 (d, J=2.0 Hz, 1H), 6.10 (brs, 2H), 5.58 (d, J=6.0 Hz, 1H), 1.94-1.89 (m, 1H), 1.66 (d, J=6.5 Hz, 3H), 0.98 (d, J=6.0 Hz, 2H), 0.75 (s, 2H). MS (ESI) m/z: 361.2 [M+1]⁺.

Example 6

N²-((1H-Pyrrolo[2,3-b]pyridin-5-yl)methyl)-N⁴-(5-cyclopropyl-1H-pyrazol-3-yl)pyrimidine-2,4-diamine (I-6)

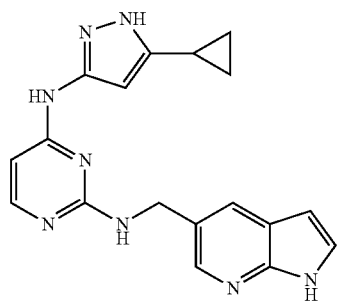 [SMILES: c1cc(Nc2cc(C3CC3)[nH]n2)nc(NCc2cnc3[nH]ccc3c2)n1]

The title compound was prepared following the procedures according to steps 1 and 2 of Example 4, using (1-tosyl-1H-pyrrolo[2,3-b]pyridin-5-yl)methanamine (referential example 12) in place of (±)-1-(1-tosyl-1H-pyrrolo[3,2-c]pyridin-4-yl)ethanamine (referential example 12) as the starting material: ¹H NMR (500 MHz, DMSO-d₆) δ 11.91 (s, 1H), 11.54 (s, 1H), 9.29 (s, 1H), 8.21 (s, 1H), 7.87-7.80 (m, 2H), 7.41-7.17 (m, 2H), 6.79-6.74 (m, 1H), 6.38-6.12 (m, 2H), 4.56 (d, 2H), 2.50-2.45 (m, 1H), 0.85-0.53 (m, 4H); MS (ESI) m/z: 347.2 [M+1]⁺.

Examples 7 and 8

(S)—N²-(1-(1H-pyrrolo[2,3-c]pyridin-5-yl)ethyl)-N⁴-(5-cyclopropyl-1H-pyrazol-3-yl)pyrimidine-2,4-diamine (I-7) and (R)—N²-(1-(1H-pyrrolo[2,3-c]pyridin-5-yl)ethyl)-N⁴-(5-cyclopropyl-1H-pyrazol-3-yl)pyrimidine-2,4-diamine (I-8)

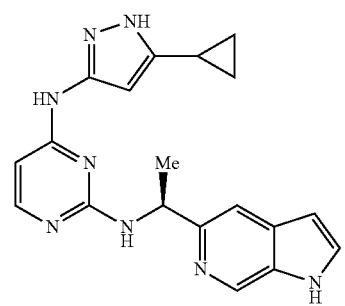

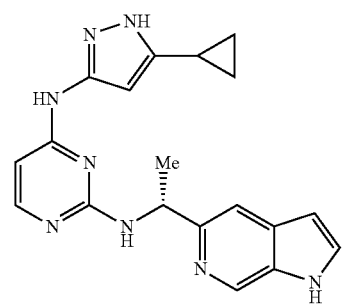

step 1: A sealed-cap vial was charged with 2-chloro-N-(5-cyclopropyl-1H-pyrazol-3-yl)-pyrimidin-4-amine (60 mg, 0.25 mmol), tert-butyl 5-(1-aminoethyl)-1H-pyrrolo[2,3-c]pyridine-1-carboxylate (93 mg, 0.36 mmol), DIPEA (0.16 mL) and n-BuOH (0.8 mL). The mixture was heated at 115° C. for 72 h. The reaction mixture was concentrated under reduced pressure. The crude mixture was purified by preparative HPLC to afford N²-(1-(1H-pyrrolo[2,3-c]pyridin-5-yl)ethyl)-N⁴-(5-cyclopropyl-1H-pyrazol-3-yl)pyrimidine-2,4-diamine: MS (ESI) m/z: 361.2 [M+1]⁺.

step 2: Chiral SFC chromatography of racemic N²-(1-(1H-pyrrolo[2,3-c]pyridin-5-yl) ethyl)-N⁴-(5-cyclopropyl-1H-pyrazol-3-yl)pyrimidine-2,4-diamine afforded the corresponding two enantiomers:

(S)—N²-(1-(1H-pyrrolo[2,3-c]pyridin-5-yl)ethyl)-N⁴-(5-cyclopropyl-1H-pyrazol-3-yl)pyrimidine-2,4-diamine (17.5 mg, 19%): ¹H NMR (400 MHz, DMSO-d⁶) δ 11.44 (s, 1H), 9.36 (br s, 1H), 8.69 (s, 1H), 8.16 (s, 1H), 7.77 (d, J=5.7 Hz, 1H), 7.54 (s, 1H), 7.50 (s, 1H), 7.16-6.84 (m, 1H), 6.42 (d, J=2.6 Hz, 1H), 6.15-5.85 (m, 2H), 5.26-5.08 (m, 1H), 1.89-1.76 (m, 1H), 1.48 (d, J=6.9 Hz, 3H), 0.97-0.81 (m, 2H), 0.81-0.57 (m, 2H). MS (ESI) m/z: 361.2 [M+1]⁺.

(R)—N²-(1-(1H-pyrrolo[2,3-c]pyridin-5-yl)ethyl)-N⁴-(5-cyclopropyl-1H-pyrazol-3-yl)pyrimidine-2,4-diamine (15.6 mg, 17%): ¹H NMR (400 MHz, DMSO-d⁶) δ 11.44 (s, 1H), 9.36 (br s, 1H), 8.69 (s, 1H), 8.16 (s, 1H), 7.77 (d, J=5.7 Hz, 1H), 7.54 (s, 1H), 7.50 (s, 1H), 7.16-6.84 (m, 1H), 6.42 (d, J=2.6 Hz, 1H), 6.15-5.85 (m, 2H), 5.26-5.08 (m, 1H), 1.89-1.76 (m, 1H), 1.48 (d, J=6.9 Hz, 3H), 0.97-0.81 (m, 2H), 0.81-0.57 (m, 2H). MS (ESI) m/z: 361.2 [M+1]⁺.

Example 9

N²-((1H-pyrrolo[3,2-b]pyridin-5-yl)methyl)-N⁴-(5-cyclopropyl-1H-pyrazol-3-yl)pyrimidine-2,4-diamine (I-9)

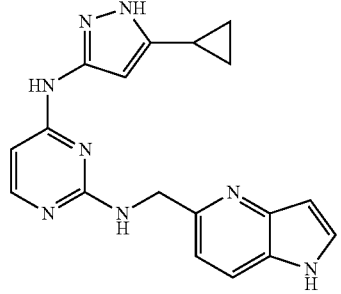

The title compound was prepared following the procedure described in step 1 of Example 7, using (1H-pyrrolo[3,2-b]pyridin-5-yl)methanamine (CASRN 267876-26-6) in place of tert-butyl 5-(1-aminoethyl)-1H-pyrrolo[2,3-c]-pyridine-1-carboxylate (referential example 17) as the starting material and heating the reaction mixture at 140° C. for 18 h: NMR (400 MHz, DMSO-d⁶) δ 12.63-11.70 (m, 1H), 11.17 (s, 1H), 9.99-9.06 (m, 1H), 7.90-7.63 (m, 2H), 7.57 (s, 1H), 7.22-6.96 (m, 2H), 6.50 (s, 1H), 6.35-5.81 (m, 2H), 4.63 (d, J=5.4 Hz, 2H), 1.87-1.70 (m, 1H), 0.93-0.52 (m, 4H); MS (ESI) m/z: 347 [M+1]⁺.

Example 10

N²-((1H-pyrrolo[3,2-b]pyridin-5-yl)methyl)-N⁴-(5-cyclopropyl-1H-pyrazol-3-yl)-N²-methylpyrimidine-2,4-diamine (I-10)

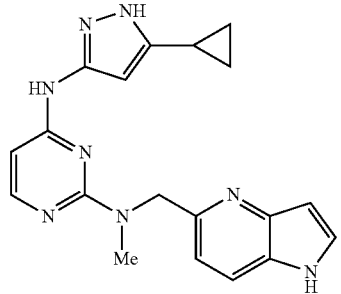 [SMILES: CN(Cc1ccc2[nH]ccc2n1)c1nccc(Nc2cc(C3CC3)[nH]n2)n1]

The title compound was prepared following the procedure according to Example 9, using N-methyl-1-(1H-pyrrolo[3,2-b]pyridin-5-yl)methanamine hydrochloride (referential example 16) in place of (1H-pyrrolo[3,2-b]pyridin-5-yl)methanamine as the starting material: ¹H NMR (400 MHz, DMSO-d⁶) cS 11.85 (s, 1H), 11.18 (s, 1H), 9.32 (s, 1H), 7.88 (d, J=5.6 Hz, 1H), 7.68 (d, J=8.3 Hz, 1H), 7.58 (t, J=3 Hz, 1H), 6.91 (d, J=8.5 Hz, 1H), 6.50 (s, 1H), 6.23 (br s, 1H), 6.06 (br s, 1H), 4.95 (s, 2H), 3.12 (s, 3H), 1.75 (s, 1H), 0.82 (s, 2H), 0.52 (s, 2H); MS (ESI) m/z: 361.3 [M+1]⁺.

Example 11

(S)—N²-(1-(3-chloro-1H-pyrrolo[3,2-b]pyridin-5-yl)ethyl)-N⁴-(5-cyclopropyl-1H-pyrazol-3-yl)pyrimidine-2,4-diamine (I-11)

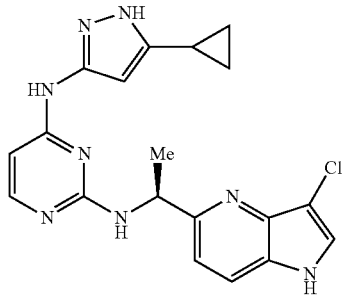 [SMILES: C[C@H](Nc1nccc(Nc2cc(C3CC3)[nH]n2)n1)c1ccc2[nH]cc(Cl)c2n1]

The title compound was prepared following the procedure according to Example 9, using (S)-1-(3-chloro-1H-pyrrolo[3,2-b]pyridin-5-yl)ethanamine hydrochloride (referential example 18) in place of (1H-pyrrolo[3,2-b]pyridin-5-yl)methanamine as the starting material: ¹H NMR (400 MHz, DMSO-d⁶) δ 11.81 (br s, 1H), 11.48 (s, 1H), 9.27 (br s, 1H), 7.82-7.72 (m, 3H), 7.26 (d, J=8.5 Hz, 1H), 7.02 (br s, 1H), 6.15 (br s, 2H), 5.27-5.17 (m, 1H), 1.86-1.75 (m, 1H), 1.51 (d, J=6.9 Hz, 3H), 0.87 (s, 2H), 0.65 (s, 2H); MS (ESI) m/z: 395.1 [M+1]⁺.

Examples 12 and 13

(S)—N²-(1-(1H-pyrrolo[3,2-b]pyridin-5-yl)ethyl)-N⁴-(5-cyclopropyl-1H-pyrazol-3-yl)pyrimidine-2,4-diamine (I-12) and (R)—N²-(1-(1H-pyrrolo[3,2-b]pyridin-5-yl)ethyl)-N⁴-(5-cyclopropyl-1,1-pyrazol-3-yl)pyrimidine-2,4-diamine (I-13)

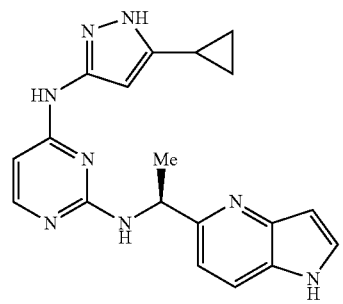

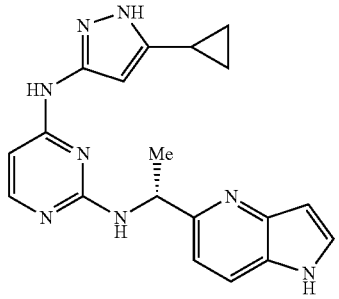

The title compounds were prepared following the procedures according to Examples 7 and 8, using 1-(1H-pyrrolo[3,2-b]pyridin-5-yl)ethanamine (referential example 13) in place of tert-butyl 5-(1-aminoethyl)-1H-pyrrolo[2,3-c]-pyridine-1-carboxylate (referential example 17) as the starting material. Chiral SFC separation afforded the following two enantiomers:

(S)—$N^2$-(1-(1H-pyrrolo[3,2-b]pyridin-5-yl)ethyl)-$N^4$-(5-cyclopropyl-1H-pyrazol-3-yl)pyrimidine-2,4-diamine: $^1$H NMR (400 MHz, DMSO-$d^6$) δ 11.90 (br s, 1H), 11.17 (s, 1H), 9.34 (br s, 1H), 7.77 (d, J=5.7 Hz, 1H), 7.70 (d, J=8.4 Hz, 1H), 7.57 (t, J=2.8 Hz, 1H), 7.16 (d, J=8.4 Hz, 1H), 7.10 (br s, 1H), 6.53 (s, 1H), 6.07 (br s, 2H), 5.26-514 (m, 1H), 1.88-1.79 (m, 1H), 1.49 (d, J=6.9 Hz, 3H), 0.89 (d, J=6.4 Hz, 2H), 0.71 (s, 2H); MS (ESI) m/z: 361.3 [M+1]$^+$; SFC RT=0.84 min.

(R)—$N^2$-(1-(1H-pyrrolo[3,2-b]pyridin-5-yl)ethyl)-$N^4$-(5-cyclopropyl-1H-pyrazol-3-yl)pyrimidine-2,4-diamine: $^1$H NMR (400 MHz, DMSO-$d^6$) δ 11.90 (br s, 1H), 11.17 (s, 1H), 9.34 (br s, 1H), 7.77 (d, J=5.7 Hz, 1H), 7.70 (d, J=8.4 Hz, 1H), 7.57 (t, J=2.8 Hz, 1H), 7.16 (d, J=8.4 Hz, 1H), 7.10 (br s, 1H), 6.53 (s, 1H), 6.07 (br s, 2H), 5.26-514 (m, 1H), 1.88-1.79 (m, 1H), 1.49 (d, J=6.9 Hz, 3H), 0.89 (d, J=6.4 Hz, 2H), 0.71 (s, 2H); MS (ESI) m/z: 361.3 [M+1]$^+$; SFC RT=0.98 min.

Examples 14 and 15

(S)—$N^2$-(1-(1H-pyrrolo[3,2-b]pyridin-5-yl)ethyl)-$N^4$-(5-cyclopropyl-1H-pyrazol-3-yl)-5-fluoropyrimidine-2,4-diamine (I-14) and (R)—$N^2$-(1-(1H-pyrrolo[3,2-b]pyridin-5-yl)ethyl)-$N^4$-(5-cyclopropyl-1H-pyrazol-3-yl)-5-fluoropyrimidine-2,4-diamine (I-15)

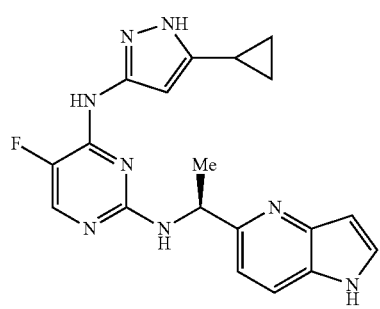

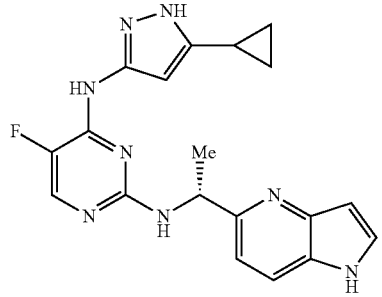

The title compounds were prepared following the procedures according to Examples 12 and 13, using 2-chloro-N-(5-cyclopropyl-1H-pyrazol-3-yl)-5-fluoropyrimidin-4-amine (referential example 2) in place of 2-chloro-N-(5-cyclopropyl-1H-pyrazol-3-yl)pyrimidin-4-amine (referential example 1) as the starting material. Chiral SFC separation afforded the following two enantiomers:

(S)—$N^2$-(1-(1H-pyrrolo[3,2-b]pyridin-5-yl)ethyl)-$N^4$-(5-cyclopropyl-1H-pyrazol-3-yl)-5-fluoropyrimidine-2,4-diamine: $^1$H NMR (400 MHz, DMSO-$d^6$) δ 11.17 (s, 1H), 9.68-9.36 (br s, 1H), 7.83 (d, J=3.7 Hz, 1H), 7.70 (d, J=8.4 Hz, 1H), 7.57 (t, J=2.9 Hz, 1H), 7.29 (br s, 1H), 7.14 (d, J=8.4 Hz, 1H), 6.52 (s, 1H), 6.09 (bt s, 1H), 5.10 (t, J=7.1 Hz, 1H), 1.89-1.60 (m, 1H), 1.48 (d, J=7.0 Hz, 3H), 0.89 (d, J=8.2 Hz, 2H), 0.72 (s, 2H); 1H hidden under water peak. MS (ESI) m/z: 361.3 [M+1]$^+$; SFC RT=0.32 min.

(R)—$N^2$-(1-(1H-pyrrolo[3,2-b]pyridin-5-yl)ethyl)-$N^4$-(5-cyclopropyl-1H-pyrazol-3-yl)-5-fluoropyrimidine-2,4-diamine: $^1$H NMR (400 MHz, DMSO-$d^6$) δ 11.17 (s, 1H), 9.68-9.36 (br s, 1H), 7.83 (d, J=3.7 Hz, 1H), 7.70 (d, J=8.4 Hz, 1H), 7.57 (t, J=2.9 Hz, 1H), 7.29 (br s, 1H), 7.14 (d, J=8.4 Hz, 1H), 6.52 (s, 1H), 6.09 (br s, 1H), 5.10 (t, J=7.1 Hz, 1H), 1.89-1.60 (m, 1H), 1.48 (d, J=7.0 Hz, 3H), 0.89 (d, J=8.2 Hz, 2H), 0.72 (s, 2H); 1H hidden under water peak. MS (ESI) m/z: 361.3 [M+1]$^+$; SFC RT=0.58 min.

Examples 16 and 17

(S)—$N^2$-(1-(1H-pyrrolo[3,2-b]pyridin-5-yl)ethyl)-$N^4$-(5-(3,3-difluorocyclobutyl)-1H-pyrazol-3-yl)pyrimidine-2,4-diamine (I-16) and (R)—$N^2$-(1-(1H-pyrrolo[3,2-b]pyridin-5-yl)ethyl)-$N^4$-(5-(3,3-difluorocyclobutyl)-1H-pyrazol-3-yl)pyrimidine-2,4-diamine (I-17)

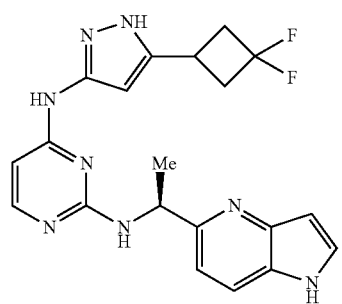

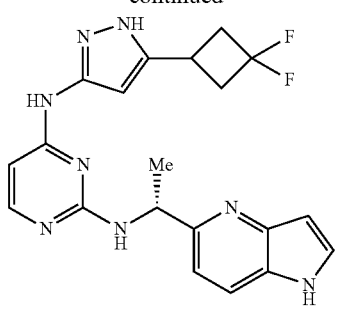

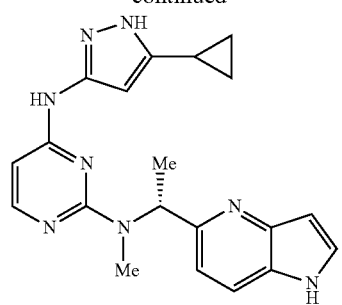

The title compounds were prepared following the procedures according to Examples 12 and 13, using 2-chloro-N-(5-(3,3-difluorocyclobutyl)-1H-pyrazol-3-yl)pyrimidin-4-amine (referential example 3) in place of 2-chloro-N-(5-cyclopropyl-1H-pyrazol-3-yl)pyrimidin-4-amine (referential example 1) as the starting material. Chiral SFC separation afforded the following two enantiomers:

(S)—$N^2$-(1-(1H-pyrrolo[3,2-b]pyridin-5-yl)ethyl)-$N^4$-(5-(3,3-difluorocyclobutyl)-1H-pyrazol-3-yl)pyrimidine-2,4-diamine: $^1$H NMR (400 MHz, DMSO-$d^6$) δ 13.51-11.77 (br m, 1H), 11.18 (s, 1H), 9.54 (br s, 1H), 7.80 (d, J=5.6 Hz, 1H), 7.71 (d, J=8.4 Hz, 1H), 7.57 (s, 1H), 7.45-6.90 (br s, 1H), 7.17 (d, J=8.0 Hz, 1H), 6.53 (s, 1H), 6.02 (s, 2H), 5.20 (s, 1H), 3.04-2.89 (m, 2H), 2.87-2.69 (m, 2H), 1.50 (d, J=6.9 Hz, 3H); 1H hidden under water peak. MS (ESI) m/z: 411.1 [M+1]$^+$; SFC RT=0.43 min.

(R)—$N^2$-(1-(1H-pyrrolo[3,2-b]pyridin-5-yl)ethyl)-$N^4$-(5-(3,3-difluorocyclobutyl)-1H-pyrazol-3-yl)pyrimidine-2,4-diamine: $^1$H NMR (400 MHz, DMSO-$d^6$) δ 13.51-11.77 (br m, 1H), 11.18 (s, 1H), 9.54 (br s, 1H), 7.80 (d, J=5.6 Hz, 1H), 7.71 (d, J=8.4 Hz, 1H), 7.57 (s, 1H), 7.45-6.90 (br s, 1H), 7.17 (d, J=8.0 Hz, 1H), 6.53 (s, 1H), 6.02 (s, 2H), 5.20 (s, 1H), 3.04-2.89 (m, 2H), 2.87-2.69 (m, 2H), 1.50 (d, J=6.9 Hz, 3H); 1H hidden under water peak. MS (ESI) m/z: 411.1 [M+1]$^+$; SFC RT=0.57 min.

Examples 18 and 19

(S)—$N^2$-(1-(1H-pyrrolo[3,2-b]pyridin-5-yl)ethyl)-$N^4$-(5-cyclopropyl-1H-pyrazol-3-yl)-$N^2$-methylpyrimidine-2,4-diamine (I-18) and (R)—$N^2$-(1-(1H-pyrrolo[3,2-b]pyridin-5-yl)ethyl)-$N^4$-(5-cyclopropyl-1H-pyrazol-3-yl)-$N^2$-methylpyrimidine-2,4-diamine (I-19)

The title compounds were prepared following the procedures according to Examples 12 and 13, using N-methyl-1-(1H-pyrrolo[3,2-b]pyridin-5-yl)ethanamine (referential example 15) in place of 1-(1H-pyrrolo[3,2-b]pyridin-5-yl)ethanamine (referential example 13) as the starting material. Chiral SFC separation afforded the following two enantiomers:

(S)—$N^2$-(1-(1H-pyrrolo[3,2-b]pyridin-5-yl)ethyl)-$N^4$-(5-cyclopropyl-1H-pyrazol-3-yl)-$N^2$-methylpyrimidine-2,4-diamine: $^1$H NMR (400 MHz, DMSO-$d^6$) δ 11.92 (s, 1H), 11.21 (s, 1H), 9.35 (s, 1H), 7.90 (d, J=5.7 Hz, 1H), 7.69 (d, J=8.4 Hz, 1H), 7.59 (s, 1H), 6.99 (d, J=8.4 Hz, 1H), 6.55 (s, 1H), 6.27 (s, 2H), 6.10 (s, 1H), 2.82 (s, 3H), 1.85-1.76 (m, 1H), 1.59 (d, J=7.0 Hz, 3H), 0.85 (d, J=8.2 Hz, 2H), 0.57 (s, 2H); MS (ESI) m/z: 375.2 [M+1]$^+$; SFC RT=0.35 min.

(R)—$N^2$-(1-(1H-pyrrolo[3,2-b]pyridin-5-yl)ethyl)-$N^4$-(5-cyclopropyl-1H-pyrazol-3-yl)-$N^2$-methylpyrimidine-2,4-diamine: $^1$H NMR (400 MHz, DMSO-$d^6$) δ 11.92 (s, 1H), 11.21 (s, 1H), 9.35 (s, 1H), 7.90 (d, J=5.7 Hz, 1H), 7.69 (d, J=8.4 Hz, 1H), 7.59 (s, 1H), 6.99 (d, J=8.4 Hz, 1H), 6.55 (s, 1H), 6.27 (s, 2H), 6.10 (s, 1H), 2.82 (s, 3H), 1.85-1.76 (m, 1H), 1.59 (d, J=7.0 Hz, 3H), 0.85 (d, J=8.2 Hz, 2H), 0.57 (s, 2H); MS (ESI) m/z: 375.2 [M+1]$^+$; SFC RT=0.34 min.

Examples 20 and 21

(S)—$N^2$-(1-(1H-pyrrolo[3,2-b]pyridin-5-yl)ethyl)-$N^4$-(5-cyclopropyl-1H-pyrazol-3-yl)-5-fluoro-$N^2$-methylpyrimidine-2,4-diamine (I-20) and (R)—$N^2$-(1-(1H-pyrrolo[3,2-b]pyridin-5-yl)ethyl)-$N^4$-(5-cyclopropyl-1H-pyrazol-3-yl)-5-fluoro-$N^2$-methylpyrimidine-2,4-diamine (I-21)

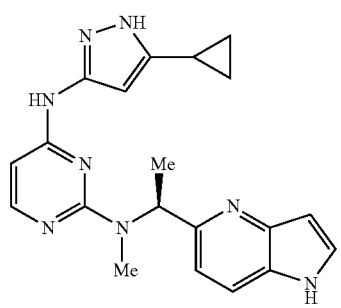

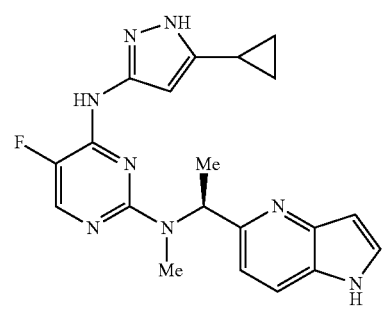

-continued

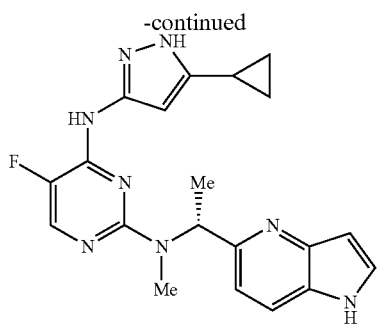

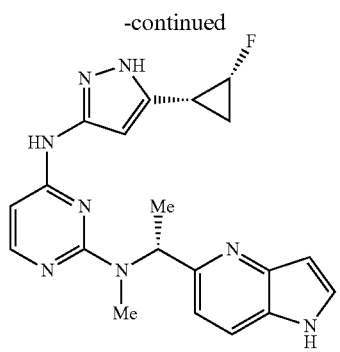

The title compounds were prepared following the procedures according to Examples 18 and 19, using 2-chloro-N-(5-cyclopropyl-1H-pyrazol-3-yl)-5-fluoropyrimidin-4-amine (referential example 2) in place of 2-chloro-N-(5-cyclopropyl-1H-pyrazol-3-yl)pyrimidin-4-amine (referential example 1) as the starting material. Chiral SFC separation afforded the following two enantiomers:

(S)—$N^2$-(1-(1H-pyrrolo[3,2-b]pyridin-5-yl)ethyl)-$N^4$-(5-cyclopropyl-1H-pyrazol-3-yl)-5-fluoro-$N^2$-methylpyrimidine-2,4-diamine: $^1$H NMR (400 MHz, DMSO-d$^6$) δ 12.05 (br s, 1H), 11.19 (s, 1H), 9.40 (br s, 1H), 7.95 (d, J=3.7 Hz, 1H), 7.69 (d, J=8.4 Hz, 1H), 7.58 (t, J=2.9 Hz, 1H), 6.98 (d, J=8.5 Hz, 1H), 6.55 (s, 1H), 6.21 (br s, 1H), 6.12 (d, J=6.5 Hz, 1H), 2.83 (s, 3H), 1.80 (ddd, J=13.5, 8.4, 5.0 Hz, 1H), 1.59 (d, J=7.0 Hz, 3H), 0.89-0.79 (m, 2H), 0.55 (s, 2H); MS (ESI) m/z: 393.1 [M+1]$^+$; SFC RT=0.93 min.

(R)—$N^2$-(1-(1H-pyrrolo[3,2-b]pyridin-5-yl)ethyl)-$N^4$-(5-cyclopropyl-1H-pyrazol-3-yl)-5-fluoro-$N^2$-methylpyrimidine-2,4-diamine: $^1$H NMR (400 MHz, DMSO-d$^6$) δ 12.05 (br s, 1H), 11.19 (s, 1H), 9.40 (br s, 1H), 7.95 (d, J=33 Hz, 1H), 7.69 (d, J=8.4 Hz, 1H), 7.58 (t, J=2.9 Hz, 1H), 6.98 (d, J=8.5 Hz, 1H), 6.55 (s, 1H), 6.21 (br s, 1H), 6.12 (d, J=6.5 Hz, 1H), 2.83 (s, 3H), 1.80 (ddd, J=13.5, 8.4, 5.0 Hz, 1H), 1.59 (d, J=7.0 Hz, 3H), 0.89-0.79 (m, 2H), 0.55 (s, 2H); MS (ESI) m/z: 393.1 [M+1]$^+$; SFC RT=0.45 min.

Examples 22 and 23

$N^2$-((S)-1-(1H-pyrrolo[3,2-b]pyridin-5-yl)ethyl)-$N^4$-(5-((1R,2R)-2-fluorocyclopropyl)-1H-pyrazol-3-yl)-$N^2$-methylpyrimidine-2,4-diamine (I-22) and $N^2$-((R)-1-(1H-pyrrolo[3,2-b]pyridin-5-yl)ethyl)-$N^4$-(5-((1R,2R)-2-fluorocyclopropyl)-1H-pyrazol-3-yl)-$N^2$-methylpyrimidine-2,4-diamine (I-23)

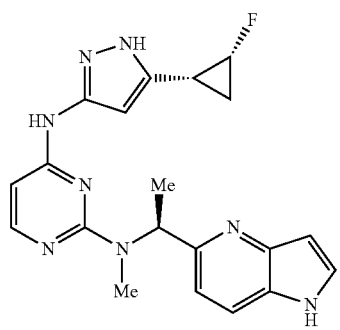

The title compounds were prepared following the procedures according to Examples 18 and 19, using 2-chloro-N-(5-((1R,2R)-2-fluorocyclopropyl)-1H-pyrazol-3-yl)pyrimidin-4-amine (referential example 4) in place of 2-chloro-N-(5-cyclopropyl-1H-pyrazol-3-yl)pyrimidin-4-amine (referential example 1) as the starting material. Chiral SFC separation afforded the following two enantiomers:

$N^2$-((S)-1-(1H-pyrrolo[3,2-b]pyridin-5-yl)ethyl)-$N^4$-(5-((1R,2R)-2-fluorocyclopropyl)-1H-pyrazol-3-yl)-$N^2$-methylpyrimidine-2,4-diamine: $^1$H NMR (400 MHz, DMSO-d$^6$) δ 12.63-11.82 (br s, 1H), 11.20 (s, 1H), 9.41 (s, 1H), 7.91 (d, J=5.7 Hz, 1H), 7.68 (d, J=8.4 Hz, 1H), 7.58 (t, J=2.9 Hz, 1H), 6.99 (d, J=8.4 Hz, 1H), 6.55 (s, 1H), 6.35-6.15 (m, 3H), 4.97-4.75 (m, 1H), 2.81 (s, 3H), 2.06-1.97 (m, 1H), 1.59 (d, J=7.0 Hz, 3H), 1.26-1.08 (m, 21-1); MS (ESI) m/z: 393.1 [M+1]$^+$; SFC RT=0.98 min.

$N^2$-((R)-1-(1H-pyrrolo[3,2-b]pyridin-5-yl)ethyl)-$N^4$-(5-((1R,2R)-2-fluorocyclopropyl)-1H-pyrazol-3-yl)-$N^2$-methylpyrimidine-2,4-diamine: $^1$H NMR (400 MHz, DMSO-d$^6$) δ 12.63-11.82 (br s, 1H), 11.20 (s, 1H), 9.41 (s, 1H), 7.91 (d, J=5.7 Hz, 1H), 7.68 (d, J=8.4 Hz, 1H), 7.58 (t, J=2.9 Hz, 1H), 6.99 (d, J=8.4 Hz, 1H), 6.55 (s, 1H), 6.35-6.15 (m, 3H), 4.97-4.75 (m, 1H), 2.81 (s, 3H), 2.06-1.97 (m, 1H), 1.59 (d, J=7.0 Hz, 3H), 1.26-1.08 (m, 2H); MS (ESI) m/z: 393.1 [M+1]$^+$; SFC RT=0.83 min.

Examples 24 and 25

$N^2$-((S)-1-(1H-pyrrolo[3,2-b]pyridin-5-yl)ethyl)-$N^4$-(5-((1S,2S)-2-fluorocyclopropyl)-1H-pyrazol-3-yl)-$N^2$-methylpyrimidine-2,4-diamine formic acid salt (I-24) and $N^2$-((R)-1-(1H-pyrrolo[3,2-b]pyridin-5-yl)ethyl)-$N^4$-(5-((1S,2S)-2-fluorocyclopropyl)-1H-pyrazol-3-yl)-$N^2$-methylpyrimidine-2,4-diamine (I-25)

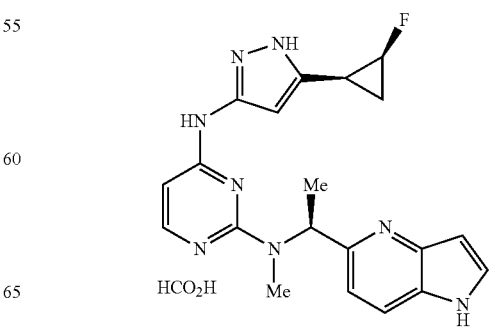

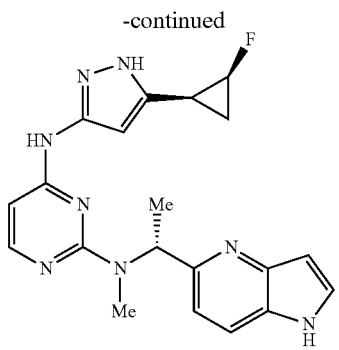

The title compounds were prepared following the procedures according to Examples 18 and 19, using 2-chloro-N-(5-((1S,2S)-2-fluorocyclopropyl)-1H-pyrazol-3-yl)pyrimidin-4-amine (referential example 5) in place of 2-chloro-N-(5-cyclopropyl-1H-pyrazol-3-yl)pyrimidin-4-amine (referential example 1) as the starting material. Chiral SFC separation afforded the following two enantiomers:

$N^2$-((S)-1-(1H-pyrrolo[3,2-b]pyridin-5-yl)ethyl)-$N^4$-(5-((1S,2S)-2-fluorocyclopropyl)-1H-pyrazol-3-yl)-$N^2$-methylpyrimidine-2,4-diamine formic acid salt: $^1$H NMR (400 MHz, DMSO-d$^6$) δ 11.21 (s, 1H), 9.42 (s, 1H), 8.20 (s, 1H), 7.91 (d, J=5.7 Hz, 1H), 7.69 (d, J=8.4 Hz, 1H), 7.58 (t, J=2.9 Hz, 1H), 6.99 (d, J=8.4 Hz, 1H), 6.55 (s, 1H), 6.37-6.14 (m, 3H), 4.86 (dd, J=66.1, 3.0 Hz, 2H), 182 (s, 3H), 2.06-1.97 (m, 1H), 1.58 (d, J=7.0 Hz, 3H), 1.29-1.06 (m, 2H); MS (ESI) m/z: 393.2 [M+1]$^+$; SFC RT=0.47 min.

$N^2$—((R)-1-(1H-pyrrolo[3,2-b]pyridin-5-yl)ethyl)-$N^4$-(5-((1S,2S)-2-fluorocyclopropyl)-1H-pyrazol-3-yl)-$N^2$-methylpyrimidine-2,4-diamine: $^1$H NMR (400 MHz, DMSO-d$^6$) δ 12.06 (br s, 1H), 11.20 (s, 1H), 9.39 (br s, 1H), 7.91 (d, J=5.7 Hz, 1H), 7.68 (d, J=8.4 Hz, 1H), 7.58 (s, 1H), 6.99 (d, J=8.2 Hz, 1H), 6.55 (s, 1H), 6.28 (br s, 3H), 4.86 (dd, J=66.1, 3.0 Hz, 1H), 2.81 (s, 3H), 2.09-1.93 (m, 1H), 1.59 (d, J=7.0 Hz, 3H), 1.28-1.06 (m, 2H); MS (ESI) m/z: 393.2 [M+1]$^+$; SFC RT=0.38 min.

Examples 26 and 27

$N^2$—((S)-1-(1H-pyrrolo[3,2-b]pyridin-5-yl)ethyl)-$N^4$-(5-((1S,2R)-2-fluorocyclopropyl)-1H-pyrazol-3-yl)-$N^2$-methylpyrimidine-2,4-diamine formic acid salt (I-26) and $N^2$-((R)-1-(1H-pyrrolo[3,2-b]pyridin-5-yl)ethyl)-$N^4$-(5-((1S,2R)-2-fluorocyclopropyl)-1H-pyrazol-3-yl)-$N^2$-methylpyrimidine-2,4-diamine (I-27)

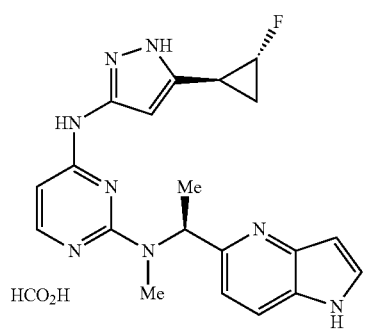

The title compounds were prepared following the procedures according to Examples 18 and 19, using 2-chloro-N-(5-((1S,2R)-2-fluorocyclopropyl)-1H-pyrazol-3-yl)pyrimidin-4-amine (referential example 7) in place of 2-chloro-N-(5-cyclopropyl-1H-pyrazol-3-yl)pyrimidin-4-amine (referential example 1) as the starting material. Chiral SFC separation afforded the following two enantiomers:

$N^2$—((S)-1-(1H-pyrrolo[3,2-b]pyridin-5-yl)ethyl)-$N^4$-(5-((1S,2R)-2-fluorocyclopropyl)-1H-pyrazol-3-yl)-$N^2$-methylpyrimidine-2,4-diamine formic acid salt: $^1$H NMR (400 MHz, DMSO-d$^6$) δ 11.22 (s, 1H), 9.45 (s, 1H), 8.19 (s, 1H), 7.92 (d, J=5.7 Hz, 1H), 7.70 (d, J=8.4 Hz, 1H), 7.59 (t, J=2.9 Hz, 1H), 7.00 (d, J=8.4 Hz, 1H), 6.55 (s, 1H), 6.22 (br s, 2H), 6.11 (br s, 1H), 4.76 (d, J=64.2 Hz, 1H), 2.86 (s, 3H), 2.42-2.28 (m, 1H), 1.60 (d, J=7.0 Hz, 3H), 1.54-1.39 (m, 1H), 1.09-0.96 (m, 1H); MS (ESI) m/z: 393.1 [M+1]$^+$; SFC RT=0.46 min.

$N^2$— ((R)-1-(1H-pyrrolo[3,2-b]pyridin-5-yl)ethyl)-$N^4$-(5-((1S,2R)-2-fluorocyclopropyl)-1H-pyrazol-3-yl)-$N^2$-methylpyrimidine-2,4-diamine; NMR (400 MHz, DMSO-d$^6$) δ 12.03 (br s, 1H), 1121 (s, 1H), 9.41 (br s, 1H), 7.92 (d, J=5.6 Hz, 1H), 7.69 (d, J=8.4 Hz, 1H), 7.59 (t, J=2.9 Hz, 1H), 6.99 (d, J=7.5 Hz, 1H), 6.55 (s, 1H), 6.25 (br s, 3H), 4.79 (d, J=69.7 Hz, 1H), 2.85 (s, 3H), 2.44-2.25 (m, 1H), 1.60 (d, J=7.0 Hz, 3H), 1.54-1.37 (m, 1H), 1.07-0.94 (m, 1H); MS (ESI) m/z: 393.1 [M+1]$^+$; SFC RT=0.42 min.

Examples 28 and 29

$N^2$—((S)-1-(1H-pyrrolo[3,2-b]pyridin-5-yl)ethyl)-$N^4$-(5-((1R,2S)-2-fluorocyclopropyl)-1H-pyrazol-3-yl)-$N^2$-methylpyrimidine-2,4-diamine (I-28) and $N^2$—((R)-1-(1H-pyrrolo[3,2-b]pyridin-5-yl)ethyl)-$N^4$-(5-((1R,2S)-2-fluorocyclopropyl)-1H-pyrazol-3-yl)-$N^2$-methylpyrimidine-2,4-diamine (I-29)

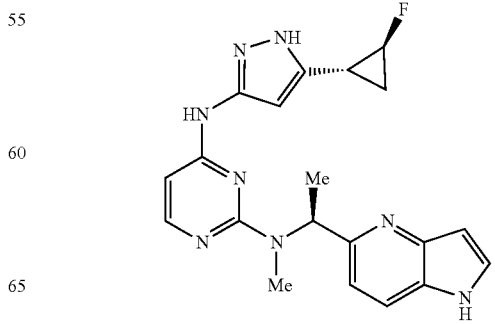

-continued

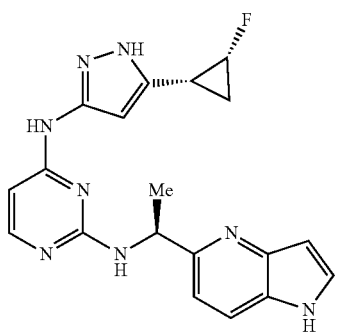 [SMILES: C[C@H](Nc1nccc(Nc2cc([C@H]3C[C@H]3F)[nH]n2)n1)c1ccc2[nH]ccc2n1]

The title compounds were prepared following the procedures according to Examples 18 and 19, using 2-chloro-N-(5-((1R,2S)-2-fluorocyclopropyl)-1H-pyrazol-3-yl)pyrimidin-4-amine (referential example 6) in place of 2-chloro-N-(5-cyclopropyl-1H-pyrazol-3-yl)pyrimidin-4-amine (referential example 1) as the starting material. Chiral SFC separation afforded the following two enantiomers:

N²—((S)-1-(1H-pyrrolo[3,2-b]pyridin-5-yl)ethyl)-N⁴-(5-((1R,2S)-2-fluorocyclopropyl)-1H-pyrazol-3-yl)-N²-methylpyrimidine-2,4-diamine: NMR (400 MHz, DMSO-d⁶) δ 12.02 (br s, 1H), 11.21 (s, 1H), 9.41 (br s, 1H), 7.92 (d, J=5.6 Hz, 1H), 7.69 (d, J=8.4 Hz, 1H), 7.59 (t, J=2.9 Hz, 1H), 6.99 (d, J=8.0 Hz, 1H), 6.55 (s, 1H), 6.25 (br s, 3H), 4.79 (dd, J=63.9, 5.8 Hz, 1H), 2.85 (s, 3H), 2.40-2.28 (m, 1H), 1.60 (d, J=7.0 Hz, 3H), 1.54-1.39 (m, 1H), 1.07-0.95 (m, 1H); MS (ESI) m/z: 393.1 [M+1]⁺; SFC RT=0.60 min.

N²-((R)-1-(1H-pyrrolo[3,2-b]pyridin-5-yl)ethyl)-N⁴-(5-((1R,2S)-2-fluorocyclopropyl)-1H-pyrazol-3-yl)-N²-methylpyrimidine-2,4-diamine: ¹H NMR (400 MHz, DMSO-d⁶) δ 12.02 (br s, 1H), 11.21 (s, 1H), 9.41 (br s, 1H), 7.92 (d, J=5.6 Hz, 1H), 7.69 (d, J=8.4 Hz, 1H), 7.59 (t, J=2.9 Hz, 1H), 6.99 (d, J=8.0 Hz, 1H), 6.55 (s, 1H), 6.25 (br s, 3H), 4.79 (dd, J=63.9, 5.8 Hz, 1H), 2.85 (s, 3H), 2.40-2.28 (m, 1H), 1.60 (d, J=7.0 Hz, 3H), 1.54-1.39 (m, 1H), 1.07-0.95 (m, 1H); MS (ESI) m/z: 393.1 [M+1]⁺; SFC RT=0.38 min.

Example 30

N²-((S)-1-(1H-pyrrolo[3,2-b]pyridin-5-yl)ethyl)-N⁴-(5-((1R,2R)-2-fluorocyclopropyl)-1H-pyrazol-3-yl)pyrimidine-2,4-diamine (I-30)

The title compound was prepared following the procedure according to Example 9, using (S)-1-(1H-pyrrolo[3,2-b]pyridin-5-yl)ethanamine hydrochloride (referential example 17) and 2-chloro-N-(5-((1R,2R)-2-fluorocyclopropyl)-1H-pyrazol-3-yl)pyrimidin-4-amine (referential example 4) in place of (1H-pyrrolo[3,2-b]pyridin-5-yl)methanamine and 2-chloro-N-(5-cyclopropyl-1H-pyrazol-3-yl)pyrimidin-4-amine (referential example 1), respectively, as starting materials. ¹H NMR (400 MHz, DMSO-d⁶) δ 11.98 (br s, 1H), 11.18 (s, 1H), 9.33 (br s, 1H), 7.79 (d, J=5.6 Hz, 1H), 7.70 (d, J=8.4 Hz, 1H), 7.57 (s, 1H), 7.16 (d, J=8.3 Hz, 1H), 6.93 (br s, 1H), 6.53 (s, 1H), 6.40 (br s, 1H), 6.10 (br s, 1H), 5.21 (s, 1H), 4.90 (d, J=65.8 Hz, 1H), 2.10-1.99 (m, 1H), 1.49 (d, J=6.9 Hz, 3H), 1.33 (s, 1H), 1.24 (s, 1H); MS (ESI) m/k: 379.2 [M+1]⁺.

Example 31

N²-((S)-1-(1H-pyrrolo[3,2-b]pyridin-5-yl)ethyl)-N⁴-(5-((1S,2S)-2-fluorocyclopropyl)-1H-pyrazol-3-yl)pyrimidine-2,4-diamine formic acid salt (I-31)

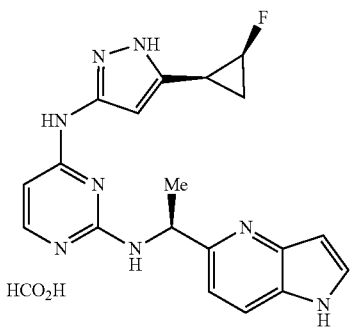 [SMILES: "HCO2H" ; C[C@H](Nc1nccc(Nc2cc([C@@H]3C[C@@H]3F)[nH]n2)n1)c1ccc2[nH]ccc2n1]

The title compound was prepared following the procedure according to Example 29, using 2-chloro-N-(5-((1S,2S)-2-fluorocyclopropyl)-1H-pyrazol-3-yl)pyrimidin-4-amine (referential example 5) in place of 2-chloro-N-(5-((1R,2R)-2-fluorocyclopropyl)-1H-pyrazol-3-yl)pyrimidin-4-amine (referential example 4D) as the starting material: ¹H NMR (400 MHz, DMSO-d⁶) δ 11.19 (s, 1H), 9.49 (br s, 1H), 7.79 (d, J=5.7 Hz, 1H), 731 (d, J=8.4 Hz, 1H), 7.57 (s, 1H), 7.30-7.12 (br s, 1H), 7.16 (d, J=8.4 Hz, 1H), 6.54 (s, 1H), 6.07 (br s, 2H), 5.25-5.15 (m, 1H), 5.03-4.75 (m, 2H), 2.09-2.00 (m, 1H), 1.49 (d, J=6.9 Hz, 3H), 1.38 (br s, 1H), 1.23 (br s, 1H); 1H not seen. MS (ESI) m/z: 379.1 [M+1]⁺.

Example 32

N²-((S)-1-(1H-pyrrolo[3,2-b]pyridin-5-yl)ethyl)-N⁴-(5-((1S,2R)-2-fluorocyclopropyl)-1H-pyrazol-3-yl)pyrimidine-2,4-diamine (I-32)

The title compound was prepared following the procedure according to Example 29, using 2-chloro-N-(5-((1S,2R)-2-fluorocyclopropyl)-1H-pyrazol-3-yl)pyrimidin-4-amine (referential example 7) in place of 2-chloro-N-(5-((1R,2R)-2-fluorocyclopropyl)-1H-pyrazol-3-yl) pyrimidin-4-amine (referential example 5) as the starting material. ¹H NMR (400 MHz, DMSO-d⁶) δ 12.88-12.49 (br s, 1H), 11.99 (br s, 1H), 11.18 (s, 1H), 9.41 (br s, 2H), 7.78 (d, J=5.6 Hz, 1H), 7.69 (cl, J=8 Hz, 1H), 7.57 (s, 1H), 7.18 (s, 1H), 6.53 (s, 1H), 6.00 (br s, 1H), 5.19 (br s, 1H), 4.88 (d, J=66.2 Hz, 1H), 2.44-2.28 (m, 1H), 1.49 (d, J=6.9 Hz, 4H), 1.25-1.06 (m, 1H); MS (ESI) m/z: 379.1 [M+1]⁺.

Example 33

N²-((3H-imidazo[4,5-c]pyridin-7-yl)methyl)-N⁴-(5-cyclopropyl-1H-pyrazol-3-yl)pyrimidine-2,4-diamine (I-33)

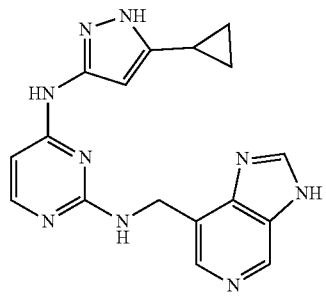 [SMILES: c1cc(Nc2cc(C3CC3)[nH]n2)nc(NCc2cncc3[nH]cnc23)n1]

The title compound was prepared following the procedure according to step 1 of referential example 7, using (3-(tetrahydro-2H-pyran-2-yl)-3H-imidazo[4,5-c]pyridin-7-yl)-methanamine (referential example 19) in place of tert-butyl 5-(1-aminoethyl)-1H-pyrrolo[2,3-c]-pyridine-1-carboxylate (referential example 17) as the starting material. MS (ESI) m/z: 348.1 [M+1]⁺.

Example 34

N²-((3H-imidazo[4,5-c]pyridin-7-yl)methyl)-N⁴-(5-cyclopropyl-1H-pyrazol-3-yl)-5-fluoropyrimidine-2,4-diamine (I-34)

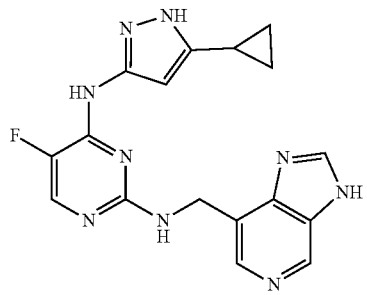 [SMILES: Fc1cnc(NCc2cncc3[nH]cnc23)nc1Nc1cc(C2CC2)[nH]n1]

The title compound was prepared following the procedure according to Example 33, using 2-chloro-N-(5-cyclopropyl-1H-pyrazol-3-yl)-5-fluoropyrimidin-4-amine (referential example 2) in place of 20 (referential example 1) as the starting material. MS (ESI) m/z: 366.1 [M+1]⁺.

Examples 35 and 36

(S)—N²-(1-(5H-pyrrolo[3,2-d]pyrimidin-2-yl)ethyl)-N⁴-(5-cyclopropyl-1H-pyrazol-3-yl)pyrimidine-2,4-diamine (I-35) and (R)—N²-(1-(5H-pyrrolo[3,2-d]pyrimidin-2-yl)ethyl)-N⁴-(5-cyclopropyl-1H-pyrazol-3-yl)pyrimidine-2,4-diamine (I-36)

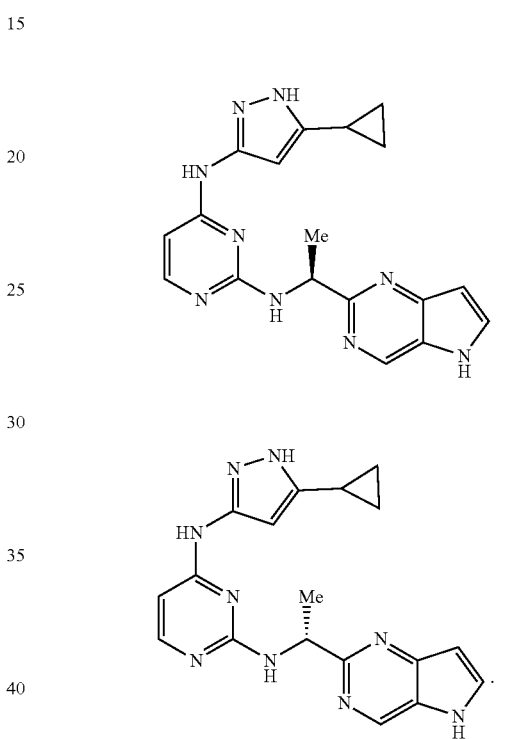

The title compounds were prepared following the procedures according to Examples 7 and 8, using 1-(5H-pyrrolo[3,2-d]pyrimidin-2-yl)ethanamine hydrochloride (referential example 20) in place of tert-butyl 5-(1-aminoethyl)-1H-pyrrolo[2,3-c]-pyridine-1-carboxylate (referential example 17) as the starting material. Chiral SFC separation afforded the following two enantiomers:

(S)—N²-(1-(5H-pyrrolo[3,2-d]pyrimidin-2-yl)ethyl)-N⁴-(5-cyclopropyl-1H-pyrazol-3-yl)pyrimidine-2,4-diamine: ¹H NMR (400 MHz, DMSO-d₆) δ 11.87 (br s, 1H), 11.71 (s, 1H), 9.40 (br s, 1H), 8.87 (s, 1H), 7.86 (t, J=2.9 Hz, 1H), 7.77 (d, J=5.7 Hz, 1H), 6.87 (br s, 1H), 6.57 (s, 1H), 6.08 (br s, 2H), 5.32-5.19 (m, 1H), 1.93-1.78 (m, 1H), 1.51 (d, J=6.8 Hz, 3H), 0.92 (s, 2H), 0.73 (s, 2H); MS (ESI) ray/z: 362.0 [M+1]⁺; SFC RT=0.52 min.

(R)—N²-(1-(5H-pyrrolo[3,2-d]pyrimidin-2-yl)ethyl)-N⁴-(5-cyclopropyl-1H-pyrazol-3-yl)pyrimidine-2,4-diamine: ¹H NMR (400 MHz, DMSO-d⁶) δ 12.00 (br s, 1H), 11.71 (s, 1H), 9.40 (br s, 1H), 8.87 (s, 1H), 7.86 (t, J=2.9 Hz, 1H), 7.77 (d, J=5.7 Hz, 1H), 6.87 (s, 1H), 6.57 (s, 1H), 6.09 (br s, 2H), 5.32-5.18 (m, 1H), 1.93-1.79 (m, 1H), 1.51 (d, J=6.8 Hz, 3H), 0.92 (s, 2H), 0.73 (s, 2H); MS (ESI) m/z: 362.0 [M+1]⁺; SFC RT=0.65 min.

Example 37

N²-(1-(6-chloro-1H-pyrrolo[3,2-b]pyridin-5-yl)ethyl)-N⁴-(5-cyclopropyl-1H-pyrazol-3-yl)pyrimidine-2,4-diamine (I-37)

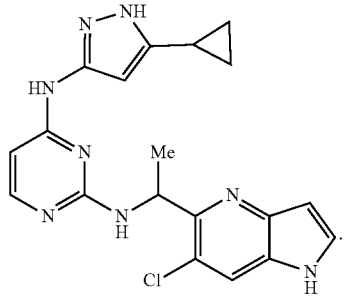 [SMILES: CC(Nc1nccc(Nc2cc(C3CC3)[nH]n2)n1)c1nc2cc[nH]c2cc1Cl]

step 1: A mixture of 1-(6-chloro-1-tosyl-1H-pyrrolo[3,2-b]pyridin-5-yl)ethanamine (180 mg, 0.51 mmol), DIPEA (133 mg, 1.03 mmol), and 2-chloro-N-(5-cyclopropyl-1H-pyrazol-3-yl)pyrimidin-4-amine (97 mg, 0.41 mmol) in 2,4-dimethyl-3-pentanol (0.5 mL) was heated at 140° C. for 18 h. The reaction mixture was concentrated under reduced pressure to afford a crude 320 mg (41%) of N²-(1-(6-chloro-1-tosyl-1H-pyrrolo[3,2-b]pyridin-5-yl)ethyl)-N⁴-(5-cyclopropyl-1H-pyrazol-3-yl)pyrimidine-2,4-diamine as brown solid, which was used in the next step without further purification. MS (ESI): m/z=549.2 [M+1]⁺.

step 2: To a solution of N²-(1-(6-chloro-1-tosyl-1H-pyrrolo[3,2-b]pyridin-5-yl)ethyl)-N⁴-(5-cyclopropyl-1H-pyrazol-3-yl)pyrimidine-2,4-diamine (320 mg, 0.58 mmol) in methanol (5 mL) was added an aqueous solution of KOH (2 N, 5 mL). The mixture was heated at 100° C. for 3 h. The reaction mixture was quenched with a saturated NH₄Cl solution and extracted with EtOAc. The extract was washed with H₂O, dried (Na₂SO₄), filtered, and concentrated under reduced pressure. The crude product was purified by preparative HPLC to afford 30 mg (26%) of N²-(1-(6-chloro-1H-pyrrolo[3,2-b]pyridin-5-yl)ethyl)-N⁴-(5-cyclopropyl-1H-pyrazol-3-yl)pyrimidine-2,4-diamine as white solid. ¹H NMR (500 MHz, CD₃OD): δ 11.93 (s, 1H), 11.41 (s, 1H), 9.40 (m, 1H), 7.80 (d, 2H), 7.69 (s, 1H), 6.60 (m, 2H), 6.27 (d, 2H), 5.63 (m, 1H), 1.88 (s, 1H), 1.45 (d, 3H), 0.94 (m, 2H), 0.71 (m, 2H); MS (ESI): m/z=395.1 [M+1]⁺.

Example 38

N²-((1H-Pyrazolo[4,3-c]pyridin-4-yl)methyl)-N⁴-(5-cyclopropyl-1H-pyrazol-3-yl)pyrimidine-2,4-diamine (I-38)

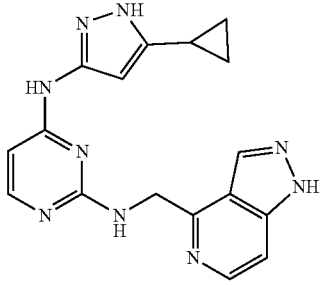 [SMILES: c1cc(Nc2cc(C3CC3)[nH]n2)nc(NCc2nccc3[nH]ncc23)n1]

step 1: A mixture of (1-tosyl-1H-pyrazolo[4,3-c]pyridin-4-yl)methanamine (300 mg, 1.3 mmol), 2-chloro-N-(5-cyclopropyl-1H-pyrazol-3-yl)pyrimidin-4-amine (258 mg, 1.05 mmol), and DIPEA (0.5 mL) in IPA (2 mL) was heated at 120° C. overnight. The reaction mixture was concentrated under reduced pressure to afford 400 mg (61%) of crude N⁴-(5-cyclopropyl-1H-pyrazol-3-yl)-N²-((1-tosyl-1H-pyrazolo[4,3-c]pyridin-4-yl)methyl)pyrimidine-2,4-diamine as yellow oil. MS (ESI): m/z=502.3 [M+1]⁺.

step 2: To a mixture of N⁴-(5-cyclopropyl-1H-pyrazol-3-yl)-N²-((1-tosyl-1H-pyrazolo[4,3-c]pyridin-4-yl)methyl)pyrimidine-2,4-diamine (400 mg, 0.80 mmol) in MeOH (5 mL) was added aqueous NaOH (2 N, 5 mL). The mixture was heated at reflux overnight. The reaction mixture was extracted with EtOAc (100 mL×3), dried (Na₂SO₄), filtered, and concentrated under reduced pressure. The residue was purified by preparative HPLC to afford 30 mg (6.3%) of N²41H-pyrazolo[4,3-c]pyridin-4-yl)methyl)-N⁴-(5-cyclopropyl-1H-pyrazol-3-yl)pyrimidine-2,4-diamine as yellow solid. ¹H NMR (500 MHz, DMSO-d₄) δ 9.44 (brs, 1H), 8.32 (brs, 1H), 8.23 (d, J=6 Hz, 1H), 7.80 (d, J=5 Hz, 1H), 7.40 (d, J=6 Hz, 1H), 6.14-5.99 (m, 2H), 4.87 (d, J=5.5 Hz, 2H), 1.80 (s, 1H), 0.88-0.87 (m, 2H), 0.66 (s, 2H); MS (ESI): m/z=348.1 [M+1]⁺.

Example 39

(S)—N⁴-(5-cyclopropyl-1H-pyrazol-3-yl)-N²-(1-(6-fluoro-1H-pyrrolo[3,2-b]pyridin-5-yl)ethyl)pyrimidine-2,4-diamine (I-39)

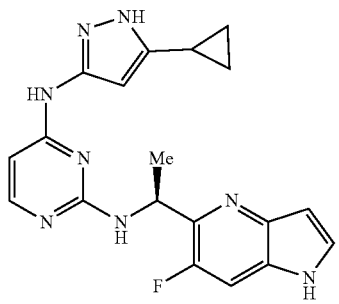 [SMILES: C[C@H](Nc1nccc(Nc2cc(C3CC3)[nH]n2)n1)c1nc2cc[nH]c2cc1F]

step 1: A mixture of 1-(6-fluoro-1-tosyl-1H-pyrrolo[3,2-b]pyridin-5-yl)ethanamine (500 mg, 1.5 mmol), 2-chloro-N-(5-cyclopropyl-1H-pyrazol-3-yl)pyrimidin-4-amine (353 mg, 1.5 mmol), and DIPEA (581 mg, 4.5 mmol) in 2,4-dimethylpentan-3-ol (2 mL) was heated at 135° C. for 15 h. The reaction mixture was concentrated under reduced pressure. The residue was purified by reverse phase chromatography to afford 180 mg (21%) of N⁴-(5-cyclopropyl-1H-pyrazol-3-yl)-N²-(1-(6-fluoro-1-tosyl-1H-pyrrolo[3,2-b]pyridin-5-yl)ethyl)pyrimidine-2,4-diamine as a white solid. MS (ESI): m/z=533.3 [M+H]⁺.

The chiral preparative HPLC of N⁴-(5-cyclopropyl-1H-pyrazol-3-yl)-N²-(1-(6-fluoro-1-tosyl-1H-pyrrolo[3,2-b]pyridin-5-yl)ethyl)pyrimidine-2,4-diamine afforded (S)—N⁴-(5-cyclopropyl-1H-pyrazol-3-yl)-N²-(1-(6-fluoro-1-tosyl-1H-pyrrolo[3,2-b]pyridin-5-yl)ethyl)pyrimidine-2,4-diamine as a yellow solid (120 mg) and (R)—N⁴-(5-cyclopropyl-1H-pyrazol-3-yl)-N²-(1-(6-fluoro-1-tosyl-1H-pyrrolo[3,2-b]pyridin-5-yl)ethyl)pyrimidine-2,4-diamine as a yellow solid (60 mg).

step 2: To a mixture of (S)—N⁴-(5-cyclopropyl-1H-pyrazol-3-yl)-N²-(1-(6-fluoro-1-tosyl-1H-pyrrolo[3,2-b]pyridin-5-yl)ethyl)pyrimidine-2,4-diamine (120 mg, 0.226 mmol) in MeOH (10 mL) was added aqueous NaOH (18 mg, 2 mL H₂O). The mixture was heated at 50° C. for 5 h. The reaction mixture was quenched by adding a sat'd, aq. NH₄Cl solution and extracted with EtOAc (50 mL×3), dried (Na₂SO₄), filtered, and concentrated under reduced pressure. The residue was purified by preparative HPLC to afford (S)—N⁴-(5-cyclopropyl-1H-pyrazol-3-yl)-N²-(1-(6-fluoro-1H-pyrrolo[3,2-b]pyridin-5-yl)ethyl)pyrimidine-2,4-diamine as white solid (25 mg, 30%). ¹H NMR (500 MHz, MeOD) δ 7.79-7.81 (d, 1H), 7.53-7.59 (m, 2H), 6.62 (s, 1H), 6.03-6.27 (m, 2H), 5.54-5.59 (m, 1H), 1.95 (m, 1H), 1.59 (m, 3H), 1.01 (m, 2H), 0.78 (m, 2H); MS (ESI): m/z=379.1 [M+1]⁺.

Example 40

N⁴-(5-Cyclopropyl-1H-pyrazol-3-yl)-N²-((6-fluoro-1H-pyrrolo[3,2-b]pyridin-5-yl)methyl)-N²-methylpyrimidine-2,4-diamine (I-40)

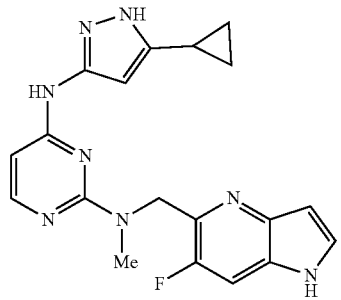 [SMILES: CN(Cc1nc2cc[nH]c2cc1F)c1nccc(Nc2cc(C3CC3)[nH]n2)n1]

step 1: A mixture of (6-fluoro-1-((2-(trimethylsilyl)ethoxy)methyl)-1H-pyrrolo[3,2-b]pyridin-5-yl)-N-methylmethanamine (50 mg, 0.17 mmol), 2-chloro-N-(5-cyclopropyl-1H-pyrazol-3-yl)pyrimidin-4-amine (38 mg, 0.17 mmol), and DIPEA (66 mg, 0.51 mmol) in 2,4-dimethylpentan-3-ol (2 mL) was heated at 135° C. for 15 h. The reaction mixture was concentrated under reduced pressure. The residue was purified by SiO₂ chromatography eluting with DCM/MeOH (10:1) to afford 40 mg (30%) of N⁴-(5-cyclopropyl-1H-pyrazol-3-yl)-N²-((6-fluoro-1-((2-(trimethylsilyl)ethoxy)methyl)-1H-pyrrolo[3,2-b]pyridin-5-yl)methyl)-N²-methylpyrimidine-2,4-diamine as a brown oil (40 mg, 30%). MS (ESI): m/z=509.4 [M+H]⁺.

step 2: A mixture of N⁴-(5-cyclopropyl-1H-pyrazol-3-yl)-N²-((6-fluoro-1-((2-(trimethylsilyl)ethoxy)methyl)-1H-pyrrolo[3,2-b]pyridin-5-yl)methyl)-N²-methylpyrimidine-2,4-diamine (40 mg, 0.1 mmol) and tetrabutyl ammonium fluoride (260 mg, 1 mmol) in THF (5 mL) was heated at 63° C. for 18 h. The reaction mixture was poured into water (10 mL) and the pH was adjusted to 10 by addition of an NH₄OH solution. The mixture was extracted with EtOAc (50 mL×3) and the combined extracts dried (MgSO₄), filtered, and concentrated under reduced pressure. The residue was purified by reverse phase preparative HPLC to afford 8 mg, (20%) of N⁴-(5-cyclopropyl-1H-pyrazol-3-yl)-N²-((6-fluoro-1H-pyrrolo[3,2-b]pyridin-5-yl)methyl)-N²-methylpyrimidine-2,4-diamine as a white solid. ¹H NMR (500 MHz, DMSO) δ 11.8 (brs, 1H), 11.3 (brs, 1H), 9.33 (brs, 1H), 7.85 (d, J=5 Hz, 1H), 7.65 (d, 0.1=10 Hz, 1H), 7.58 (d, J=3 Hz, 1H), 6.51 (s, 1H), 6.00-6.20 (brs, 2H), 5.06 (s, 2H), 3.16 (s, 3H), 1.81 (s, 1H), 0.85 (s, 2H), 0.59 (s, 2H); MS (ESI): m/z=379.3 [M+1]⁺.

Example 41

(R)—N²-(1-(3H-Imidazo[4,5-c]pyridin-6-yl)ethyl)-N⁴-(5-cyclopropyl)-1H-pyrazol-3-yl)pyrimidine-2,4-diamine (I-42) and (S)—N²-(1-(3H-Imidazo[4,5-c]pyridin-6-yl)ethyl)-N⁴-(5-cyclopropyl-1H-pyrazol-3-yl)pyrimidine-2,4-diamine (I-41)

step 1: A mixture of 2-chloro-N-(5-cyclopropyl-1H-pyrazol-3-yl)pyrimidin-4-amine (167 mg, 0.71 mmol), 1-(3-(4-methoxybenzyl)-3H-imidazo[4,5-c]pyridin-6-yl)ethanamine (200 mg, 0.71 mmol), DIPEA (275 mg, 2.31 mmol) in 2,4-dimethylpentan-3-ol (3.0 mL) in a sealed tube was heated at 120° C. overnight. The reaction mixture was concentrated under reduced pressure and the residue purified by SiO₂ chromatography eluting with DCM/MeOH (15:1) to 135 mg (61%) to afford 135 mg (56%) of N⁴-(5-cyclopropyl-1H-pyrazol-3-yl)-N²-(1-(3-(4-methoxybenzyl)-3H-imidazo[4,5-c]pyridin-6-yl)ethyl)pyrimidine-2,4-diamine as white solid. MS (ESI): m/z=482.2[M+1]⁺.

step 2: A mixture of N⁴-(5-cyclopropyl-1H-pyrazol-3-yl)-N²-(1-(3-(4-methoxybenzyl)-3H-imidazo[4,5-c]pyridin-6-yl)ethyl)pyrimidine-2,4-diamine (130 mg, 0.27 mmol) in TFA (3 mL) was heated at 70° C. for 2 h. The reaction mixture was concentrated under reduced pressure. The residue was purified by reverse phase preparative HPLC to afford 45 mg (46%) of N²-(1-(3H-imidazo[4,5-c]pyridin-6-yl)ethyl)-N⁴-(5-cyclopropyl-1H-pyrazol-3-yl)pyrimidine-2,4-diamine as white solid.

Chiral separation using preparative HPLC afforded (R)—N²-(1-(3H-imidazo[4,5-c]pyridin-6-yl)ethyl)-N⁴-(5-cyclopropyl-1H-pyrazol-3-yl)pyrimidine-2,4-diamine (11 mg) and (S)—N²-(1-(3H-imidazo[4,5-c]pyridin-6-yl)ethyl)-N⁴-(5-cyclopropyl-1H-pyrazol-3-yl)pyrimidine-2,4-diamine (11 mg).

(S)—N²-(1-(3H-imidazo[4,5-c]pyridin-6-yl)ethyl)-N⁴-(5-cyclopropyl-1H-pyrazol-3-yl)pyrimidine-2,4-diamine: ¹H NMR (500 MHz, MeOD-d₄) a 8.93 (s, 1H), 8.32 (s, 1H), 7.79-7.80 (d, 1H), 7.68 (s, 1H), 6.13-6.19 (brs, 1H), 6.10-6.11 (brs, 1H), 5.28-5.30 (dd, 1H), 1.86-1.92 (m, 1H), 1.64-1.65 (d, 3H), 0.93-1.02 (m, 2H), 0.67-0.73 (m, 2H); MS (EST): m/z=362.3 [M+1]⁺.

(R)—N²-(1-(3H-imidazo[4,5-c]pyridin-6-yl)ethyl)-N⁴-(5-cyclopropyl-1H-pyrazol-3-yl)pyrimidine-2,4-diamine: 1H NMR (500 MHz, MeOD-d₄) a 8.91 (s, 1H), 8.31 (s, 1H), 7.77-7.78 (d, 1H), 7.66 (s, 1H), 6.13-6.15 (brs, 1H), 6.10-6.11 (brs, 1H), 5.26-5.27 (dd, 1H), 1.84-1.90 (m, 1H), 1.62-1.63 (d, 3H), 0.92-0.99 (m, 2H), 0.64-0.71 (m, 2H); MS (ESI): m/z=362.3[M+1]⁺.

Example 42

N²-((1H-Pyrrolo[2,3-c]pyridin-4-yl)methyl)-N⁴-(5-cyclopropyl-1H-pyrazol-3-yl)-N²-methylpyrimidine-2,4-diamine (I-43)

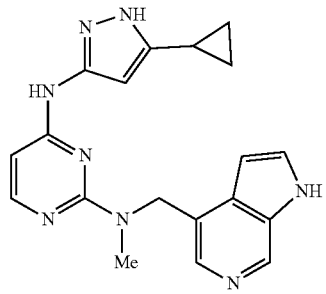 [SMILES: CN(Cc1cncc2[nH]ccc12)c1nccc(Nc2cc(C3CC3)[nH]n2)n1]

step 1: A mixture of N-methyl(1-((2-(trimethylsilyl)ethoxy)methyl)-1H-pyrrolo[2,3-c]pyridin-4-yl)methanamine (110 mg, 0.38 mmol), 2-chloro-N-(5-cyclopropyl-1H-pyrazol-3-yl)pyrimidin-4-amine (107 mg, 0.454 mmol), DIPEA (146 mg, 1.134 mmol) in 2,4-dimethylpentan-3-ol (2.0 mL) in a sealed tube was heated at 140° C. overnight. The reaction mixture was concentrated under reduced pressure. The residue was purified by SiO₂ chromatography eluting with DCM/MeOH (10:1) to afford 108 mg of N⁴-(5-cyclopropyl-1H-pyrazol-3-yl)-N²-methyl-N²-((1-((2-(trimethylsilyl)ethoxy)methyl)-1H-pyrrolo[2,3-c]pyridin-4-yl)methyl)pyrimidine-2,4-diamine as a yellow solid. MS (ESI): m/z=491.2 [M+1]⁺.

step 2: A mixture of N⁴-(5-cyclopropyl-1H-pyrazol-3-yl)-N²-methyl-N²-((1-((2-(trimethylsilyl)ethoxy)methyl)-1H-pyrrolo[2,3-c]pyridin-4-yl)methyl)pyrimidine-2,4-diamine (108 mg, 0.22 mmol) and tetrabutyl ammonium fluoride (580 mg, 2.2 mmol) in tetrahydrofuran (20 mL) was heated at 80° C. for 18 h. The reaction mixture was poured into water (100 mL) and the pH was adjusted to ca. 10 by adding an NH₄OH solution. The mixture was extracted with EtOAc (50 mL×3) and the combined extracts dried (MgSO₄), filtered, and concentrated under reduced pressure. The residue was purified by reverse phase preparative HPLC to afford 18 mg (22.7%) of N²-((1H-pyrrolo[2,3-c]pyridin-4-yl)methyl)-N⁴-(5-cyclopropyl-1H-pyrazol-3-yl)-N²-methylpyrimidine-2,4-diamine as a white solid. ¹H NMR (500 MHZ, MeOD-d₄) δ 8.62 (s, 1H), 7.82 (d, 2H), 7.59 (d, 1H), 6.59 (d, 1H), 6.12 (d, 1H), 5.84 (brs, 1H), 5.13 (s, 2H), 3.03 (s, 3H), 1.58 (brs, 1H), 0.68 (d, 2H), 0.27 (d, 2H); MS (ESI): m/z=361.2 [M+1]⁺.

Example 43

G02668924 and G02668923

(S)—N²-(1-(5H-pyrrolo[3,2-d]pyrimidin-2-yl)ethyl)-N⁴-(5-cyclopropyl-1H-pyrazol-3-yl)-N²-ethylpyrimidine-2,4-diamine (I-45) and (R)—N²-(1-(5H-pyrrolo[3,2-d]pyrimidin-2-yl)ethyl)-N⁴-(5-cyclopropyl-1H-pyrazol-3-yl)-N²-ethylpyrimidine-2,4-diamine (I-44)

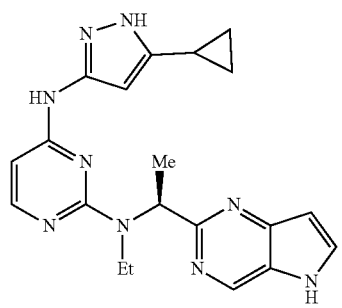
(I-45)

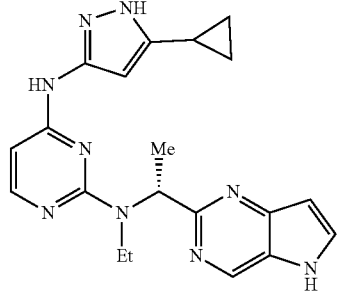
(I-44)

step 1: A vial was charged with 2-chloro-N-(5-cyclopropyl-1H-pyrazol-3-yl)-pyrimidin-4-amine (60 mg, 0.25 mmol), N-ethyl-1-(5-((2-(trimethylsilyl)ethoxy)methyl)-5H-pyrrolo[3,2-d]pyrimidin-2-yl)ethanamine (367.0 mg, 1.14 mmol), DIPEA (1.3 mL) and n-BuOH (3.5 mL), sealed and heated at 115° C. for 96 h. The reaction mixture was poured into EtOAc, and the organic layer was washed with water and brine, dried (Na₂SO₄), filtered, and concentrated under reduced pressure. The crude product was purified by SiO₂ chromatography to afford 103.9 mg (52.35%) of N⁴-(5-cyclopropyl-1H-pyrazol-3-yl)-N²-ethyl-N²-(1-(5-((2-(trimethylsilyl)ethoxy)methyl)-5H-pyrrolo[3,2-d]pyrimidin-2-yl)ethyl)pyrimidine-2,4-diamine as a racemic mixture. MS (ESI) m/z: 520.3 [M+1]⁺.

step 2: To a stirred solution of N⁴-(5-cyclopropyl-1H-pyrazol-3-yl)-N²-ethyl-N²-(1-(5-((2-(trimethylsilyl)ethoxy)methyl)-5H-pyrrolo[3,2-d]pyrimidin-2-yl)ethyl)pyrimidine-2,4-diamine (103.9 mg, 0.20 mmol) in anhydrous DMF (4.7 mL) was added ethylenediamine (0.10 mL, 1.60 mmol) followed by tetrabutylammonium fluoride (1M in THF, 0.60 mL, 0.60 mmol), and the reaction mixture was stirred at 80° C. under N₂ for 20 h. The reaction mixture was poured into EtOAc, and the organic layer was washed with 10% aq. NaOH solution, water and brine, dried (Na₂SO₄), filtered, and concentrated under reduced pressure. The crude product was purified by SiO₂ chromatography to afford 50.4 mg (64.7%) of racemic N²-(1-(5H-pyrrolo[3,2-d]pyrimidin-2-yl)ethyl)-N⁴-(5-cyclopropyl-1H-pyrazol-3-yl)-N²-ethylpyrimidine-2,4-diamine. Chiral SFC chromatography of racemic N²-(1-(5H-pyrrolo[3,2-d]pyrimidin-2-yl)ethyl)-N⁴-(5-cyclopropyl-1H-pyrazol-3-yl)-N²-ethylpyrimidine-2,4-diamine (50.4 mg, 0.13 mmol) afforded the corresponding two enantiomers:

(S)—N²-(1-(5H-pyrrolo[3,2-d]pyrimidin-2-yl)ethyl)-N⁴-(5-cyclopropyl-1H-pyrazol-3-yl)-N²-ethylpyrimidine-2,4-diamine (19.5 mg, 38.7%). ¹H NMR (400 MHz, DMSO) δ 11.88 (br s, 1H), 11.71 (s, 1H), 9.30 (br s, 1H), 8.86 (s, 1H), 7.85 (t, J=2.8 Hz, 2H), 6.57 (d, J=3.0 Hz, 1H), 6.40-6.03 (m, 3H), 3.42-3.34 (m, 1H), 3.69-3.54 (m, 1H), 1.82 (ddd, J=13.5, 8.7, 5.1 Hz, 1H), 1.68-1.56 (m, 3H), 0.94-0.78 (m, 4H), 0.61 (s, 2H), 1H not seen; MS (ESI) m/z: 390.1 [M+1]⁺; SFC retention time=0.34 min.

(R)—N²-(1-(5H-pyrrolo[3,2-d]pyrimidin-2-yl)ethyl)-N⁴-(5-cyclopropyl-1H-pyrazol-3-yl)-N²-ethylpyrimidine-2,4-diamine (17.0 mg, 33.7%). ¹H NMR (400 MHz, DMSO) δ 11.89 (br s, 1H), 11.71 (s, 1H), 9.29 (br s, 1H), 8.86 (s, 1H), 7.89-7.82 (m, 2H), 6.57 (d, J=3.0 Hz, 1H), 6.42-5.99 (m, 3H), 3.42-3.33 (m, 1H), 3.69-3.53 (m, 1H), 1.82 (ddd, J=13.5, 8.5, 5.0 Hz, 1H), 1.63 (d, J=7.1 Hz, 3H), 0.94-0.77 (m, 4H), 0.62 (s, 2H), 1H not seen; MS (ESI) m/z: 390.1 [M+1]$^+$; SFC retention time=0.81 min.

Example 44

(S)—N$^2$-(1-(3-chloro-1H-pyrrolo[3,2-b]pyridin-5-yl)ethyl)-N$^4$-(5-((1R,2S)-2-fluorocyclo-propyl)-1H-pyrazol-3-yl)pyrimidine-2,4-diamine (I-46)

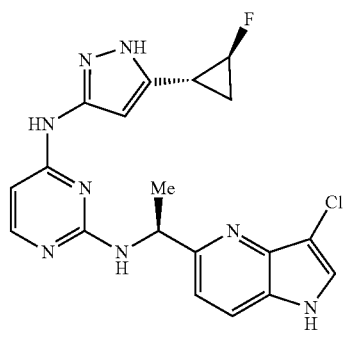 [SMILES: C[C@H](Nc1nccc(Nc2cc([C@H]3C[C@@H]3F)[nH]n2)n1)c1ccc2[nH]cc(Cl)c2n1]

The title compound was prepared following the procedure according to Example 43, using 2-chloro-N45-[(1R,2S)-2-fluorocyclopropyl]-1H-pyrazol-3-yl)pyrimidin-4-amine in place of 2-chloro-N-(5-cyclopropyl-1H-pyrazol-3-yl)-pyrimidin-4-amine and (S)-1-(3-chloro-1H-pyrrolo[3,2-b]pyridin-5-yl)ethanamine hydrochloride in place of N-ethyl-1-(5-((2-(trimethylsilyl)ethoxy)methyl)-5H-pyrrolo[3,2-d]pyrimidin-2-yl)ethanamine. $^1$H NMR (400 MHz, DMSO) δ 12.68 (br s, 0.4H, rotamer), 11.94 (br s, 0.6H, rotamer), 11.50 (s, 1H), 10.01-9.84 (br s, 0.4H, rotamer), 9.34 (br s, 0.6H, rotamer), 7.82-7.72 (m, 2H), 7.26 (d, J=7.9 Hz, 1H), 7.09 (br s, 1H), 6.13 (br s, 1H), 5.92 (br s, 1H), 5.54 (br s, 1H), 5.21 (t, J=7.2 Hz, 1H), 4.92 (br s, 1H), 4.76 (br s, 1H), 2.41-2.25 (m, 1H), 1.51 (d, J=6.9 Hz, 3H), 1.08 (br s, 1H), 1H not seen; MS (ESI) m/z: 413.1 [M+1]$^+$.

Example 48

GST-PAK1-KD (Kinase Domain) IC$_{50}$ Biochemical Assay Protocol

Activity of human recombinant GST-PAK1-KD protein was assessed in vitro assay by observing the phosphorylation of a fluorogenic peptide substrate. Catalytically active GST-tagged human recombinant PAK1-KD protein (residues #249-545 of human PAK1, UniProtKP/Swiss Q13153 with His6-GST fusion protein on the N-terminus) was cloned into a pAcGP67 baculovirus expression vector (EMD Biosciences) and infected into Sf9 cells.

The activity/inhibition of GST-PAK1-KD was estimated by measuring the phosphorylation of a fluorogenic peptide substrate (5FAM-RRRLSFAEPG) using a microfluidic mobility shift assay. The peptide substrate is a consensus sequence based on various PAK1 substrates reported in the scientific literature. The 20 μL assay mixtures contained 25 mM Tris-HCl (pH 7.5), 1 mM DTT, 0.01% Triton X-100, 10 mM MgCl$_2$, 5 mM β-glycerophosphate, 0.1 mM Na$_3$VO$_4$, 0.1% BGG (bovine gamma globulin), 1 μM peptide substrate (5FAM-RRRLSFAEPG), and 250 μM GST-PAK1-KD. Incubations were carried out at 22° C. in MatriCal MP101 384-well Metriplates™. Prior to the assay, GST-PAK1-KD and test compounds were preincubated together in assay buffer at 2× concentration (5 μL of 500 μM enzyme and 5 μL of serially diluted compound) for 10 min, and the assay was initiated by the addition of 10 μL assay buffer containing 2 μM peptide substrate (2×) and 80 μM ATP (2×). Following the 30-minute incubation, the assay mixtures were quenched by the addition of 3 μL of 250 mM EDTA, and the substrate and phosphorylated product were separated by capillary electrophoresis and detected using LabChip® Caliper 3000 (Caliper Life Sciences).

TABLE II

| Cpd. No. | PAK1[1] inhibition K$_i$ (μM) | MEK1(S298)[2] phosphorylation IC$_{50}$ (μM) | Cpd. No. | PAK1[1] inhibition K$_i$ (μM) | MEK1(S298)[2] phosphorylation IC$_{50}$ (μM) |
|---|---|---|---|---|---|
| I-12 | 0.016 | 0.0455 | 1-35 | 0.003 | N/A |
| I-7 | 0.005 | 0.0684 | 1-33 | 0.494 | N/A |
| I-6 | 0.072 | 0.709 | 1.28 | 0.008 | 0.0531 |
| I-4 | 0.060 | 0.325 | 1-16 | 0.022 | 0.0726 |
| I-10 | 0.067 | 1.1 | 1-18 | 0.024 | 0.221 |
| I-31 | 0.133 | N/A | 1-24 | 0.052 | 0.191 |

[1]GST-PAK1-KD Inhibition Assay - Example 37
[2]MEK1(S298)$^2$ Phosphorylation Assay - Example 38

Example 49

Cellular PAK IC$_{50}$ Assay Protocol

Group I PAKs (PAK1-3) are activated upon binding to the Rho GTPases, Rac 1 and Cdc42. Activated group I PAKs phosphorylate MEK1 at Serine 298 (S298), one of the two sites in the catalytic domain that is important for stable association between Raf and MEK1 and subsequent MAPK activation. The inhibition of group I PAKs in EBC1 cells is assessed by detecting changes in the level of MEK1 phosphorylation at S298 using homogenous time-resolved fluorescence (HTRF). Inhibitory activity was estimated by treating 2×10$^4$ EBC1 cells for 2 h with PAK inhibitors in media containing 0.1% FBS. Following inhibitor treatment, cells were lysed with 25 μL of 1× cellular kinase lysis buffer (Cisbio) containing 1× cellular kinase blocking reagent (Cisbio). Cellular lysis was carried out at 4° C. for 2 h with constant shaking before lysate (16 μL) was transferred to white 384-well ProxiPlates™ (Perkin Elmer). Anti-total MEK1 antibody labeled with Europium cryptate donor (1 ng/well) (Cell Signaling Technologies catalog number 2352) and anti-phospho MEK1 (S298) antibody labeled with d2 acceptor (Cell Signaling Technologies catalog number 9128) (10 ng/well) were prepared in 1× detection buffer (CisBio) and added to each well of the assay plate and allowed to incubate at RT overnight. The following day the fluorescence emission from each well was measured in EnVision® (Perkin Elmer) at an excitation of 330 nm and dual emission wavelengths of 615 nm and 665 nm. The signal in each well at 665 nm was multiplied by 10,000 and divided by the signal in the same well at 615 nm to obtain a ratio. Ratio values ([665*10, 000]÷615) were plotted as a function of the concentration of compound to determine $IC_{50}$ values.

Example 50

Pharmaceutical compositions of the subject Compounds for administration via several routes can be prepared as described in this Example.

Composition for Oral Administration (A)

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula I wherein:

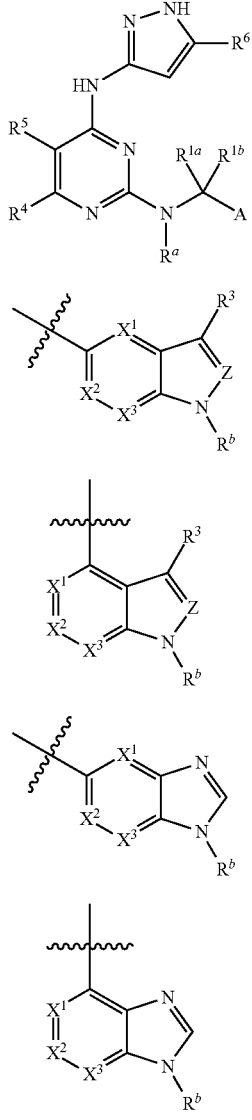

A is A-1, A-2 or A-3 wherein one of $X^1$, $X^2$ or $X^3$ is N and the remainder of $X^1$, $X^2$, and $X^3$ are $CR^2$ or when A is A-1, both of $X^1$ and $X^2$ are N and $X^3$ is $CR^2$;

Z is N or $CR^2$;

$R^{1a}$ and $R^{1b}$ are (i) independently hydrogen, $C_{1-6}$ alkyl or $C_{1-6}$ haloalkyl, or (ii) together with the carbon to which they are attached form a $C_{3-7}$ cycloalkane or an oxetane, tetrahydrofuran or tetrahydropyran;

$R^2$ is independently in each occurrence cyano, $C_{1-6}$ alkyl, —$OR^7$, $C_{1-6}$ haloalkyl, $C_{1-6}$ haloalkoxy, halogen or oxetane;

$R^3$ is hydrogen, halogen, $C_{1-6}$ alkyl, $C_{1-6}$ haloalkyl, $C_{1-6}$ acyl, $C_{1-3}$ haloalkanoyl, $C_{3-7}$ cycloalkyl or a $C_{3-6}$ heterocycle group with one oxygen atom;

$R^4$ is hydrogen, $C_{1-6}$ alkyl, $C_{1-6}$ haloalkyl, —$OR^7$, $C_{3-7}$ cycloalkyl or a $C_{3-6}$ heterocycle with one oxygen atom;

$R^5$ is hydrogen, halogen, $C_{1-6}$ alkyl, $C_{1-6}$ haloalkyl, CN or $C_{1-3}$-alkoxy;

$R^6$ is selected from the group consisting of (i) $C_{1-10}$ alkyl, (ii) $C_{1-10}$ haloalkyl, (iii) optionally substituted $C_{3-7}$ cycloalkyl (iv) $C_{3-7}$ cycloalkyl-$C_{1-6}$ alkyl, (v) $[(R^8)_2]_{0-6}$, $OR^7$ (vi) $C_{3-7}$ heterocyclyl and (vii) $C_{3-7}$ heterocyclyl-$C_{1-6}$ alkyl;

$R^7$ is independently in each occurrence $C_{1-10}$ alkyl, $C_{1-6}$ haloalkyl, $C_{3-7}$ cycloalkyl, $C_{3-7}$ cycloalkyl-$C_{1-6}$ alkyl, phenyl-$C_{1-6}$ alkyl, phenyl;

$R^8$ is independently in each occurrence hydrogen or C1-6 alkyl;

$R^b$ is hydrogen or $C_{1-6}$ alkyl;

$R^a$ is (a) hydrogen, (b) $C_{1-6}$ alkyl optionally substituted by one or two groups selected from the group consisting of hydroxyl, $C_{1-3}$ alkoxy or $NR^cR^d$ wherein $R^c$ and $R^d$ are (i) independently hydrogen or $C_{1-3}$ alkyl or (ii) together with the nitrogen to which they are attached form a pyrrolidine, piperidine or azetidine ring, (c) $C_{3-7}$ cycloalkyl or (d) a 4 to 7 member heterocycle containing O or $NR^e$ wherein $R^e$ is hydrogen of $C_{1-3}$ alkyl;

said cycloalkyl in each occurrence is independently optionally substituted with $C_{1-6}$ alkyl, halogen or optionally substituted phenyl;

said phenyl in each occurrence is independently optionally substituted with $C_{1-6}$ alkyl, halogen, $C_{1-6}$ alkoxy;

said heterocyclyl is independently substituted with halogen or $C_{1-6}$ alkyl; or, a pharmaceutically acceptable salt thereof.

2. The compound according to claim 1 wherein A is A-1, $X^1$ is N and $X^2$, $X^3$ and Z are independently $CR^2$.

3. The compound according to claim 1 wherein A is A-1, $X^2$ is N and $X^1$; $X^3$ and Z are independently $CR^2$.

4. The compound according to claim 1 wherein A is A-2, $X^1$ is N and $X^2$, $X^3$ and Z are independently $CR^2$.

5. The compound according to claim 1 wherein A is A-2, $X^2$ is N and $X^1$, $X^3$ and Z are independently $CR^2$.

6. The compound according to claim 1 wherein A is A-2, $X^3$ is N and $X^1$, $X^3$ and Z are independently $CR^2$.

7. The compound according to claim 1 wherein A is A-4, $X^2$ is N and $X^1$ and $X^3$ are independently $CR^2$.

8. The compound according to claim 1 wherein A is A-1, $X^1$ and $X^2$ are N and $X^3$ and Z are independently $CR^2$.

9. A compound according to claim 1 wherein $R^{1a}$ is hydrogen or $C_{1-6}$ alkyl and $R^{1b}$ is hydrogen.

10. The compound of claim 9 wherein $R^{1a}$ is methyl and the carbon to which it is attached is in the S configuration.

11. The compound according to any one of claims 1 to 10 wherein $R^a$ is hydrogen or $C_{1-6}$ alkyl optionally substituted by one or two groups selected from the group consisting of hydroxyl, $C_{1-3}$ alkoxy or $NR^cR^d$ wherein $R^c$ and $R^d$ are (i) independently hydrogen or $C_{1-3}$ alkyl or (ii) together with the nitrogen to which they are attached form a pyrrolidine, piperidine or azetidine ring, (c) $C_{3-7}$ cycloalkyl or (d) a 4 to 7 member heterocycle containing O or $NR^e$ wherein $R^e$ is hydrogen of $C_{1-3}$ alkyl.

12. The compound according to claim 1 wherein A is independently substituted by at least one halogen, $C_{1-6}$ alkyl or $C_{1-6}$ alkoxy.

13. The compound according to claim 1 wherein $R^6$ is optionally substituted cycloalkyl.

14. The compound according to claim 13 wherein $R^6$ is cyclopropyl substituted by at least one fluorine atom.

15. The compound according to claim 1 wherein:

$R^{1a}$ is hydrogen or $C_{1-6}$ alkyl and $R^{1b}$ is hydrogen;

$R^a$ is (a) hydrogen, (b) $C_{1-6}$ alkyl optionally substituted by one or two groups selected from the group consisting of hydroxyl, $C_{1-3}$ alkoxy or $NR^cR^d$ wherein $R^c$ and $R^d$ are (i) independently hydrogen or $C_{1-3}$ alkyl or (ii) together with the nitrogen to which they are attached form a pyrrolidine, piperidine or azetidine ring, (c) $C_{3-7}$ cycloalkyl or (d) a 4 to 7 member heterocycle containing O or $NR^e$ wherein $R^e$ is hydrogen of $C_{1-3}$ alkyl; and $R^6$ is cyclopropyl substituted by at least one fluorine atom.

16. The compound according to claim 1 which compound is selected from the group consisting of:

$N^4$-(5-cyclopropyl-1H-pyrazol-3-yl)-$N^2$-(1H-pyrrolo[2,3-c]pyridin-4-ylmethyl)-pyrimidine-2,4-diamine;
$N^4$-(5-cyclopropyl-1H-pyrazol-3-yl)-$N^2$-(1H-pyrrolo[2,3-b]pyridin-4-ylmethyl)-pyrimidine-2,4-diamine;
$N^4$-(5-cyclopropyl-1H-pyrazol-3-yl)-$N^2$-(1H-pyrrolo[3,2-c]pyridin-4-ylmethyl)-pyrimidine-2,4-diamine;
$N^4$-(5-cyclopropyl-1H-pyrazol-3-yl)-$N^2$-[1H-pyrrolo[3,2-c]pyridin-4-yl)-ethyl]-pyrimidine-2,4-diamine;
$N^4$-(5-cyclopropyl-1H-pyrazol-3-yl)-$N^2$-[1H-pyrrolo[3,2-c]pyridin-4-yl)-ethyl]-pyrimidine-2,4-diamine;
$N^4$-(5-cyclopropyl-1H-pyrazol-3-yl)-$N^2$-(1H-pyrrolo[2,3-b]pyridin-5-ylmethyl)-pyrimidine-2,4-diamine;
$N^4$-(5-cyclopropyl-1H-pyrazol-3-yl)-$N^2$-[1H-pyrrolo[2,3-c]pyridin-5-yl)-ethyl]-pyrimidine-2,4-diamine;
$N^4$-(5-cyclopropyl-1H-pyrazol-3-yl)-$N^2$-[1H-pyrrolo[2,3-c]pyridine-5-yl)-ethyl]-pyrimidine-2,4-diamine;
$N^4$-(5-cyclopropyl-1H-pyrazol-3-yl)-$N^2$-(1H-pyrrolo[3,2-b]pyridin-5-ylmethyl)-pyrimidine-2,4-diamine;
$N^4$-(5-cyclopropyl-1H-pyrazol-3-yl)-$N^2$-methyl-$N^2$-(1H-pyrrolo[3,2-b]pyridin-5-ylmethyl)-pyrimidine-2,4-diamine;
$N^2$-[1-(3-chloro-1H-pyrrolo[3,2-b]pyridin-5-yl)-ethyl]-$N^4$-(5-cyclopropyl-1H-pyrazol-3-yl)-pyrimidine-2,4-diamine;
$N^4$-(5-cyclopropyl-1H-pyrazol-3-yl)-$N^2$-[(S)-1-(1H-pyrrolo[3,2-b]pyridin-5-yl)-ethyl]-pyrimidine-2,4-diamine;
$N^4$-(5-cyclopropyl-1H-pyrazol-3-yl)-$N^2$-[(R)-1-(1H-pyrrolo[3,2-b]pyridin-5-yl)-ethyl]-pyrimidine-2,4-diamine;
$N^4$-(5-cyclopropyl-1H-pyrazol-3-yl)-5-fluoro-$N^2$-[(S)-1-(1H-pyrrolo[3,2-b]pyridin-5-yl)-ethyl]-pyrimidine-2,4-diamine;
$N^4$-(5-cyclopropyl-1H-pyrazol-3-yl)-5-fluoro-$N^2$-[(R)-1-(1H-pyrrolo[3,2-b]pyridin-5-yl)-ethyl]-pyrimidine-2,4-diamine;
$N^4$-[5-(3,3-difluoro-cyclobutyl)-1H-pyrazol-3-yl]-$N^2$-[(S)-1-(1H-pyrrolo[3,2-b]pyridin-5-yl)-ethyl]-pyrimidine-2,4-diamine;
$N^4$-[5-(3,3-difluoro-cyclobutyl)-1H-pyrazol-3-yl]-$N^2$-[(R)-1-(1H-pyrrolo[3,2-b]pyridin-5-yl)-ethyl]-pyrimidine-2,4-diamine;
$N^4$-(5-cyclopropyl-1H-pyrazol-3-yl)-$N^2$-methyl-$N^2$-[(S)-1-(1H-pyrrolo[3,2-b]pyridin-5-yl)-ethyl]-pyrimidine-2,4-diamine;
$N^4$-(5-cyclopropyl-1H-pyrazol-3-yl)-$N^2$-methyl-$N^2$-[(R)-1-(1H-pyrrolo[3,2-b]pyridin-5-yl)-ethyl]-pyrimidine-2,4-diamine;
$N^4$-(5-cyclopropyl-1H-pyrazol-3-yl)-5-fluoro-$N^2$-methyl-$N^2$-[(S)-1-(1H-pyrrolo[3,2-b]pyridin-5-yl)-ethyl]-pyrimidine-2,4-diamine;
$N^4$-(5-cyclopropyl-1H-pyrazol-3-yl)-5-fluoro-$N^2$-methyl-$N^2$-[(R)-1-(1H-pyrrolo[3,2-b]pyridin-5-yl)-ethyl]-pyrimidine-2,4-diamine;
$N^4$-[5-((1R,2R)-2-fluoro-cyclopropyl)-1H-pyrazol-3-yl]-$N^2$-methyl-$N^2$-[(S)-1-(1H-pyrrolo[3,2-b]pyridin-5-yl)-ethyl]-pyrimidine-2,4-diamine;
$N^4$-[5-((1R,2R)-2-fluoro-cyclopropyl)-1H-pyrazol-3-yl]-$N^2$-methyl-$N^2$-[(R)-1-(1H-pyrrolo[3,2-b]pyridin-5-yl)-ethyl]-pyrimidine-2,4-diamine;
$N^4$-[5-((1S,2S)-2-fluoro-cyclopropyl)-1H-pyrazol-3-yl]-$N^2$-methyl-$N^2$-[(S)-1-(1H-pyrrolo[3,2-b]pyridin-5-yl)-ethyl]-pyrimidine-2,4-diamine;
$N^4$-[5-(1S,2S)-2-fluoro-cyclopropyl)-1H-pyrazol-3-yl]-$N^2$-methyl-$N^2$-[(R)-1-(1H-pyrrolo[3,2-b]pyridin-5-yl)-ethyl]-pyrimidine-2,4-diamine;
$N^4$-[5-(1S,2R)-2-fluoro-cyclopropyl)-1H-pyrazol-3-yl]-$N^2$-methyl-$N^2$-[(S)-1-(1H-pyrrolo[3,2-b]pyridin-5-yl)-ethyl]-pyrimidine-2,4-diamine;
$N^4$-[5-((1S,2R)-2-fluoro-cyclopropyl)-1H-pyrazol-3-yl]-$N^2$-methyl-$N^2$-[(R)-1-(1H-pyrrolo[3,2-b]pyridin-5-yl)-ethyl]-pyrimidine-2,4-diamine;
$N^4$-[5-(1R,2S)-2-fluoro-cyclopropyl)-1H-pyrazol-3-yl]-$N^2$-methyl-$N^2$-[(S)-1-(1H-pyrrolo[3,2-b]pyridin-5-yl)-ethyl]-pyrimidine-2,4-diamine;
$N^4$-[5-((1R,2S)-2-fluoro-cyclopropyl)-1H-pyrazol-3-yl]-$N^2$-methyl-$N^2$-[(R)-1-(1H-pyrrolo[3,2-b]pyridin-5-yl)-ethyl]-pyrimidine-2,4-diamine;
$N^4$-[5-(1R,2R)-2-fluoro-cyclopropyl)-1H-pyrazol-3-yl]-$N^2$-[(S)-1-(1H-pyrrolo[3,2-b]pyridin-5-yl)-ethyl]-pyrimidine-2,4-diamine;
$N^4$-[5-((1S,2S)-2-fluoro-cyclopropyl)-1H-pyrazol-3-yl]-$N^2$-[(S)-1-(1H-pyrrolo[3,2-b]pyridin-5-yl)-ethyl]-pyrimidine-2,4-diamine;
$N^4$-[5-((1S,2R)-2-fluoro-cyclopropyl)-1H-pyrazol-3-yl]-$N^2$-[(S)-1-(1H-pyrrolo[3,2-b]pyridin-5-yl)-ethyl]-pyrimidine-2,4-diamine;
$N^4$-(5-cyclopropyl-1H-pyrazol-3-yl)-$N^2$-(3H-imidazo[4,5-c]pyridin-7-ylmethyl)-pyrimidine-2,4-diamine; and,
$N^4$-(5-cyclopropyl-1H-pyrazol-3-yl)-5-fluoro-$N^2$-(3H-imidazo[4,5-c]pyridin-7-ylmethyl)-pyrimidine-2,4-diamine;
$N^2$-[1-(6-chloro-1H-pyrrolo[3,2-b]pyridin-5-yl)ethyl]-$N^4$-(5-cyclopropyl-1H-pyrazol-3-yl)pyrimidine-2,4-diamine;
$N^4$-(5-cyclopropyl-1H-pyrazol-3-yl)-N2-(1H-pyrazolo[4,3-c]pyridin-4-ylmethyl)pyrimidine-2,4-diamine;
$N^4$-(5-cyclopropyl-1H-pyrazol-3-yl)-$N^2$-[(1S)-1-(6-fluoro-1H-pyrrolo[3,2-b]pyridin-5-yl)ethyl]pyrimidine-2,4-diamine;
$N^4$-(5-cyclopropyl-1H-pyrazol-3-yl)-$N^2$-[(6-fluoro-1H-pyrrolo[3,2-b]pyridin-5-yl)methyl]-N2-methyl-pyrimidine-2,4-diamine;
(S)—$N^2$-(1-(3H-imidazo[4,5-c]pyridin-6-yl)ethyl)-$N^4$-(5-cyclopropyl-1H-pyrazol-3-yl)pyrimidine-2,4-diamine;
(R)—$N^2$-(1-(3H-imidazo[4,5-c]pyridin-6-yl)ethyl)-$N^4$-(5-cyclopropyl-1H-pyrazol-3-yl)pyrimidine-2,4-diamine;
$N^4$-(5-cyclopropyl-1H-pyrazol-3-yl)-N2-methyl-$N^2$-(1H-pyrrolo[2,3-c]pyridin-4-ylmethyl)pyrimidine-2,4-diamine;
(R)—$N^2$-(1-(5H-pyrrolo[3,2-d]pyrimidin-2-yl)ethyl)-$N^4$-(5-cyclopropyl-1H-pyrazol-3-yl)-N2-ethylpyrimidine-2,4-diamine;
(S)—$N^2$-(1-(5H-pyrrolo[3,2-d]pyrimidin-2-yl)ethyl)-$N^4$-(5-cyclopropyl-1H-pyrazol-3-yl)-$N^2$-ethylpyrimidine-2,4-diamine; and,
$N^2$-[(1S)-1-(3-chloro-1H-pyrrolo[3,2-b]pyridin-5-yl)ethyl]-$N^4$-[5-[(1R,2S)-2-fluorocyclopropyl]-1H-pyrazol-3-yl]pyrimidine-2,4-diamine; or, a pharmaceutically acceptable salt thereof.

17. A composition comprising a compound according to claim 1 and at least one pharmaceutically acceptable carrier, excipient or diluent.

* * * * *